United States Patent
Palushi et al.

(10) Patent No.: US 12,016,612 B2
(45) Date of Patent: Jun. 25, 2024

(54) ENT ABLATION INSTRUMENT WITH ELECTRODE LOOP

(71) Applicants: Acclarent, Inc., Irvine, CA (US); Biosense Webster (Israel) Ltd., Yokneam (IL)

(72) Inventors: Jetmir Palushi, Irvine, CA (US); Henry F. Salazar, Pico Rivera, CA (US); Hany Abdelwahed, Irvine, CA (US); Assaf Govari, Haifa (IL); Vadim Gliner, Haifa (IL); Andres C. Altmann, Haifa (IL); Christopher T. Beeckler, Brea, CA (US); Shubhayu Basu, Anaheim, CA (US); Madison K. Vanosdoll, Cincinnati, OH (US); Alison D. Wright, Newport Beach, CA (US); Yehuda Algawi, Binyamina (IL); Behnam Amin, Mission Viejo, CA (US); Marc Dean, Ft. Worth, TX (US)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 189 days.

(21) Appl. No.: 17/387,589

(22) Filed: Jul. 28, 2021

(65) Prior Publication Data
US 2022/0054188 A1    Feb. 24, 2022

Related U.S. Application Data

(60) Provisional application No. 63/142,098, filed on Jan. 27, 2021, provisional application No. 63/092,751, (Continued)

(51) Int. Cl.
A61B 18/14    (2006.01)
A61B 90/30    (2016.01)
(Continued)

(52) U.S. Cl.
CPC .............. *A61B 18/14* (2013.01); *A61B 90/30* (2016.02); *A61B 2018/00077* (2013.01); (Continued)

(58) Field of Classification Search
CPC . A61B 18/1485; A61B 18/1206; A61B 18/14; A61B 2018/00077;
(Continued)

(56) References Cited

U.S. PATENT DOCUMENTS 3,835,842 A * 9/1974 Iglesias .............. A61B 1/00135
600/105
5,836,947 A    11/1998 Fleischman et al.
(Continued)

FOREIGN PATENT DOCUMENTS

CN    202723816 U    2/2013
CN    104287686 A    1/2015
(Continued)

OTHER PUBLICATIONS

Fukutake, Tomoshige, et al. "Laser surgery for allergic rhinitis." *Archives of Otolaryngology-Head & Neck Surgery* 112.12 (1986): 1280-1282.
(Continued)

*Primary Examiner* — Michael F Peffley
(74) *Attorney, Agent, or Firm* — Frost Brown Todd LLP

(57) ABSTRACT

An apparatus includes a shaft assembly and an electrode assembly at a distal end of the shaft assembly. The electrode assembly includes a first conductive segment extending along a first angular range at the distal end of the shaft assembly. The first conductive segment is operable to apply RF energy to tissue at a first polarity. The electrode assembly further includes a second conductive segment angularly spaced apart from the first conductive segment. The second conductive segment extends along a second angular range at
(Continued)

the distal end of the shaft assembly. The second conductive segment is operable to apply RF energy to tissue at a second polarity such that the first and second conductive segments are operable to apply bipolar RF energy to tissue.

20 Claims, 40 Drawing Sheets

Related U.S. Application Data filed on Oct. 16, 2020, provisional application No. 63/067,495, filed on Aug. 19, 2020.

(51) Int. Cl.
  *A61B 18/00* (2006.01)
  *A61B 18/12* (2006.01)

(52) U.S. Cl.
  CPC .............. *A61B 2018/00083* (2013.01); *A61B 2018/00327* (2013.01); *A61B 2018/00577* (2013.01); *A61B 2018/00982* (2013.01); *A61B 2018/126* (2013.01); *A61B 2018/1407* (2013.01); *A61B 2018/1425* (2013.01); *A61B 2218/007* (2013.01)

(58) Field of Classification Search
  CPC ........... A61B 2018/00083; A61B 2018/00327; A61B 2018/00577; A61B 2018/126; A61B 2018/1407; A61B 2018/1425; A61B 2018/143; A61B 2018/00214; A61B 2018/00279; A61B 2018/00642; A61B 2018/00815; A61B 2018/00875; A61B 2018/1432; A61B 2018/1435; A61B 2018/1472; A61B 2018/1475; A61B 2218/002; A61B 1/00087; A61B 1/00097; A61B 1/0052; A61B 1/015; A61B 1/126; A61B 1/233
  USPC .......................................................... 606/46
  See application file for complete search history.

(56) References Cited

U.S. PATENT DOCUMENTS

| | | | |
|---|---|---|---|
| 5,849,011 A * | 12/1998 | Jones .................. | A61B 18/1477 606/49 |
| 5,873,877 A * | 2/1999 | McGaffigan ....... | A61B 1/00177 606/41 |
| 6,109,268 A | 8/2000 | Thapliyal et al. | |
| 6,193,714 B1 | 2/2001 | McGaffigan et al. | |
| 6,221,039 B1 * | 4/2001 | Durgin ............... | A61B 18/1492 606/48 |
| 6,361,531 B1 | 3/2002 | Hissong | |
| 6,526,318 B1 | 3/2003 | Ansarinia | |
| 6,716,179 B2 | 4/2004 | Burbank et al. | |
| 7,087,040 B2 | 8/2006 | McGuckin, Jr. et al. | |
| 7,429,262 B2 * | 9/2008 | Woloszko .......... | A61B 18/1482 606/46 |
| 7,678,108 B2 | 3/2010 | Christian et al. | |
| 7,720,521 B2 | 5/2010 | Chang et al. | |
| 7,771,421 B2 | 8/2010 | Stewart et al. | |
| 7,789,881 B2 * | 9/2010 | Weitzner ............ | A61B 18/1482 606/41 |
| 7,875,025 B2 | 1/2011 | Cockburn et al. | |
| 8,216,234 B2 | 7/2012 | Long | |
| 8,262,574 B2 | 9/2012 | Placek et al. | |
| 8,343,035 B2 | 1/2013 | To | |
| 8,435,237 B2 * | 5/2013 | Bahney .............. | A61B 18/1482 606/45 |
| 8,632,538 B2 | 1/2014 | Pearson et al. | |
| 8,936,594 B2 | 1/2015 | Wolf et al. | |
| 9,072,597 B2 | 7/2015 | Wolf et al. | |
| 9,289,582 B2 | 3/2016 | Suehara | |
| 9,308,039 B2 | 4/2016 | Azure | |
| 9,339,328 B2 | 5/2016 | Ortiz et al. | |
| 9,415,194 B2 | 8/2016 | Wolf et al. | |
| 9,439,716 B2 * | 9/2016 | Batchelor .......... | A61B 18/1485 |
| 9,668,643 B2 | 6/2017 | Kennedy, II et al. | |
| 9,687,288 B2 | 6/2017 | Saadat | |
| 9,693,759 B2 | 7/2017 | Seguy | |
| 9,814,523 B2 | 11/2017 | Condie et al. | |
| 9,888,832 B2 | 2/2018 | Schwartz et al. | |
| 10,004,424 B2 | 6/2018 | Wirtz et al. | |
| 10,154,888 B2 | 12/2018 | Sagon et al. | |
| 10,244,927 B2 | 4/2019 | Kennedy, II et al. | |
| 10,258,406 B2 | 4/2019 | Long | |
| 10,463,242 B2 | 11/2019 | Kesten et al. | |
| 10,561,370 B2 | 2/2020 | Salazar et al. | |
| 10,631,927 B2 | 4/2020 | Avitall | |
| 10,758,116 B2 | 9/2020 | Piskun | |
| 2002/0049438 A1 | 4/2002 | Sharkey et al. | |
| 2003/0139789 A1 | 7/2003 | Tvinnereim et al. | |
| 2004/0186469 A1 | 9/2004 | Woloszko et al. | |
| 2004/0204747 A1 | 10/2004 | Kemeny et al. | |
| 2005/0283148 A1 | 12/2005 | Janssen et al. | |
| 2006/0004323 A1 | 1/2006 | Chang et al. | |
| 2006/0271032 A1 | 11/2006 | Chin et al. | |
| 2009/0054728 A1 | 2/2009 | Trusty | |
| 2009/0149849 A1 | 6/2009 | Lin et al. | |
| 2009/0222001 A1 | 9/2009 | Greeley et al. | |
| 2010/0274164 A1 | 10/2010 | Juto | |
| 2011/0288540 A1 | 11/2011 | Wright et al. | |
| 2012/0035249 A1 | 2/2012 | Kuhn et al. | |
| 2012/0101499 A1 | 4/2012 | Lagodzki | |
| 2014/0257036 A1 | 9/2014 | Choi et al. | |
| 2014/0276757 A1 | 9/2014 | Ellman | |
| 2014/0364725 A1 | 12/2014 | Makower | |
| 2016/0331459 A1 | 11/2016 | Townley et al. | |
| 2017/0231474 A1 | 8/2017 | Saadat et al. | |
| 2017/0325790 A1 | 11/2017 | Blitzer et al. | |
| 2018/0161092 A1 | 6/2018 | Greifeneder et al. | |
| 2019/0070395 A1 | 3/2019 | Govari et al. | |
| 2019/0374280 A1 | 12/2019 | Salazar et al. | |
| 2020/0179040 A1 | 6/2020 | Townley et al. | |
| 2021/0361912 A1 | 11/2021 | Matlock et al. | |
| 2021/0386274 A1 | 12/2021 | Palushi et al. | |

FOREIGN PATENT DOCUMENTS

| | | |
|---|---|---|
| CN | 110876658 A | 3/2020 |
| WO | WO 1999/032041 A1 | 7/1999 |
| WO | WO 2011/005903 A2 | 1/2011 |
| WO | WO 2011/025830 A1 | 3/2011 |
| WO | WO 2015/033094 A1 | 3/2015 |
| WO | WO 2016/190455 A1 | 12/2016 |
| WO | WO 2018/183643 A1 | 10/2018 |
| WO | WO 2020/156205 A1 | 8/2020 |
| WO | WO 2022/038494 A1 | 2/2022 |
| WO | WO 2022/269496 A1 | 12/2022 |

OTHER PUBLICATIONS

Gindros, George, et al. "Mucosal changes in chronic hypertrophic rhinitis after surgical turbinate reduction." *European archives of oto-rhino-laryngology* 266.9 (2009): 1409-1416.

Ho, Ki-Hong Kevin, et al. "Electromechanical reshaping of septal cartilage." *The Laryngoscope* 113.11 (2003): 1916-1921.

U.S. Appl. No. 17/324,201, entitled "ENT Guide with Advanceable Instrument and Advanceable Endoscope Shaft," filed May 19, 2021.

U.S. Appl. No. 17/557,256, entitled "ENT Instrument with Deformable Guide Having Translatable Imaging Feature," filed Dec. 21, 2021.

U.S. Appl. No. 17/404,088, entitled "ENT Instrument with Expandable Ablation Feature," filed Aug. 17, 2021.

U.S. Appl. No. 63/028,609, entitled "Shaft Deflection Control Assembly for ENT Guide Instrument," filed May 22, 2020.

U.S. Appl. No. 63/037,640, entitled "ENT Guide with Advanceable Instrument and Advanceable Endoscope Shaft," filed Jun. 11, 2020.

(56) References Cited

OTHER PUBLICATIONS

U.S. Appl. No. 63/067,495, entitled "ENT Ablation Instrument with Electrode Loop," filed Aug. 19, 2020.
U.S. Appl. No. 63/080,066, entitled "ENT Instrument with Expandable Ablation Feature," filed Sep. 18, 2020.
International Search Report and Written Opinion dated Nov. 15, 2021, for International Application No. PCT/IB2021/057534, 11 pages.
International Search Report and Written Opinion dated Apr. 24, 2023, for International Application No. PCT/IB2022/061560, 18 pages.

* cited by examiner

ENT ABLATION INSTRUMENT WITH ELECTRODE LOOP

PRIORITY

This application claims priority to U.S. Provisional Patent App. No. 63/067,495, entitled "ENT Ablation Instrument with Electrode Loop," filed Aug. 19, 2020, the disclosure of which is incorporated by reference herein; U.S. Provisional Patent App. No. 63/092,751, entitled "ENT Instrument with Ablation Loop and Ablation Needles," filed Oct. 16, 2020, the disclosure of which is incorporated by reference herein; and U.S. Provisional Patent App. No. 63/142,098, entitled "ENT Instrument with Ablation Loop and Ablation Needles," filed Jan. 27, 2021, the disclosure of which is incorporated by reference herein.

BACKGROUND

Rhinitis is a medical condition that presents as irritation and inflammation of the mucous membrane within the nasal cavity. The inflammation results in the generation of excessive amounts of mucus, which can cause runny nose, nasal congestion, sneezing, and/or post-nasal drip. Allergenic rhinitis is an allergic reaction to environmental factors such as airborne allergens, while non-allergenic (or "vasomotor") rhinitis is a chronic condition that presents independently of environmental factors. Conventional treatments for rhinitis include antihistamines, topical or systemic corticosteroids, and topical anticholinergics, for example.

For cases of intractable rhinitis in which the symptoms are severe and persistent, an additional treatment option is the surgical removal of a portion of the vidian (or "pterygoid") nerve—a procedure known as vidian neurectomy. The theoretical basis for vidian neurectomy is that rhinitis is caused by an imbalance between parasympathetic and sympathetic innervation of the nasal cavity, and the resultant over stimulation of mucous glands of the mucous membrane. Vidian neurectomy aims to disrupt this imbalance and reduce nasal mucus secretions via surgical treatment of the vidian nerve. However, in some instances, vidian neurectomy can cause collateral damage to the lacrimal gland, which is innervated by the vidian nerve. Such damage to the lacrimal gland may result in long-term health complications for the patient, such as chronic dry eye. Posterior nasal neurectomy, or surgical removal of a portion of the posterior nasal nerves, may be an effective alternative to vidian neurectomy for treating intractable rhinitis.

FIG. 1 depicts a left sagittal view of a portion of a patient's head, showing the nasal cavity (10), the frontal sinus (12), the sphenoid sinus (14), and the sphenoid bone (16). The nasal cavity (10) is bounded laterally by the nasal wall (18), which includes an inferior turbinate (20), a middle turbinate (22), and a superior turbinate (24). The vidian nerve (32) resides within the vidian (or "pterygoid") canal (30), which is defined in part by the sphenoid bone (16) and is located posterior to the sphenoid sinus (14), approximately in alignment with the middle turbinate (22). The vidian nerve (32) is formed at its posterior end by the junction of the greater petrosal nerve (34) and the deep petrosal nerve (36); and joins at its anterior end with the pterygopalatine ganglion (38), which is responsible for regulating blood flow to the nasal mucosa. The posterior nasal nerves (40) join with the pterygopalatine ganglion (38) and extend through the region surrounding the inferior turbinate (20).

While instruments and methods for performing vidian neurectomies, posterior nasal neurectomies, and turbinate reductions are known, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

Figure 1:
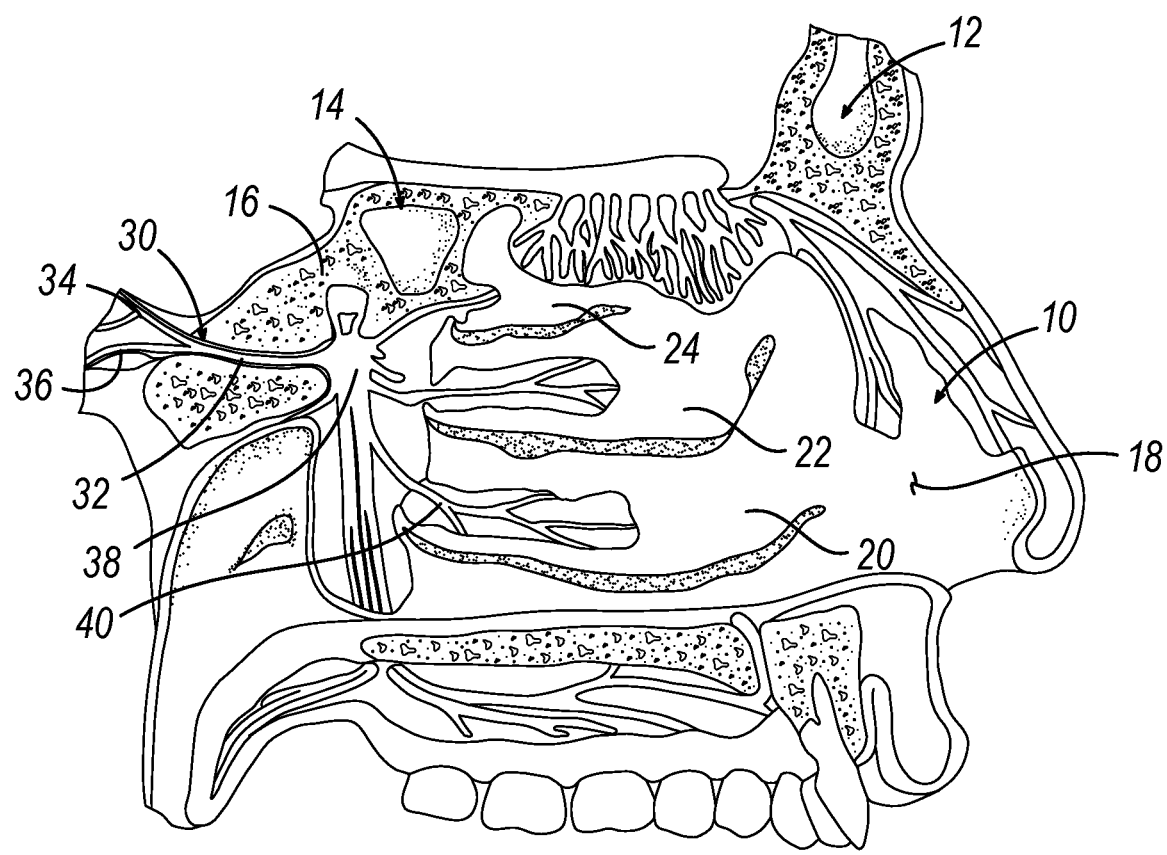
FIG. 1 depicts a left sagittal view of a portion of a patient's head, showing details of certain paranasal sinuses and nerves, including the vidian nerve and the posterior nasal nerve.
Figure 2:
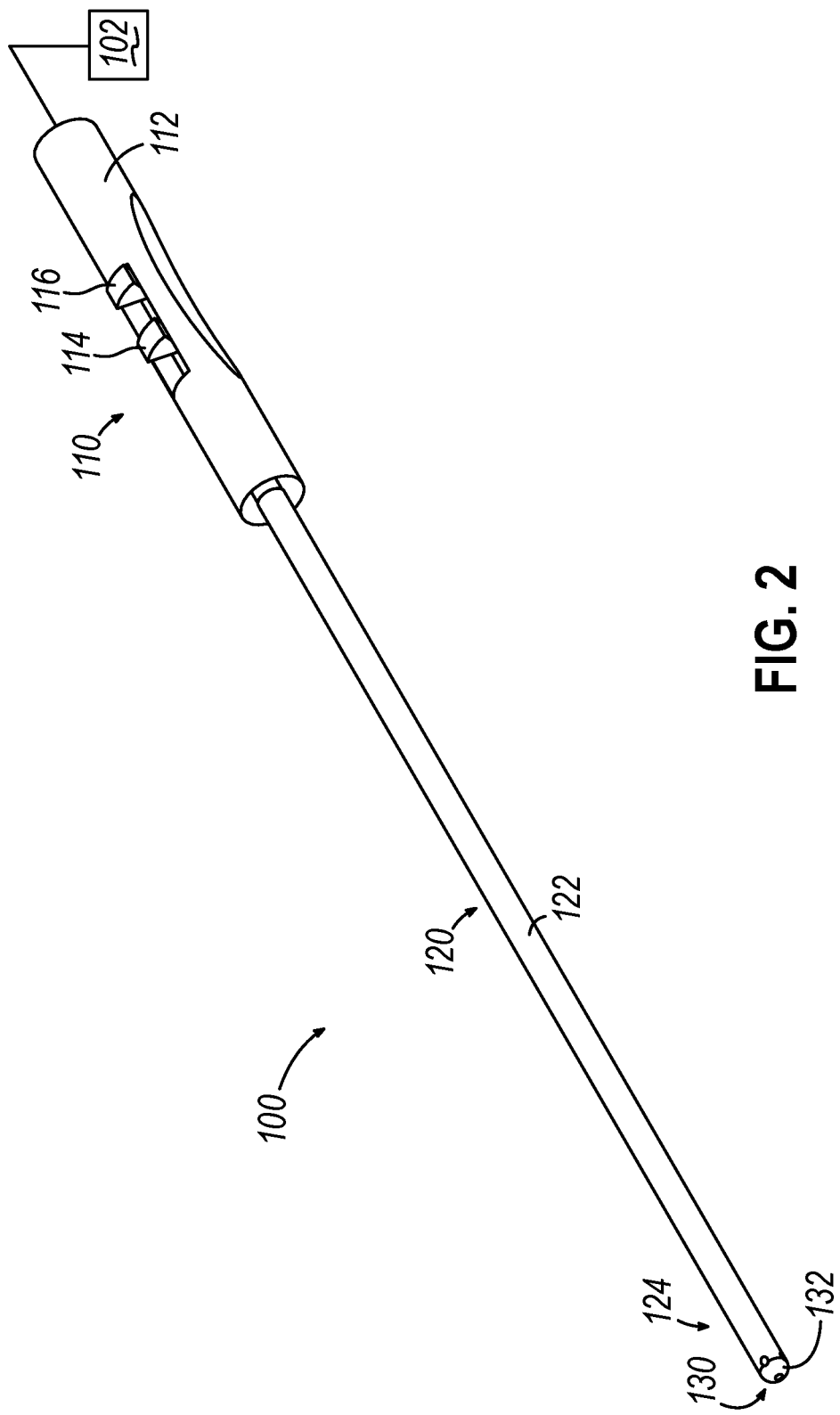
FIG. 2 depicts a perspective view of an example of an instrument that may be used to perform an ablation procedure in a nasal cavity.
Figure 3:
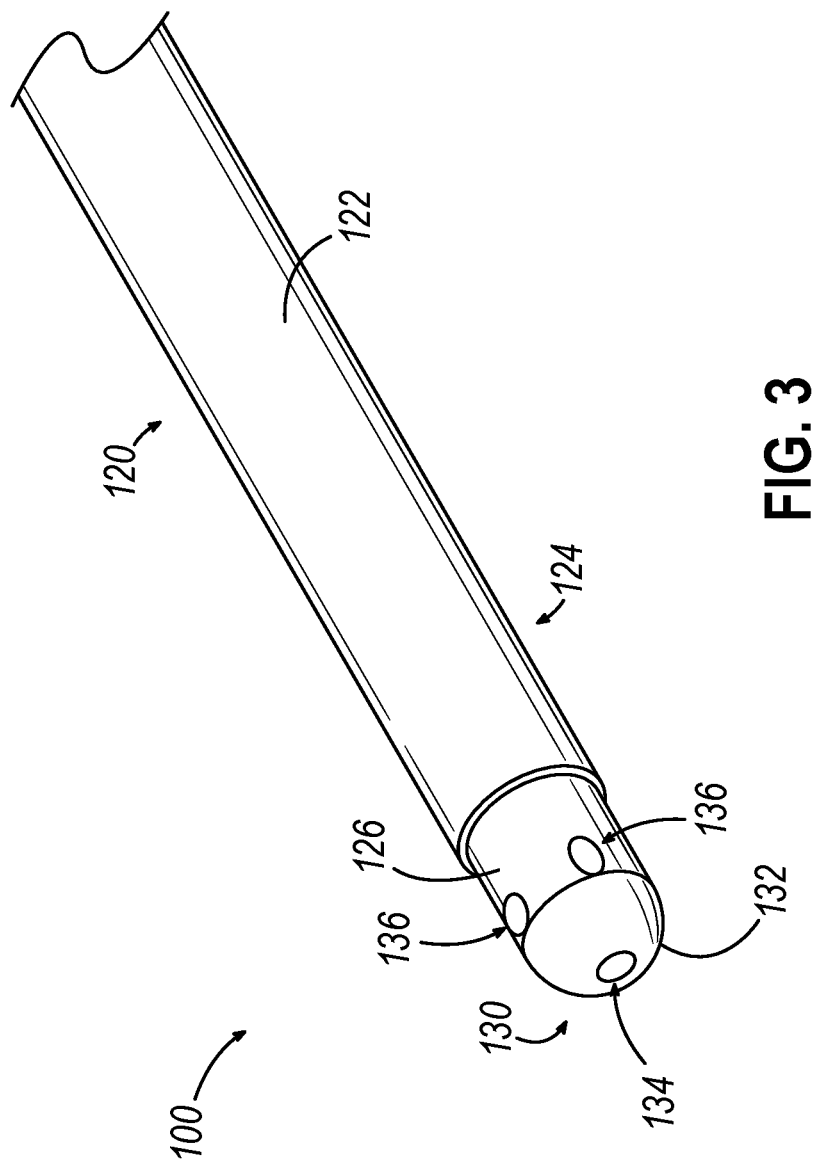
FIG. 3 depicts a perspective view of a distal portion of a shaft assembly of the instrument of FIG. 2, with a distal needle electrode in a retracted position, with a set of oblique needle electrodes in a retracted position, and with a sheath in an advanced position.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. SHALLOW, DEEP, AND VOLUMETRIC ABLATION

In some clinical scenarios, it may be desirable to apply radiofrequency (RF) energy to tissue to ablate the tissue. This may include contacting a surface of tissue with one or more electrodes, then activating the one or more electrodes to apply the RF energy to the tissue. In cases where one electrode is used, a ground pad may be placed in contact with the skin of the patient, and the one electrode that contacts the targeted tissue surface may apply monopolar RF energy to the targeted tissue surface. In cases where two or more electrodes are used, the two or more electrodes may be placed in contact with the targeted tissue surface and may be activated to apply bipolar RF energy to the targeted tissue surface. In either case, the RF energy may ablate the tissue to provide a desired therapeutic effect.

RF ablation electrodes may also come in the form of needles that penetrate tissue and are activated to apply RF energy once the needles are inserted in tissue. Unlike tissue surface contacting RF ablation electrodes, needle electrodes may facilitate ablation far past the surface of the tissue. In some cases, needle electrodes may avoid ablating the a tissue surface despite the penetration of the needle electrodes through the tissue surface, where only sub-surface tissue is ablated.

In the context of some ear, nose, and throat (ENT) ablation procedures, it may be desirable to provide a relatively shallow RF ablation, such that only tissue surface contacting electrodes are used. In some other ENT scenarios, it may be desirable to provide a relatively deep RF ablation, such that tissue penetrating needle electrodes are used. In still other ENT scenarios, it may be desirable to provide a combination of shallow ablation and deep ablation, thereby resulting in a volumetric ablation, through the combined use of tissue surface contacting electrodes and tissue penetrating needle electrodes.

In view of the foregoing, it may be desirable to provide an ablation instrument that is operable to perform relatively shallow RF ablation, relatively deep RF ablation, or volumetric ablation (i.e., combining shallow and deep ablation), without requiring the use of more than one instrument. In other words, it may be desirable to provide a single RF ablation instrument that is operable to transition between a shallow ablation modality, a deep ablation modality, and a volumetric ablation modality, subject the selection of the instrument operator. The following provides several examples of RF ablation instruments that enable selectability between these modalities. While these examples are described in the context of ENT procedures, the instruments described below may be used in other procedures in other regions of a patient's anatomy as will be apparent to those skilled in the art in view of the teachings herein.

II. ABLATION INSTRUMENT WITH AXIAL AND OBLIQUE NEEDLE ELECTRODES

FIG. 1 shows an example of an instrument (100) that may be used to deliver RF energy to tissue within a nasal cavity or elsewhere within the head of a patient. For instance, instrument (100) may be used to ablate a nerve (e.g., the posterior nasal nerve (40)), ablate a turbinate (e.g., any of turbinates (20, 22, 24)), or ablate any other kind of anatomical structure in the head of a patient. Instrument (100) of this example includes a handle assembly (110), a shaft assembly (120), and an end effector (130). Instrument (100) is coupled with an RF generator (102), which is operable to generate RF electrosurgical energy for delivery to tissue via electrodes (140, 150) as will be described in greater detail below.

Handle assembly (110) of this example includes a body (112), a first slider (114), and a second slider (116). Body (112) is sized and configured to be grasped and operated by a single hand of an operator, such as via a power grip, a pencil grip, or any other suitable kind of grip. Each slider (114, 116) is operable to translate longitudinally relative to body (112). Sliders (114, 116) are operable to translate independently relative to each other in some versions. Slider (114) is coupled with electrode (140) and is thus operable to translate electrode (140) longitudinally as will be described in greater detail below. Slider (116) is coupled with electrodes (150) and is thus operable to translate electrodes (150) longitudinally as will be described in greater detail below.

While sliders (114, 116) are the form of user inputs in handle assembly (110) of the present example, handle assembly (110) may include various other kinds of user inputs in addition to, or in lieu of, sliders (114, 116). In some versions, handle assembly (110) also includes one or more buttons or other electrode activation features. Other suitable kinds of user input features that may be incorporated into handle assembly (110) will be apparent to those skilled in the art in view of the teachings herein. User input features outside of handle assembly (110) may include, but need not be limited to, one or more footswitches, one or more user input features on RF generator (102), etc.

Shaft assembly (120) of the present example extends distally from handle assembly (110) and includes an outer sheath (122) that is operable to translate longitudinally relative to handle assembly (110). In some versions, handle assembly (110) includes an actuator (e.g., slider, etc.) that is operable to drive translation of outer sheath (122). In some other versions, a grip or other actuator is secured to the exterior of outer sheath (122) and is configured to be manipulated by an operator to translate outer sheath (122) relative to handle assembly (110). As best seen in FIGS. 2-7, shaft assembly (120) also includes an inner shaft (126), with a plurality of ring electrodes (128) positioned about inner shaft (126) at the distal portion (124) of shaft assembly (120). Outer sheath (122) is operable to selectively cover or uncover ring electrodes (128) based on the longitudinal position of outer sheath (122) relative to handle assembly (110). Ring electrodes (128) are operable to provide RF ablation of tissue as will be described in greater detail below.

In some versions, shaft assembly (120) is rigid along its entire length. In some other versions, at least a portion of shaft assembly (120) is bendable. For instance, some variations of shaft assembly (120) may be malleable along distal portion (124). As another example, some variations of shaft assembly (120) may provide steering capability along distal portion (124). For instance, one or more pull wires may be actuated to bend distal portion (124) and thereby deflect distal portion (124) laterally away from a central longitudinal axis. Various suitable ways in which shaft assembly (120) may incorporate malleability, steerability, or other bendability will be apparent to those skilled in the art in view of the teachings herein. In versions that provide malleability, steerability, or other bendability in distal portion (124) or elsewhere within shaft assembly (120), shaft assembly (120) may include features that prevent the bendable section of shaft assembly (120) from kinking or otherwise jamming needle electrodes (140, 150), such that needle electrodes (140, 150) may longitudinally translate freely along shaft assembly (120) even when the bendable region of shaft assembly (120) is in a bent state. Such anti-kinking features may include a longitudinally spaced array of annular bodies. In some versions, ring electrodes (128), which are described in greater detail below, may provide anti-kinking functionality in shaft assembly (120) in addition to providing RF energy delivery capabilities.

End effector (130) is positioned at distal portion (124) of shaft assembly (120). End effector (130) includes a dome-shaped tip (132) that is fixedly secured to the distal end of inner shaft (126). Tip (132) defines a central opening (134) that is aligned with the longitudinal axis of shaft assembly (120). An array of lateral openings (136) are formed at the distal end of inner shaft (126), just proximal to tip (132). In the present example, inner shaft (126) includes four lateral openings (136) that are angularly spaced apart from each other equidistantly about the central longitudinal axis of shaft assembly (120). In other versions, more or fewer than four lateral openings (136) may be provided. While openings (136) are laterally presented at the outer surface of inner shaft (126) in the present example, inner shaft (126) may include internal guide features (not shown) leading to openings (136), with such internal guide features being oriented obliquely or otherwise non-perpendicularly relative to the central longitudinal axis of shaft assembly (120). Such internal guide features may assist in guiding needle electrodes (150) along oblique exit paths out through openings (136) as will be described in greater detail below. As used herein, the terms "oblique" and "obliquely" shall be read to include relationships where a structural element extends along a curve that bends away from a straight axis; in addition to including relationships where a structural element extends along a straight path that is non-parallel with a straight axis.

Figure 4:
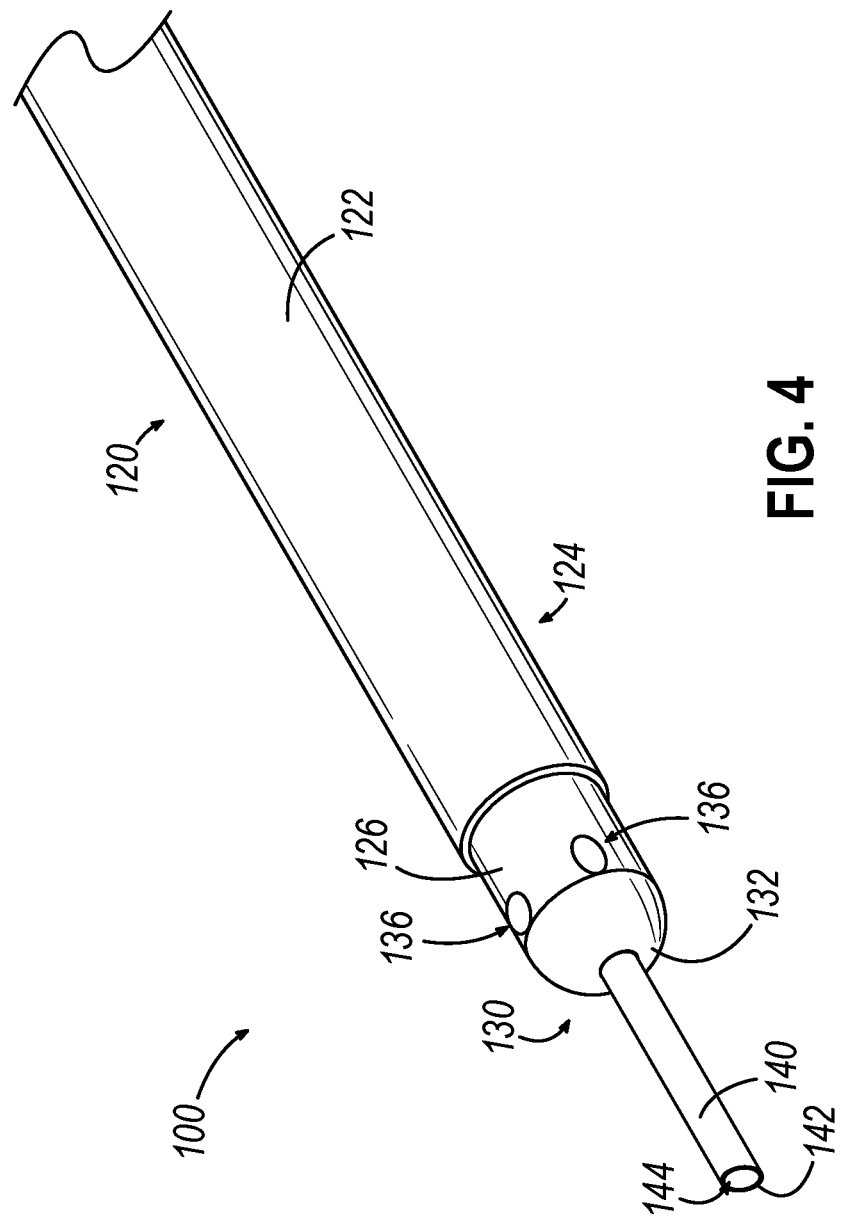
FIG. 4 depicts a perspective view of the distal portion of the shaft assembly of FIG. 3, with the distal needle electrode in an advanced position, with the set of oblique needle electrodes in the retracted position, and with the sheath in the advanced position.

In some scenarios, as shown in FIG. 4, end effector (130) further includes a distal needle electrode (140). By way of example only, needle electrode (140) may be coupled with slider (114), such that needle electrode (140) is advanced distally to the position shown in FIG. 4 when slider (114) is advanced distally along body (112) of handle assembly (110). Needle electrode (140) is positioned and configured to exit tip (132) via opening (134). Needle electrode (140) includes a sharp tip (142) that is configured to pierce tissue as needle electrode (140) is advanced distally. In the present example, needle electrode (140) also defines a lumen (144), though lumen (144) may be omitted in some versions. In some versions where lumen (144) is included, needle electrode (140) may be used to deliver fluid (e.g., irrigation fluid, therapeutic substance, etc.) to tissue.

Needle electrode (140) is coupled with RF generator (102) (e.g., via one or more wires, etc.), such that needle electrode (140) is operable to deliver RF energy to tissue. In some scenarios, a ground pad is placed in contact with the skin of the patient, and needle electrode (140) is activated to apply monopolar RF energy to tissue. In some other scenarios, needle electrode (140) cooperates with one or more other electrodes (128, 150) of instrument (100) to apply bipolar RF energy to tissue.

As another variation, tip (132) may be configured to serve as an electrode, such that tip (132) and needle electrode (140) may cooperate to apply bipolar RF energy to tissue. For instance, needle electrode (140) may serve as an active electrode while tip (132) serves as a return electrode. In versions where tip (132) includes an electrically conductive material that allows tip (132) to serve as an electrode, at least a proximal portion of needle electrode (140) may include an electrically insulative coating or sheath, etc. to prevent short circuiting between needle electrode (140) and tip (132). In addition, or in the alternative, a portion of tip (132) may include an electrically insulative coating or sheath, etc. to prevent short circuiting between needle electrode (140) and tip (132). Other suitable ways in which needle electrode (140) and/or tip (132) may be used to apply monopolar or bipolar RF energy to tissue will be apparent to those skilled in the art in view of the teachings herein. In addition to, or in lieu of, being used to provide ablation of tissue via RF energy, needle electrode (140) and/or tip (132) may be used to provide electroporation of tissue. Such electroporation may be provided to facilitate delivery of therapeutic substances, etc. to the tissue.

Figure 5:
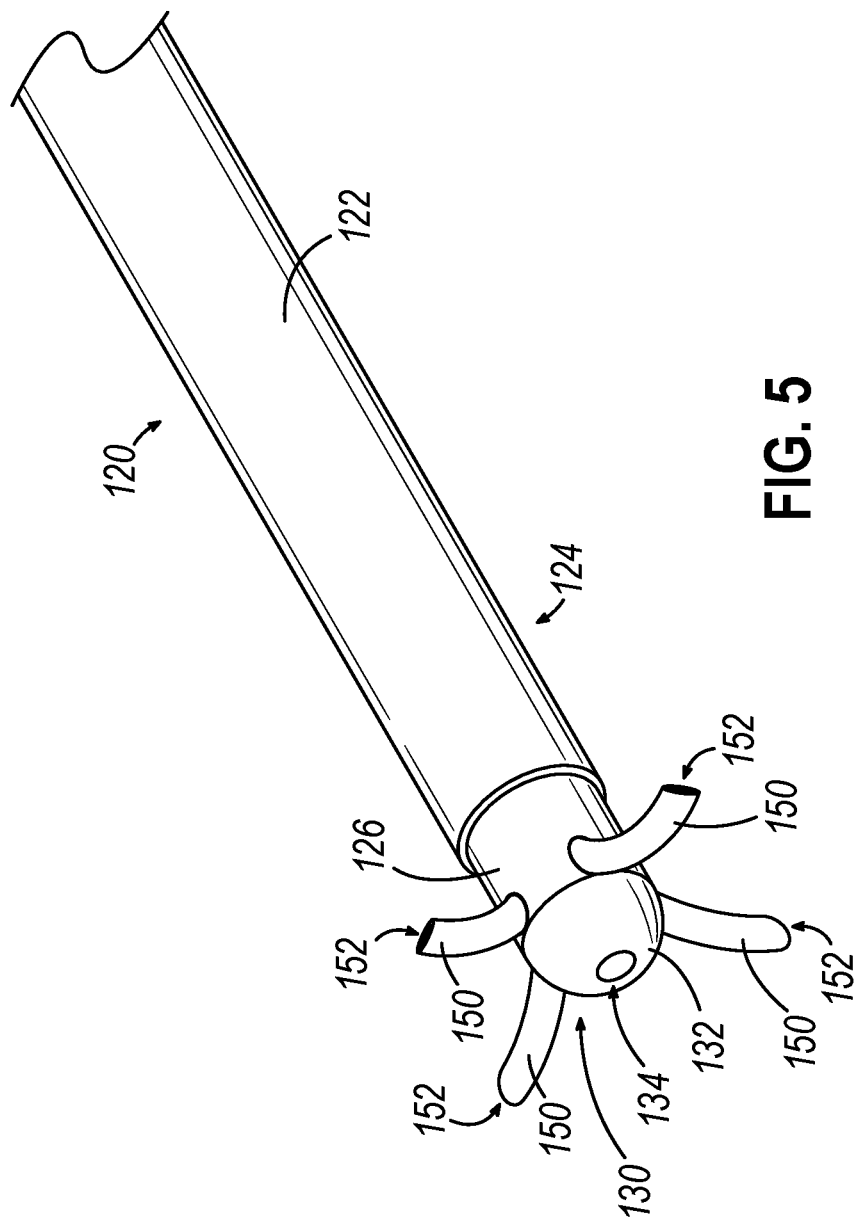
FIG. 5 depicts a perspective view of the distal portion of the shaft assembly of FIG. 3, with the distal needle electrode in the retracted position, with the set of oblique needle electrodes in an advanced position, and with the sheath in the advanced position.

In some scenarios, as shown in FIG. 5, end effector (130) further includes a plurality of oblique needle electrodes (150). While four needle electrodes (150) are shown in the present example, instrument (100) may instead include more or fewer than four needle electrodes (150). By way of example only, needle electrodes (150) may be coupled with slider (116), such that needle electrodes (150) are simultaneously advanced distally to the position shown in FIG. 5 when slider (116) is advanced distally along body (112) of handle assembly (110). While all needle electrodes (150) are coupled with slider (116) in the present example, such that needle electrodes (150) are simultaneously advanced distally when slider (116) is advanced distally, other versions may include separate actuators for needle electrodes (150) (e.g., such that each needle electrode (150) is configured to be advanced individually and independently relative to the other needle electrodes (150)). Needle electrodes (150) are positioned and configured to inner shaft (126) via respective opening (136). Each needle electrode (150) includes a sharp tip (152) that is configured to pierce tissue as needle electrode (150) is advanced distally. In some versions, each needle electrode (150) also defines a lumen (not shown), though such a lumen may be omitted in some versions. In some versions where each needle electrode (150) includes a lumen, needle electrodes (150) may be used to deliver fluid (e.g., irrigation fluid, therapeutic substance, etc.) to tissue.

Each needle electrode (150) is coupled with RF generator (102) (e.g., via one or more wires, etc.), such that needle electrodes (150) are operable to deliver RF energy to tissue. In some scenarios, a ground pad is placed in contact with the skin of the patient, and each needle electrode (150) may be activated to apply monopolar RF energy to tissue. All needle electrodes (150) may thus have the same polarity. In some other scenarios, needle electrodes (150) cooperate with each other to apply bipolar RF energy to tissue. For instance, two needle electrodes (150) may serve as active electrodes while the other two needle electrodes (150) may serve as return electrodes. In such versions, the two active needle electrodes (150) may be angularly spaced apart from each other by 180 degrees or may be spaced apart from each other by 90 degrees. As yet another example, in versions where tip (132) is configured to serve as an RF electrode, one or more of needle electrodes (150) may cooperate with tip (132) to apply bipolar RF energy to tissue.

Needle electrodes (150) of the present example are resiliently biased to curve outwardly as shown in FIG. 5 as needle electrodes (150) exit out through openings (136). As noted above, inner shaft (126) may include internal guide features that guide needle electrodes (150) out through openings (136) as needle electrodes (150) are advanced distally. Such guide features may further assist needle electrodes (150) in achieving the outwardly splayed configuration shown in FIG. 5 when needle electrodes (150) are advanced to the distal position. By way of example only, needle electrodes (150) may include nitinol or any other suitable resilient material to impart the bias to assume the curved configuration shown in FIG. 5.

In some versions, needle electrodes (150) are biased to extend along hyperbolic curves when needle electrodes (150) are advanced distally. In some other versions, needle electrodes (150) are biased to extend along a single-radius curvature when needle electrodes (150) are advanced distally. As yet another example, needle electrodes (150) may be resiliently biased to assume straight configurations, and internal guide features in inner shaft (126) may urge needle electrodes (150) to extend along straight oblique paths when needle electrodes (150) are advanced distally. Regardless of whether needle electrodes (150) are resiliently biased to assume a curved configuration or a straight configuration, needle electrodes (150) may be regarded as extending obliquely outwardly relative to the longitudinal axis of shaft assembly (120) when needle electrodes (150) are advanced distally. Other suitable configurations will be apparent to those skilled in the art in view of the teachings herein. Some versions may also permit cessation of needle electrode (150) advancement at any suitable position, such that needle electrodes (150) may be advanced further distally, or less distal, than the position shown in FIG. 5, depending on the desired depth of tissue penetration.

As with needle electrode (140), needle electrodes (150) may include an insulative coating or sheath, etc., along at least a portion of electrodes (150) to prevent short circuiting with adjacent conductive components. Also as with needle electrode (140), needle electrodes (150) may be used to provide ablation of tissue via RF energy, electroporation of tissue, or other electrically induced tissue effects.

Figure 6:
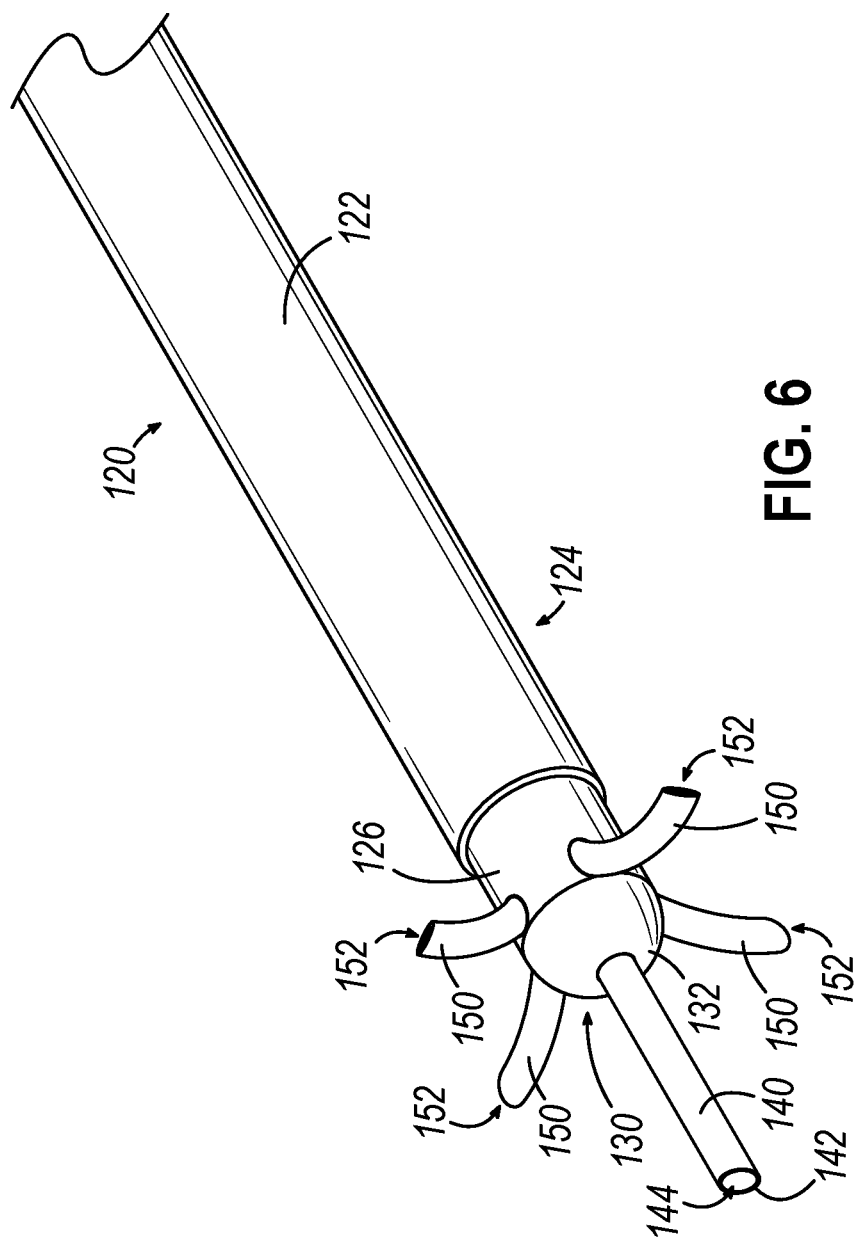
FIG. 6 depicts a perspective view of the distal portion of the shaft assembly of FIG. 3, with the distal needle electrode in the advanced position, with the set of oblique needle electrodes in the advanced position, and with the sheath in the advanced position.

In some scenarios, the operator may wish to configure end effector (130) with needle electrode (140) and needle electrodes (150) deployed simultaneously as shown in FIG. 6. This arrangement may be achieved by advancing both sliders (114, 116) distally along body (112). When end effector (130) is configured as shown in FIG. 6, needle electrodes (140, 150) may cooperate in any suitable fashion, with or without tip (132) in versions where tip (132) is configured to serve as an electrode), to apply RF energy to tissue.

Figure 7:
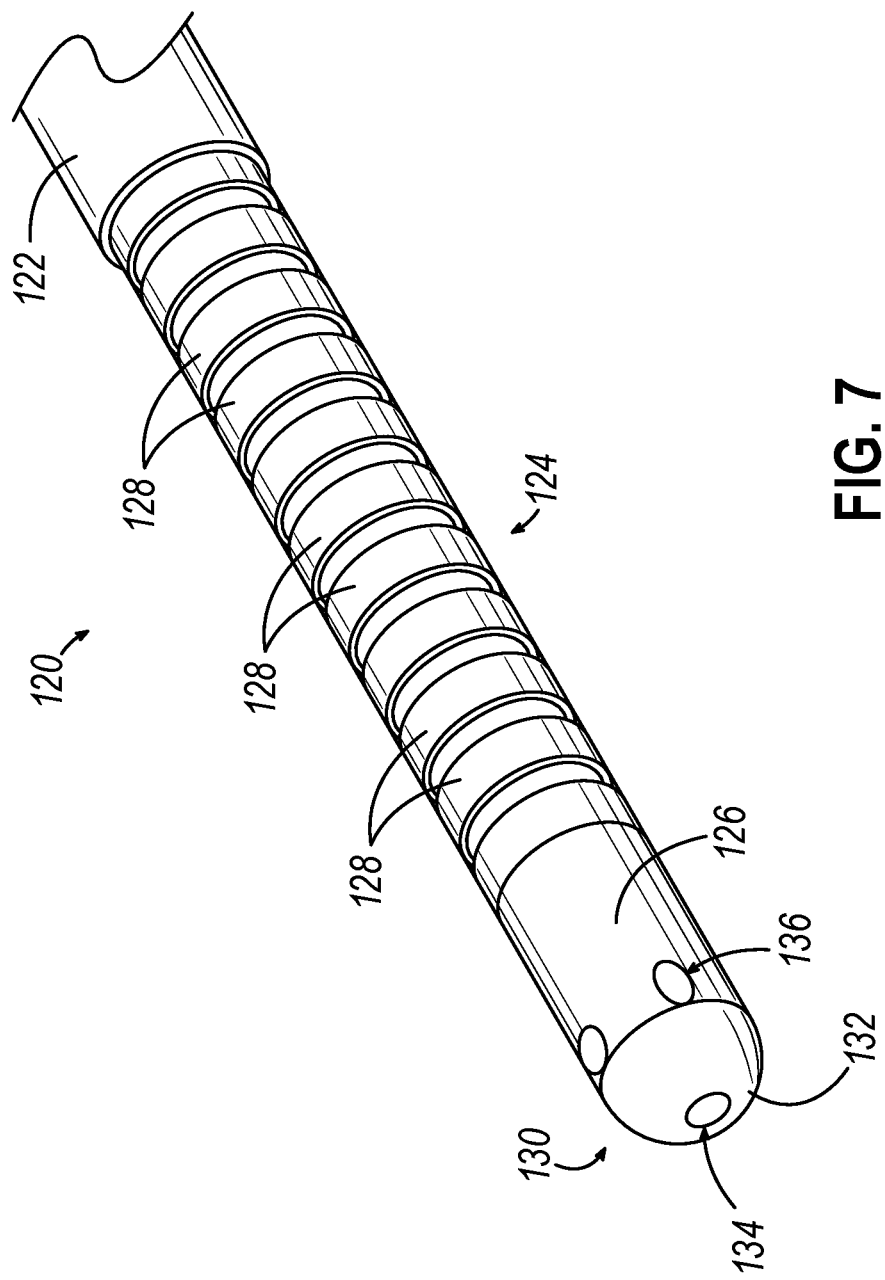
FIG. 7 depicts a perspective view of the distal portion of the shaft assembly of FIG. 3, with the distal needle electrode in the retracted position, with the set of oblique needle electrodes in the retracted position, and with the sheath in a retracted position.

FIG. 7 shows another example of an operational state of instrument (100). In this state, sheath (122) is retracted proximally to reveal ring electrodes (128). Sheath (122) may be formed of a material that is not electrically conductive. In some versions, some ring electrodes (128) are configured to serve as active electrodes while other ring electrodes (128) are configured to serve as return electrodes, such that ring electrodes (128) are operable to apply bipolar RF energy to tissue. In some other versions, ring electrodes (128) cooperate with a ground pad (not shown) that is in contact with the skin of the patient to apply monopolar RF energy to tissue. In versions where tip (132) is configured to serve as an electrode, ring electrodes (128) cooperate with tip (132) to apply bipolar RF energy to tissue. While needle electrodes (140, 150) are all in the retracted position in this example, there may be usage scenarios where one or more needle electrodes (140, 150) are advanced distally while sheath (122) is in the retracted position shown in FIG. 7. In such scenarios, ring electrodes (128) may cooperate with one or more advanced needle electrodes (140, 150) to apply bipolar RF energy to tissue.

When needle electrodes (140, 150) are used to deliver RF energy to tissue, needle electrodes (140, 150) may be advanced into the tissue such that needle electrodes (140, 150) penetrate the tissue; then needle electrodes (140, 150) may be activated to apply the RF energy to the penetrated tissue. When tip (132) or ring electrodes (128) are used to deliver RF energy to tissue, tip (132) or ring electrodes (128) may be pressed against the tissue such that tip (132) or ring electrodes (128) engage the tissue; then tip (132) or ring electrodes (128) may be activated to apply the RF energy to the engaged tissue.

As indicated above, instrument (100) allows an operator to choose between applying RF energy to a surface of tissue (e.g., via tip (132) and/or ring electrodes (128)) and/or within penetrated tissue (e.g., via needle electrode (140) and/or needle electrodes (140, 150)). Thus, instrument (100) may be used to perform a relatively shallow ablation (e.g., via tip (132) and/or ring electrodes (128)), a relatively deep ablation (e.g., via needle electrode (140) and/or needle electrodes (140, 150)), or a volumetric ablation (e.g., via tip (132) and/or ring electrodes (128) in combination with needle electrode (140) and/or needle electrodes (140, 150)). By way of further example only, instrument (100) may be used to perform a vidian neuroectomy, a posterior nasal neurectomy, a turbinate reduction, or any other suitable procedure. In some cases, a combination of distal needle electrode (140) and tip (132) may be used to perform a turbinate reduction.

In some alternative uses, shaft assembly (120) may be pressed into tissue such that tip (132) penetrates the tissue to a certain depth. For instance, tip (132) may be inserted through an incision that was formed using another instrument; or tip (132) may be pressed with sufficient force to provide blunt dissection. In either case, tip (132) and/or ring electrodes (128) may be activated to apply RF energy to tissue when tip (132) and at least one ring electrode (128) has penetrated into tissue. Similarly, needle electrode (140) and/or needle electrodes (150) may be deployed after tip (132) has penetrated into tissue; and then needle electrode (140) and/or needle electrodes (150) may be activated to apply RF energy to the tissue. Other suitable ways in which needle electrodes (140, 150), tip (132), and/or ring electrodes (128) may be used to apply RF energy to tissue will be apparent to those skilled in the art in view of the teachings herein.

While not shown, instrument (100) may also include one or more position sensors that are operable to generate signals indicative of the position of end effector (130) in three-dimensional space. Such a position sensor may take the form of one or more coils that generate signals in response to the presence of an alternating magnetic field. The position data generated by such position signals may be processed by a system that provides a visual indication to the operator to show the operator where the end effector (130) is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein in its entirety; U.S. Pat. No. 7,720,521, entitled "Methods and Devices for Performing Procedures within the Ear, Nose, Throat and Paranasal Sinuses," issued May 18, 2010, the disclosure of which is incorporated by reference herein in its entirety; U.S. Pat. No. 10,463,242, entitled "Guidewire Navigation for Sinuplasty," issued Nov. 5, 2019, the disclosure of which is incorporated by reference herein in its entirety; and/or U.S. Pat. No. 10,561,370, entitled "Apparatus to Secure Field Generating Device to Chair," issued Feb. 18, 2020, the disclosure of which is incorporated by reference herein in its entirety.

III. ABLATION INSTRUMENT WITH TRANSVERSE LOOP ELECTRODE AND NEEDLE ELECTRODES

FIGS. 8A-12 show another example of an instrument (200) that may be used to deliver RF energy to tissue. For instance, instrument (200) may be used to ablate a nerve (e.g., the posterior nasal nerve (40)), ablate a turbinate (e.g., any of turbinates (20, 22, 24)), or ablate any other kind of anatomical structure in the head of a patient. Instrument (200) of this example includes a handle assembly (210), a shaft assembly (230), a loop electrode assembly (240), and an accessory (250). Instrument (200) is coupled with an RF generator (202), which is operable to generate RF electrosurgical energy for delivery to tissue via electrodes (242, 244, 270) as will be described in greater detail below. Instrument (200) may also be optionally coupled with an accessory driver (204), which may drive accessory (250) based on the form that accessory (250). Various examples of forms that accessory (250) may take will be described in greater detail below; while others will be apparent to those skilled in the art in view of the teachings herein.

Figure 8A:
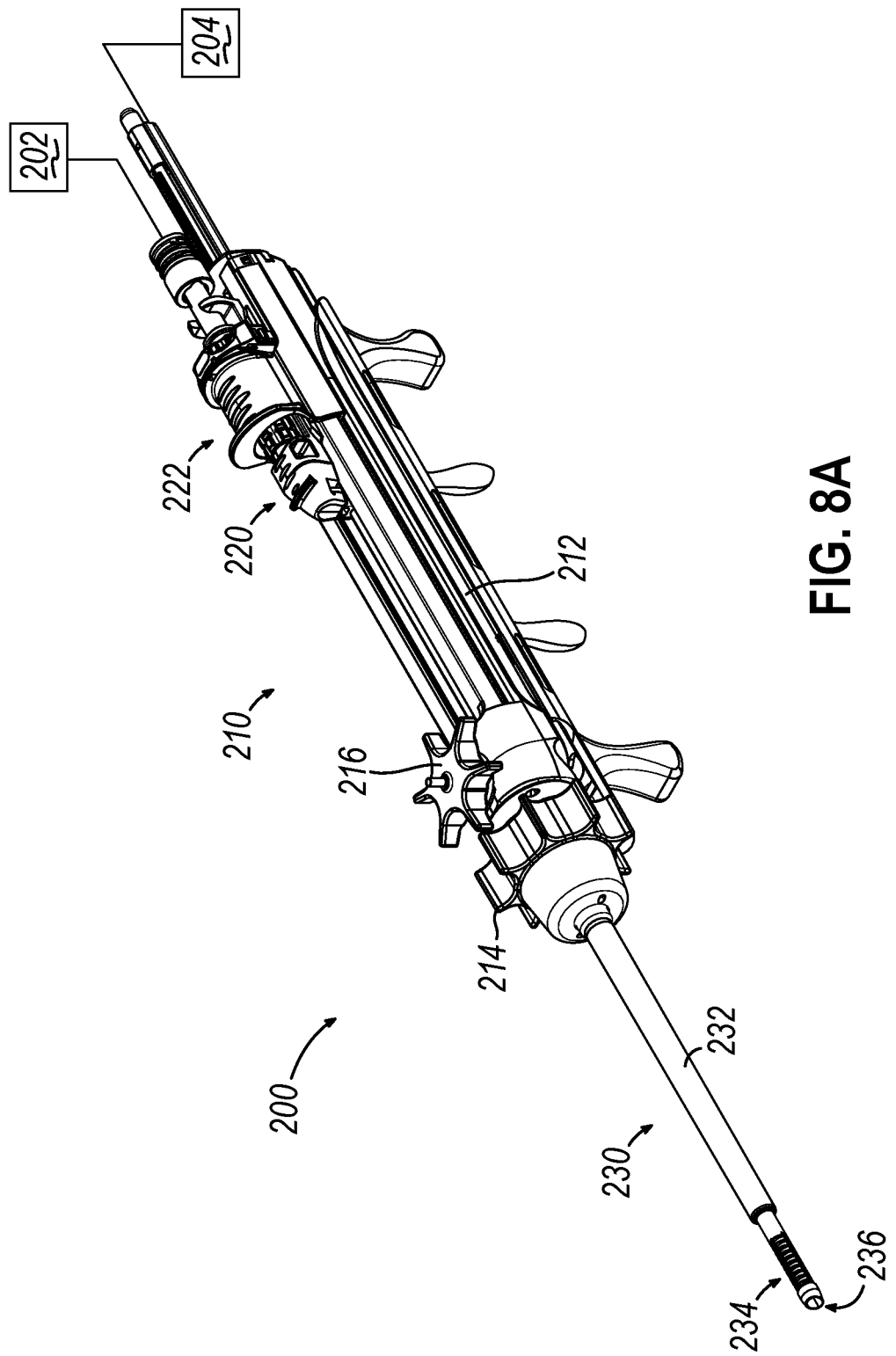
FIG. 8A depicts a perspective view of another example of an instrument that may be used to perform an ablation procedure in a nasal cavity, with a loop electrode in a retracted position, and with an accessory in a retracted position.
Figure 8B:
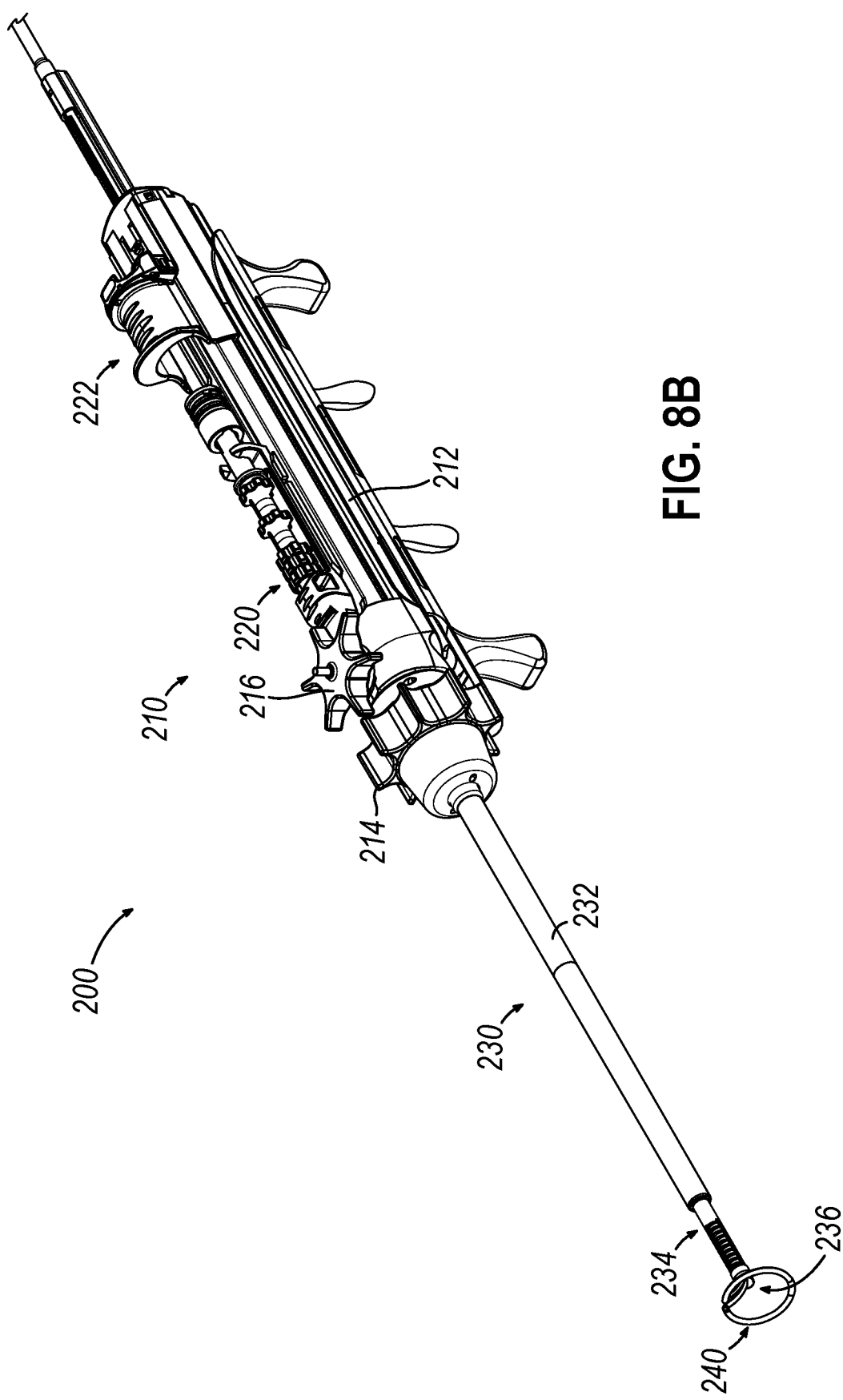
FIG. 8B depicts a perspective view of the instrument of FIG. 8A, with the loop electrode in an advanced position, and with the accessory in the retracted position.
Figure 8C:
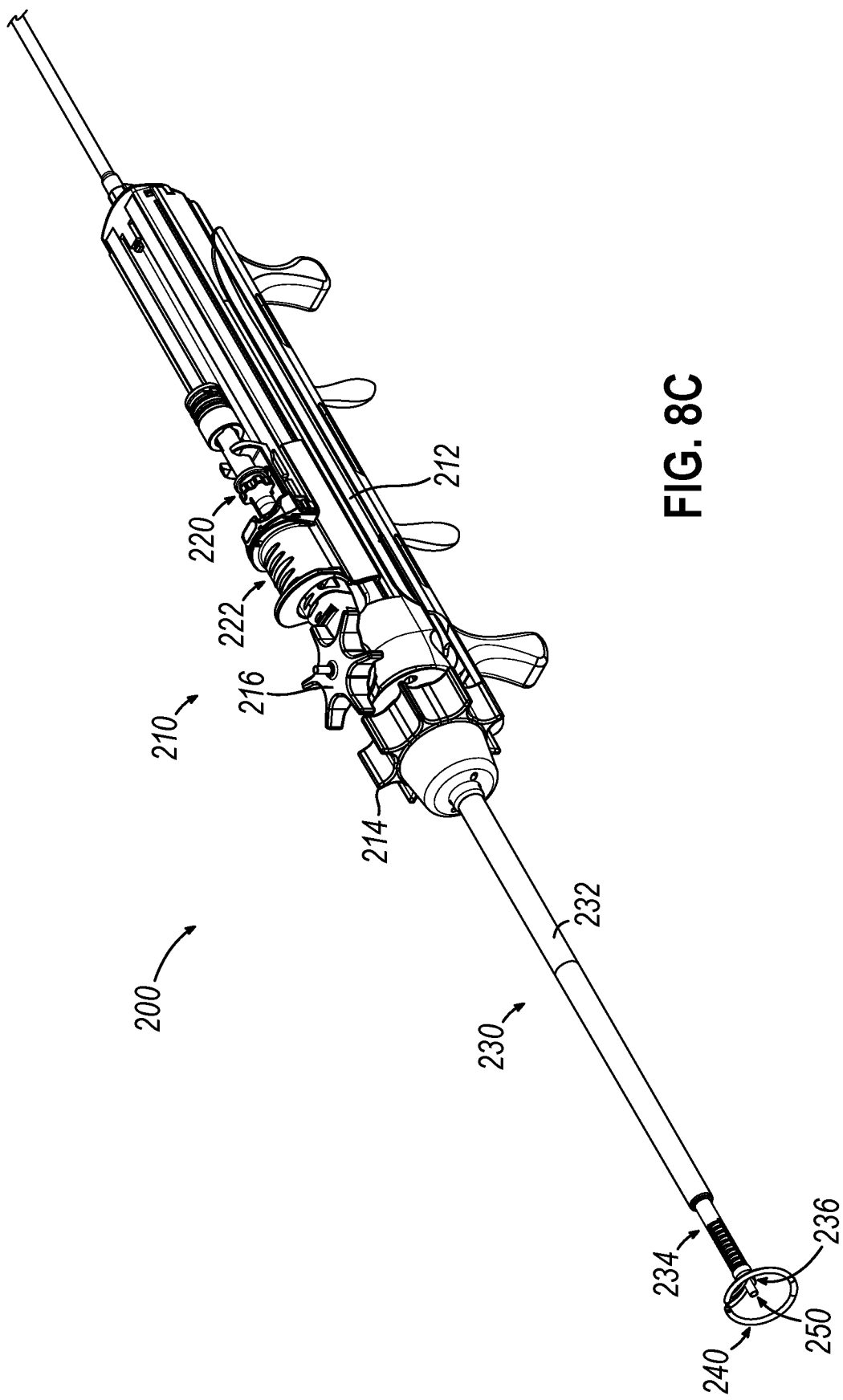
FIG. 8C depicts a perspective view of the instrument of FIG. 8A, with the loop electrode in an advanced position, and with the accessory in an advanced position.

Handle assembly (210) of this example includes a body (212), a first slider (220), and a second slider (222). Body (212) is sized and configured to be grasped and operated by a single hand of an operator, such as via a power grip, a pencil grip, or any other suitable kind of grip. Each slider (220, 222) is operable to translate longitudinally relative to body (212). Sliders (220, 222) are operable to translate independently relative to each other in some versions. Slider (220) is coupled with loop electrode assembly (240) and is thus operable to translate loop electrode assembly (240) longitudinally as will be described in greater detail below. The transition from FIG. 8A to FIG. 8B shows slider (220) driving loop electrode assembly (240) from a proximal position to a distal position. Slider (222) is coupled with accessory (250) and is thus operable to translate accessory (250) longitudinally as will be described in greater detail below. The transition from FIG. 8B to FIG. 8C shows slider (222) driving accessory (250) from a proximal position to a distal position.

Shaft assembly (230) of the present example includes a rigid portion (232), a flexible portion (234) distal to rigid portion (232), and an open distal end (236). A pull-wire (not shown) is coupled with flexible portion (234) and with a deflection control knob (216) of handle assembly (210). Deflection control knob (216) is rotatable relative to body (212), about an axis that is perpendicular to the longitudinal axis of shaft assembly (230), to selectively retract the pull-wire proximally. As the pull-wire is retracted proximally, flexible portion (234) bends and thereby deflects distal end (236) laterally away from the longitudinal axis of rigid portion (232). Deflection control knob (216), the pull-wire, and flexible portion (234) thus cooperate to impart steerability to shaft assembly (230). By way of example only, such steerability of shaft assembly (230) may be provided in accordance with at least some of the teachings of U.S. Pat. App. No. 63/028,609, entitled "Shaft Deflection Control Assembly for ENT Guide Instrument," filed May 22, 2020, the disclosure of which is incorporated by reference herein in its entirety. Other versions may provide some other kind of user input feature to drive steering of flexible portion (234), instead of deflection control knob (216). In some alternative versions, deflection control knob (216) is omitted, and flexible portion (234) is malleable. In still other versions, the entire length of shaft assembly (230) is rigid.

Shaft assembly (230) is also rotatable relative to handle assembly (210), about the longitudinal axis of rigid portion (232). Such rotation may be driven via rotation control knob (214), which is rotatably coupled with body (212) of handle assembly (210). Alternatively, shaft assembly (230) may be rotated via some other form of user input; or may be non-rotatable relative to handle assembly (210).

Figure 9:
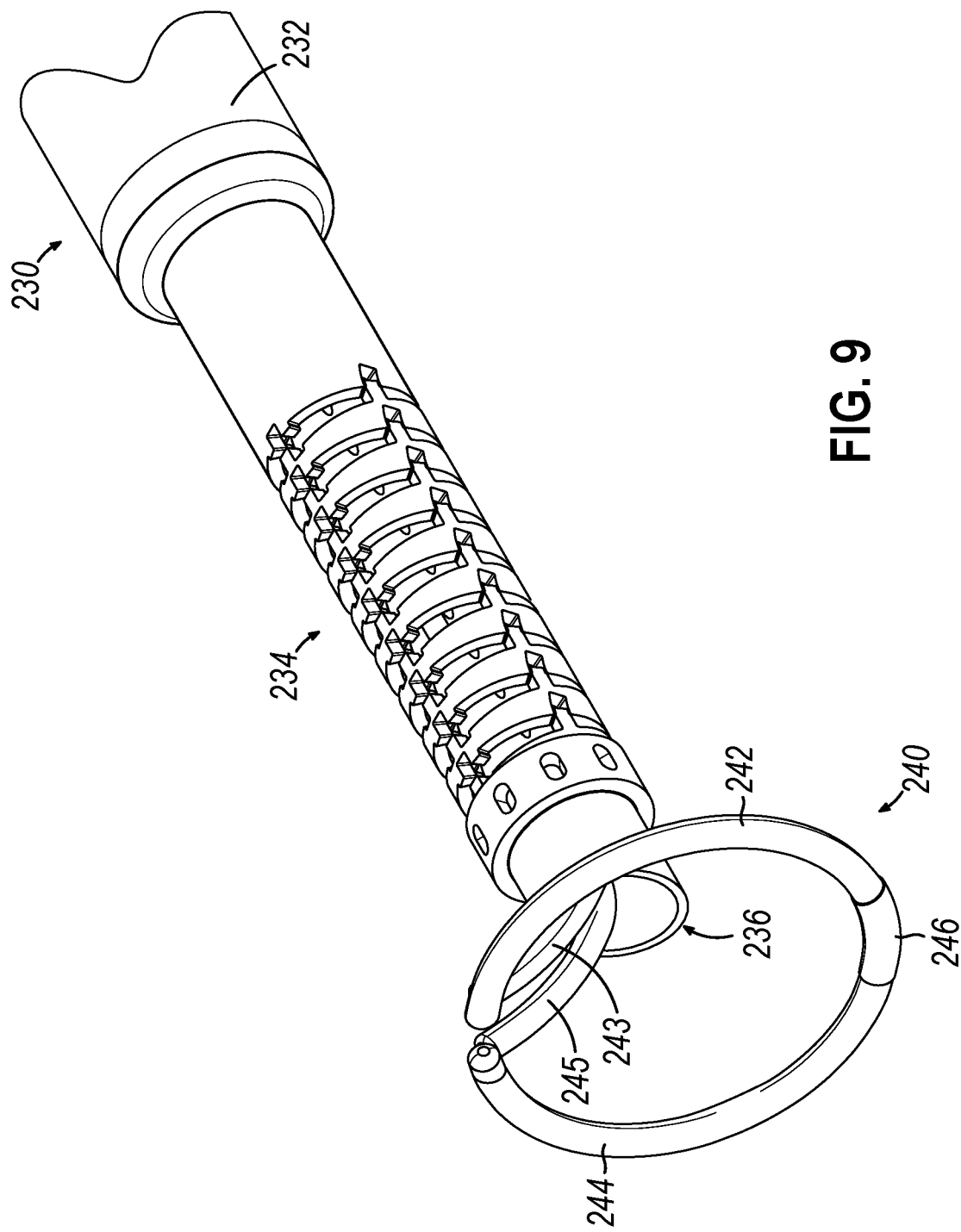
FIG. 9 depicts a perspective view of a distal portion of a shaft assembly of the instrument of FIG. 8A, with the loop electrode in the advanced position.

As best seen in FIG. 9, loop electrode assembly (240) of the present example includes a pair of arcuate arms (242, 244). One end of arcuate arm (242) is secured to a deployment arm (243); while the other end of arcuate arm (242) is secured to a junction (246). Similarly, one end of arcuate arm (244) is secured to a deployment arm (245); while the other end of arcuate arm (244) is secured to junction (246). In some versions, arcuate arm (242) and deployment arm (243) are unitarily formed from the same first metallic wire; while arcuate arm (244) and deployment arm (245) are unitarily formed from the same second metallic wire. Deployment arms (243, 245) extend along the length of shaft assembly (230) and are coupled with first slider (220). Each deployment arm (243, 245) may include an electrically insulative coating or sheath to prevent short circuiting within shaft assembly (230), with arcuate arms (242, 244) being left exposed to serve as electrodes. Each arcuate arm (242, 244) is coupled with a corresponding one or more wire(s) that electrically couple arcuate arms (242, 244) with RF generator (202). Arcuate arm (242) is configured to apply RF energy at a first polarity; while arcuate arm (244) is configured to apply RF energy at a second polarity. Arcuate arms (242, 244) thus serve as electrodes that are operable to apply bipolar RF energy to tissue contacting arcuate arms (242, 244). Junction (246) is formed of an electrically insulative material that prevents short circuiting between arcuate arms (242, 244) while mechanically securing the corresponding ends of arcuate arms (242, 244) together.

As shown in FIG. 9, arcuate arms (242, 244) are resiliently biased to define arcuate configurations when arcuate arms (242, 244) are exposed relative to distal end (236) of shaft assembly (230). By way of example only, arcuate arms (242, 244) may be formed of nitinol. In the present example, arcuate arms (242, 244) extend along a curve defined by a single radius. Arcuate arms (242, 244) and junction (246) thus cooperate to define a generally circular shape. In some other versions, arcuate arms (242, 244) and junction (246) cooperate to define a shape that is elliptical, oval-shaped, square, triangular, or otherwise non-circular. In the present example, the generally circular shape defined by arcuate arms (242, 244) and junction (246) extends along a plane that is perpendicular to the longitudinal axis of shaft assembly (230). In some other versions, the generally circular shape (or other non-circular shape) defined by arcuate arms (242, 244) and junction (246) extends along a plane that is obliquely oriented or otherwise transverse to the longitudinal axis of shaft assembly (230).

During use of loop electrode assembly (240), when loop electrode assembly (240) is fully deployed from distal end (236) of shaft assembly (230) as shown in FIG. 9, the operator may press loop electrode assembly (240) against the tissue that the operator wishes to ablate (or otherwise apply RF energy to), using a stamping type of motion. With the tissue adequately engaged by arcuate arms (242, 244), the operator may then activate RF generator (202), with arcuate arms (242, 244) serving as electrodes applying bipolar RF energy to the tissue against which loop electrode assembly (240) is pressed. This may provide ablation that is relatively shallow as compared to ablation provided via needle electrodes (140, 150) described above (or needle electrodes (270) described below).

Figure 10A:
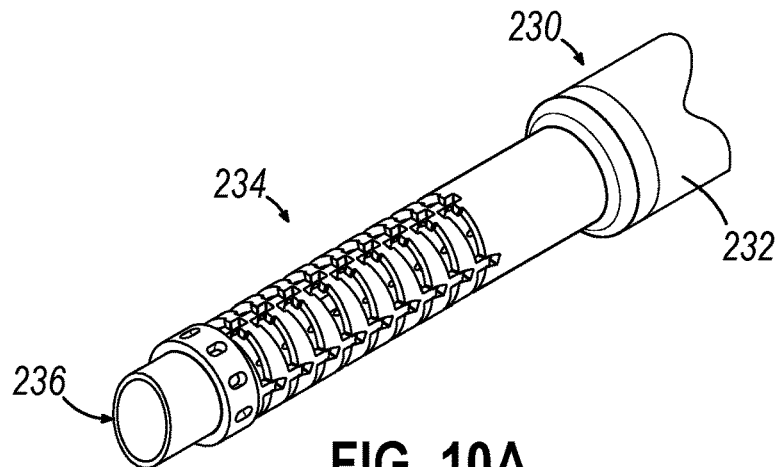
FIG. 10A depicts a perspective view of a distal portion of a shaft assembly of the instrument of FIG. 8A, with the loop electrode in the retracted position.
Figure 10B:
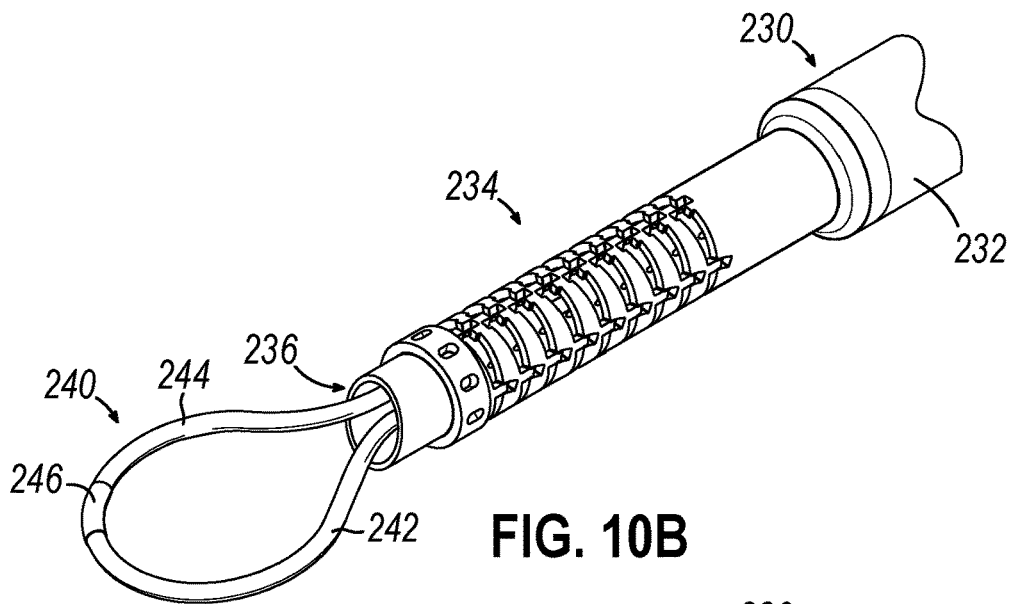
FIG. 10B depicts a perspective view of a distal portion of a shaft assembly of the instrument of FIG. 8A, with the loop electrode in a partially advanced position.
Figure 10C:
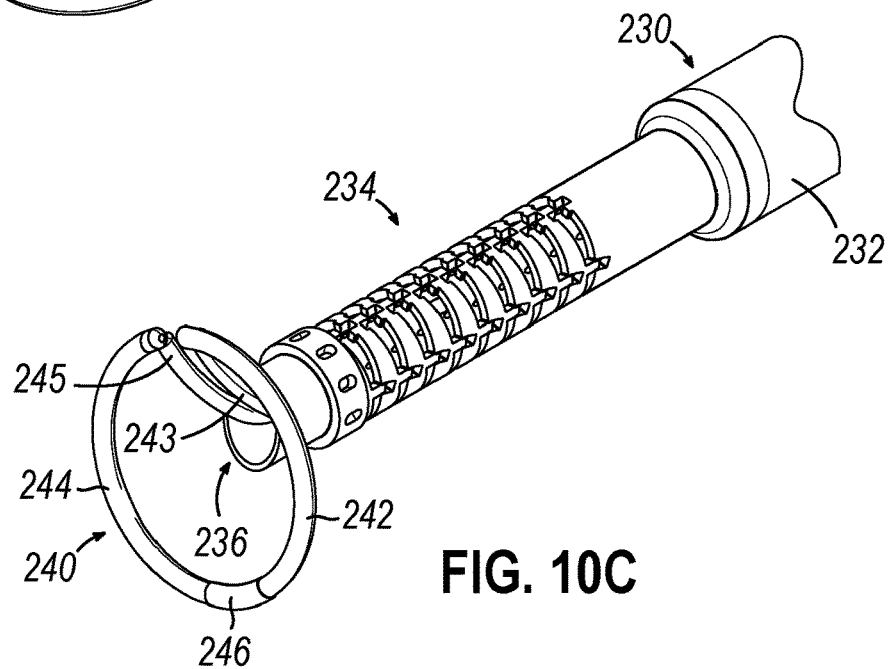
FIG. 10C depicts a perspective view of a distal portion of a shaft assembly of the instrument of FIG. 8A, with the loop electrode in the advanced position.

In some instances, an operator may wish to only partially deploy loop electrode assembly (240) from distal end (236) of shaft assembly (230). As shown in FIG. 10A, with first slider (220) in a proximal-most position, loop electrode assembly (240) may be fully contained within shaft assembly (230). When first slider (220) partially advanced distally to an intermediate longitudinal position, loop electrode assembly (240) may partially extend distally from distal end (236) of shaft assembly (230) as shown in FIG. 10B. In this state, the resilience of loop electrode assembly (240) may provide some degree of outward bowing of arcuate arms (242, 244), without arcuate arms (242, 244) defining a generally circular shape. The operator may nevertheless press arcuate arms (242, 244) against tissue when loop electrode assembly (240) is in a partially deployed state, such as the state shown in FIG. 10B, and then activate arcuate arms (242, 244) to apply RF energy to tissue. If the operator chooses to fully deploy loop electrode assembly (240) in addition to or in lieu of applying RF energy to tissue while loop electrode assembly (240) is in the partially deployed state shown in FIG. 10B, the operator may continued to advance first slider (220) to a distal position. With first slider (220) in a distal position, loop electrode assembly (240) may be fully deployed and thereby define the generally circular shape shown in FIG. 10C.

Figure 11:
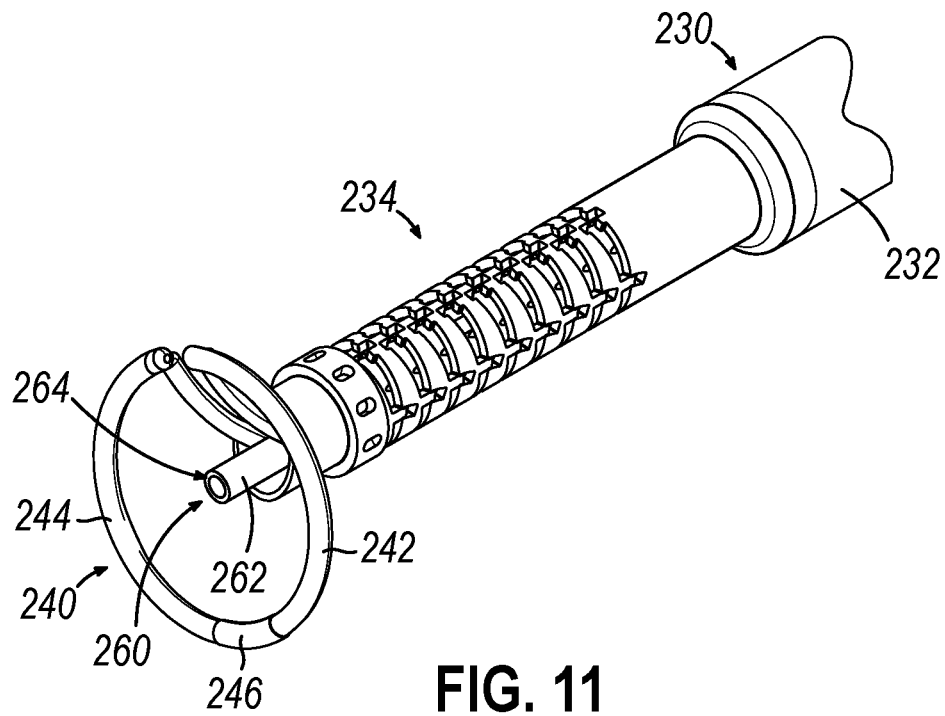
FIG. 11 depicts a perspective view of a distal portion of a shaft assembly of the instrument of FIG. 8A, with the loop electrode in the advanced position, and with an accessory in the form of a cannula in an advanced position.

As noted above, instrument (200) may include an accessory (250) that is coupled with second slider (222) and that is operable to translate relative to shaft assembly (230) and relative to loop electrode assembly (240). FIG. 11 shows one example of a form that accessory (250) may take. In this example, accessory (250) includes a cannula (260) having a shaft (262) with an open distal end (264). In the example shown in FIG. 11, cannula (260) is advanceable distally to a point where distal end (264) of cannula (260) is located at approximately the same longitudinal position as loop electrode assembly (240). In some other versions, cannula (260) is advanceable to a point that where distal end (264) of cannula (260) is located proximal to, or distal to, the longitudinal position of loop electrode assembly (240).

In some versions where accessory (250) includes a cannula (260), accessory driver (204) may include a source of saline, such that cannula (260) may be used to provide irrigation at the site where loop electrode assembly (240) is deployed. In some other versions where accessory (250) includes a cannula (260), accessory driver (204) may include a source of therapeutic agent, such that cannula (260) may be used to provide therapeutic agent at the site where loop electrode assembly (240) is deployed. In versions where cannula (260) is used to deliver therapeutic agent, loop electrode assembly (240) may be used to provide electroporation of tissue to thereby facilitate delivery of the therapeutic substances, etc. from cannula (260) to the tissue. In still other versions where accessory (250) includes a cannula (260), accessory driver (204) may include a source of suction, such that cannula (260) may be used to provide suction at the site where loop electrode assembly (240) is deployed. As yet another merely illustrative example, a guidewire or other element may be introduced to the site where loop electrode assembly (240) is deployed, via cannula (260). Other suitable ways in which cannula (260) may be used will be apparent to those skilled in the art.

Figure 12:
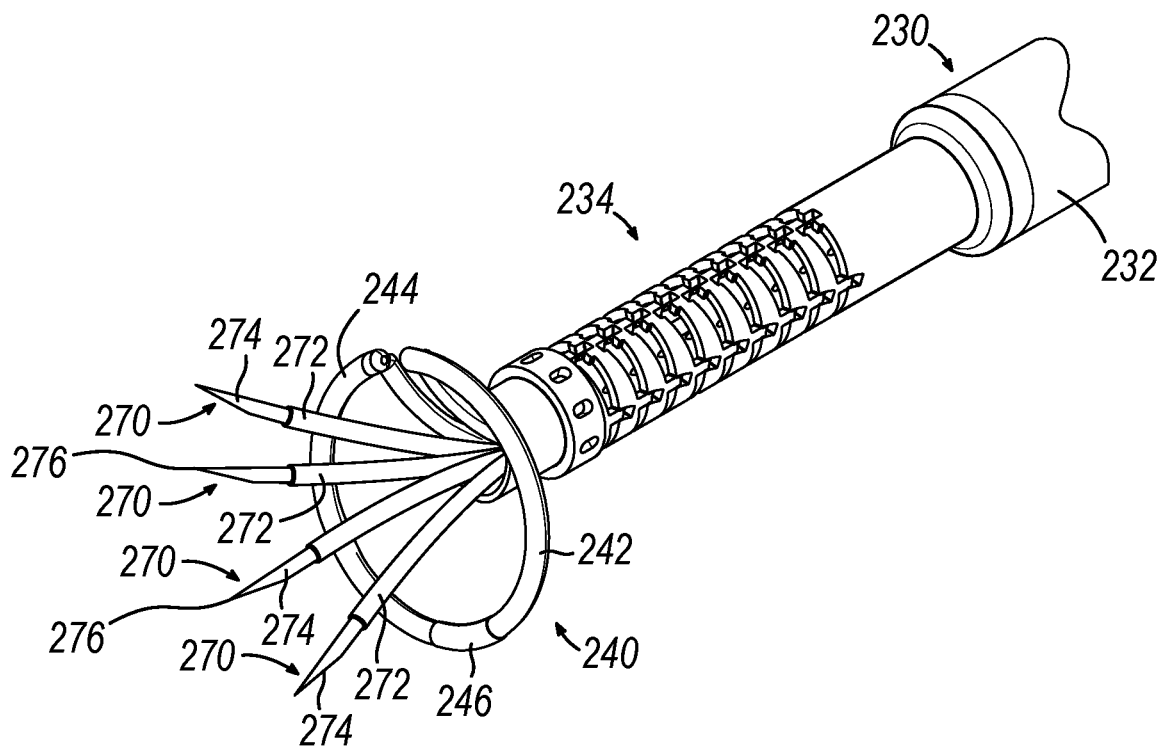
FIG. 12 depicts a perspective view of a distal portion of a shaft assembly of the instrument of FIG. 8A, with the loop electrode in the advanced position, and with an accessory in the form of a needle electrode set in an advanced position.

FIG. 12 shows another example of a form that accessory (250) may take. In this example, accessory (250) includes a bundle of needle electrodes (270). While four needle electrodes (270) are shown, any other suitable number of needle electrodes (270) may be provided. Each needle electrode (270) of this example includes an insulated proximal portion (272), an exposed distal portion (274), and a sharp tip (276). While needle electrodes (270) of the present example lack lumens, other versions of needle electrodes (270) may include lumens that allow needle electrodes (270) to deliver fluid (e.g., irrigation fluid, therapeutic agent, etc.) to tissue. When second slider (222) is advanced distally, needle electrodes (270) are driven to extend distally past the transverse plane defined by loop electrode assembly (240), as shown in FIG. 12. The operator may arrest distal advancement of second slider (222) at any suitable position along the length of body (212) of handle assembly (210) to achieve any suitable depth of penetration of needle electrodes (270) into tissue. In versions where accessory (250) is in the form of needle electrodes (270), accessory driver (204) includes an RF generator. Needle electrodes (270) are thus operable to apply RF energy to tissue in which exposed distal portions (274) are disposed.

In the present example, needle electrodes (270) are resiliently biased to splay outwardly relative to the longitudinal axis of shaft assembly (230) when needle electrodes (270) are distally positioned as shown in FIG. 12. In some versions, needle electrodes (270) are biased to extend along hyperbolic curves when needle electrodes (270) are advanced distally. In some other versions, needle electrodes (270) are biased to extend along a single-radius curvature when needle electrodes (270) are advanced distally. In addition to needle electrodes (270) being resiliently biased to splay outwardly, or as an alternative to needle electrodes (270) being resiliently biased to splay outwardly, the distal portion of shaft assembly (230) further includes guide features that promote the outward splaying of needle electrodes (270) as needle electrodes (270) are advanced distally out through distal end (236).

In some versions, all needle electrodes (270) have the same polarity. In such versions, needle electrodes (270) may cooperate with an electrode pad in contact with the skin of the patient to provide monopolar RF energy. In some other such versions, needle electrodes (270) may serve as active electrodes (or return electrodes) while loop electrode assembly (240) serves as a return electrode (or active electrode) to provide bipolar RF energy to tissue. As another variation, needle electrodes (270) may cooperate with each other to apply bipolar RF energy to tissue. For instance, two needle electrodes (270) may serve as active electrodes while the other two needle electrodes (270) may serve as return electrodes. In such versions, the two active needle electrodes (270) may be angularly spaced apart from each other by 180 degrees or may be spaced apart from each other by 90 degrees.

When needle electrodes (270) are used to deliver RF energy to tissue, needle electrodes (270) may be advanced into the tissue such that needle electrodes (270) penetrate the tissue; then needle electrodes (270) may be activated to apply the RF energy to the penetrated tissue. When loop electrode assembly (240) is used to deliver RF energy to tissue, loop electrode assembly (240) may be pressed against the tissue such that loop electrode assembly (240) engages the tissue; then loop electrode assembly (240) may be activated to apply the RF energy to the engaged tissue.

As indicated above, instrument (200) allows an operator to choose between applying RF energy to a surface of tissue (e.g., via loop electrode assembly (240)) and/or within penetrated tissue (e.g., via needle electrodes (270)). Thus, instrument (200) may be used to perform a relatively shallow ablation (e.g., via loop electrode assembly (240)), a relatively deep ablation (e.g., via needle electrodes (270)), or a volumetric ablation (e.g., loop electrode assembly (240) in combination with needle electrodes (270)). By way of further example only, instrument (200) may be used to perform a vidian neuroectomy, a posterior nasal neurectomy, a turbinate reduction, or any other suitable procedure. In some cases, a combination of loop electrode assembly (240) and needle electrodes (270) may be used to perform a turbinate reduction. Other suitable ways in which needle electrodes (270) and/or loop electrode assembly (240) may be used to apply RF energy to tissue will be apparent to those skilled in the art in view of the teachings herein.

While not shown, instrument (200) may also include one or more position sensors that are operable to generate signals indicative of the position of distal end (236), or some other component of instrument (200), in three-dimensional space. Such a position sensor may take the form of one or more coils that generate signals in response to the presence of an alternating magnetic field. The position data generated by such position signals may be processed by a system that provides a visual indication to the operator to show the operator where the distal end (236), or some other component of instrument (200), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

IV. ABLATION INSTRUMENT WITH DOUBLE AXIAL LOOP ELECTRODE ASSEMBLIES AND SINGLE NEEDLE ELECTRODE

Figure 13A:
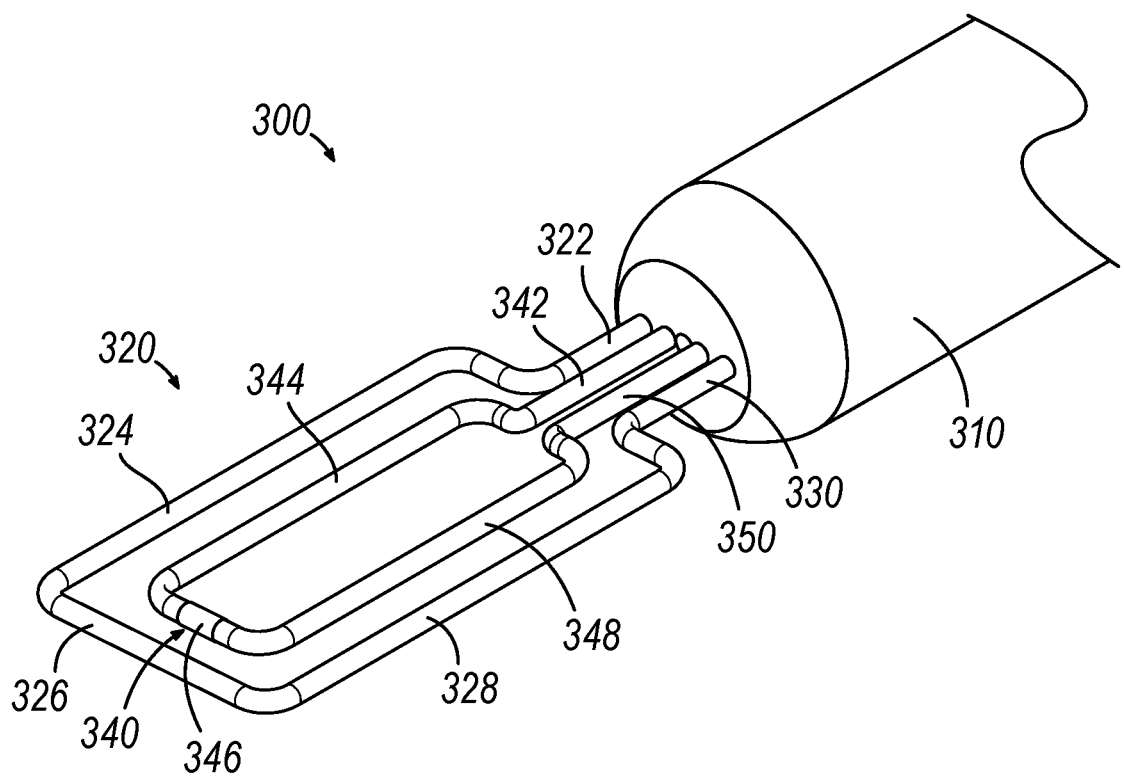
FIG. 13A depicts a perspective view of a distal portion of another example of an instrument that may be used to perform an ablation procedure in a nasal cavity, with a pair of loop electrodes, and with a needle electrode in a retracted position.
Figure 13B:
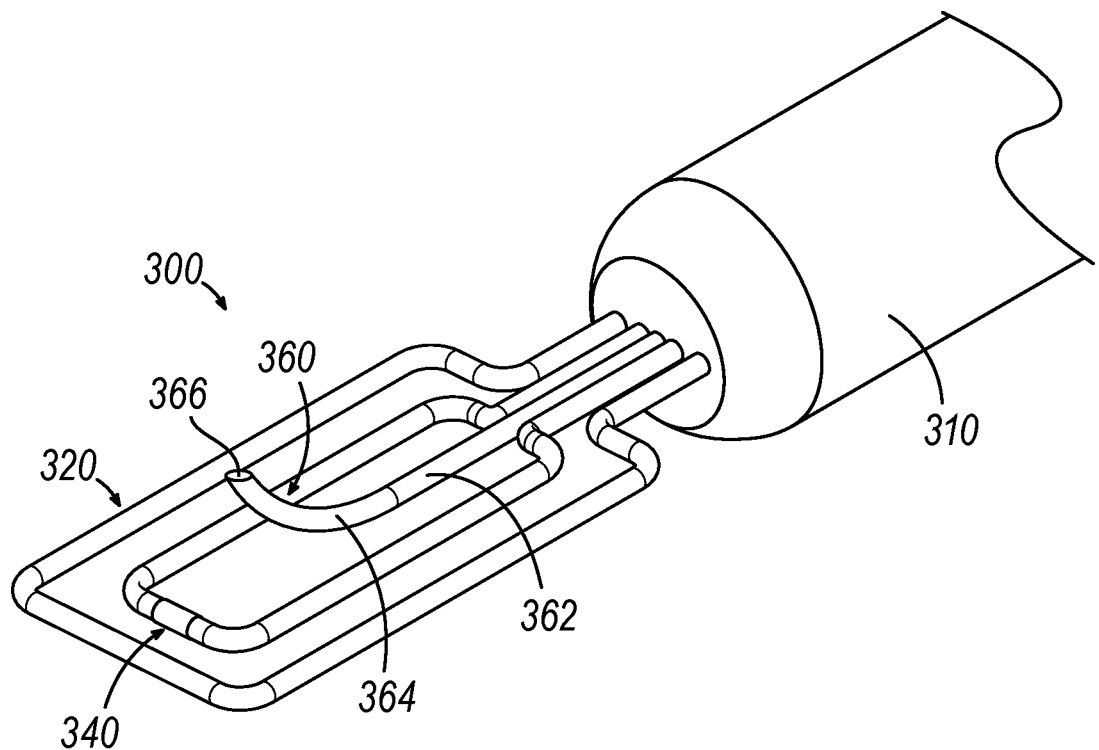
FIG. 13B depicts a perspective view of the distal portion of the instrument of FIG. 13A, with the needle electrode in an advanced position.
Figure 14:
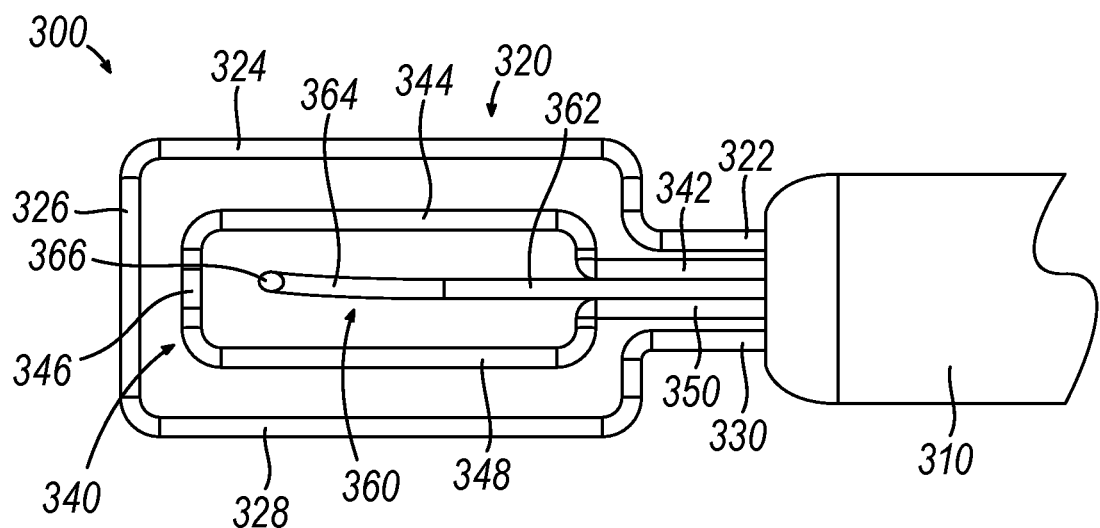
FIG. 14 depicts a top plan view of the distal portion of the instrument of FIG. 13A, with the needle electrode in the advanced position.
Figure 15:
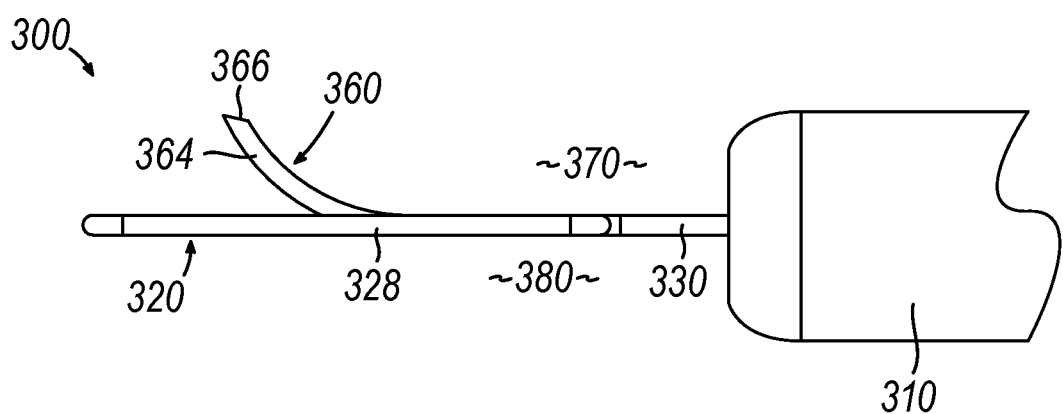
FIG. 15 depicts a side elevation view of the distal portion of the instrument of FIG. 13A, with the needle electrode in the advanced position.

FIGS. 13-15 show a distal portion of another example of an instrument (300) that may be used to deliver RF energy to tissue. For instance, instrument (300) may be used to ablate a nerve (e.g., the posterior nasal nerve (40)), ablate a turbinate (e.g., any of turbinates (20, 22, 24)), or ablate any other kind of anatomical structure in the head of a patient. Instrument (300) of this example includes a shaft (310), a first loop electrode assembly (320), a second loop electrode assembly (340), and a needle electrode (360). These features of instrument (300) may be readily incorporated into instrument (100) or instrument (200), as will be apparent to those skilled in the art in view of the teachings herein.

Loop electrode assemblies (320, 340) are coplanar with each other, extending along a plane that extends along dimensions that are aligned with and perpendicular to the longitudinal axis of shaft (310). First loop electrode assembly (320) is larger than second loop electrode assembly (340) and encompasses second loop electrode assembly (340). First loop electrode assembly (320) includes a first longitudinally extending segment (322) extending distally from the distal end of shaft (310), a second longitudinally extending segment (324) extending distally from first longitudinally extending segment (322) and laterally offset from first longitudinally extending segment (322), a distally positioned transversely extending segment (326), a third longitudinally extending segment (328) extending proximally from transversely extending segment (326), and a fourth longitudinally extending segment (330) extending from third longitudinally extending segment (328) into shaft (310) and laterally offset from third longitudinally extending segment (328).

In the present example, first loop electrode assembly (320) defines a generally rectangular shape, with segments (324, 326, 328) being substantially straight. Alternatively, first loop electrode assembly (320) may define a different shape in other versions. Moreover, while first loop electrode assembly (320) is symmetric about the longitudinal axis of shaft (310), first loop electrode assembly (320) may be asymmetric if desired. First loop electrode assembly (320) of the present example is also formed of a resilient material (e.g., nitinol, etc.), such that first loop electrode assembly (320) is resiliently biased to form the generally rectangular shape, though first loop electrode assembly (320) is configured to deform laterally, inwardly, and otherwise. For instance, first loop electrode assembly (320) may deform when first loop electrode assembly (320) is pressed against tissue, when first loop electrode assembly (320) is contained within a sheath, etc.

Second loop electrode assembly (340) is nested within the perimeter defined by first electrode assembly (320). Second electrode assembly (340) includes a first longitudinally extending segment (342) extending distally from the distal end of shaft (310), a second longitudinally extending segment (344) extending distally from first longitudinally extending segment (342) and laterally offset from first longitudinally extending segment (342), a distally positioned transversely extending segment (346), a third longitudinally extending segment (348) extending proximally from transversely extending segment (346), and a fourth longitudinally extending segment (350) extending from third longitudinally extending segment (348) into shaft (310) and laterally offset from third longitudinally extending segment (348).

In the present example, second loop electrode assembly (340) defines a generally rectangular shape, with segments (344, 346, 348) being substantially straight. Alternatively, second loop electrode assembly (340) may define a different shape in other versions. Moreover, while second loop electrode assembly (340) is symmetric about the longitudinal axis of shaft (310), second loop electrode assembly (340) may be asymmetric if desired. Second loop electrode assembly (340) of the present example is also formed of a resilient material (e.g., nitinol, etc.), such that second loop electrode assembly (340) is resiliently biased to form the generally rectangular shape, though second loop electrode assembly (340) is configured to deform laterally, inwardly, and otherwise. For instance, second loop electrode assembly (340) may deform when second loop electrode assembly (340) is pressed against tissue, when second loop electrode assembly (340) is contained within a sheath, etc.

Needle electrode (360) is nested within the perimeter defined by second electrode assembly (340). Needle electrode (360) includes a straight proximal portion (362), a curved distal portion (364), and a sharp distal tip (366). Needle electrode (360) is configured to penetrate tissue. In some versions, needle electrode (360) further includes a lumen and an opening at distal tip (366), such that needle electrode (360) may be used to deliver fluid (e.g., irrigation fluid, therapeutic agent, etc.) to tissue. In the present example, needle electrode (360) is formed of a resilient material (e.g., nitinol, etc.), such that needle electrode (360) is resiliently biased to form a curve at curved distal portion (364).

As shown in FIGS. 13A-13B, needle electrode (360) may be selectively advanced and retracted relative to shaft (310). Such advancement and retraction may be controlled by a sliding actuator like sliders (114, 116, 220, 222) described above or via any other suitable user input feature. In some variations, one or both of loop electrode assemblies (320, 340) may also be selectively advanced and retracted relative to shaft (310) by an actuator. Alternatively, needle electrode (360) and/or loop electrode assemblies (320, 340) may be longitudinally fixed relative to shaft (310). In such versions, needle electrode (360) and/or loop electrode assemblies (320, 340) may be selectively contained within, or exposed by, an outer sheath (not shown) that is slidably disposed relative to shaft (310). For instance, shaft (310) may slide longitudinally relative to such an outer sheath, or the outer sheath may slide longitudinally relative to shaft (310), to selectively contain or expose needle electrode (360) and/or loop electrode assemblies (320, 340). Regardless of how needle electrode (360) and/or loop electrode assemblies (320, 340) are advanced, retracted, contained, or exposed, the degree of advancement, retraction, containment, or exposure may be selected and adjusted in a manner similar to that described above with reference to FIGS. 10A-10C to thereby vary the degree of tissue contact.

Loop electrode assemblies (320, 340) and needle electrode (360) are operable to apply bipolar RF energy to tissue. In some versions, first loop electrode assembly (320) provides a first polarity of RF energy while second loop electrode assembly (340) provides a second polarity of RF energy. Needle electrode (360) may also provide either the first polarity of RF energy or the second polarity of RF energy. As another example, first loop electrode assembly (320) may itself be configured to apply bipolar RF energy to tissue. For instance, segments (324, 328) may be configured to provide a first polarity of RF energy while segment (326) may be configured to provide a second polarity of RF energy. In such versions, first loop electrode assembly (320) may include an electrically insulating material that provides electric isolation between segments (324, 326, 328). Similarly, second loop electrode assembly (340) may itself be configured to apply bipolar RF energy to tissue. For instance, segments (344, 348) may be configured to provide a first polarity of RF energy while segment (346) may be configured to provide a second polarity of RF energy. In such versions, second loop electrode assembly (340) may include an electrically insulating material that provides electric isolation between segments (344, 346, 348). In some versions where loop electrode assemblies (320, 340) are each operable to apply bipolar RF energy to tissue, segments (324, 328, 346) may be operable to apply a first polarity of RF energy while segments (326, 344, 348) are operable to apply a second polarity of RF energy.

Some versions of needle electrode (360) may itself also be configured to apply bipolar RF energy to tissue. For instance, different regions of needle electrode (360) may be electrically isolated from each other and may be operable to provide different polarities of RF energy. Other suitable ways in which polarities may be allocated among loop electrode assemblies (320, 340) and needle electrode (360) will be apparent to those skilled in the art in view of the teachings herein.

As shown in FIG. 15, needle electrode (360) protrudes into a first region (370) above loop electrode assemblies (320, 340). A second region (380) is defined on the opposite side of loop electrode assemblies (320, 340). In some versions, the portions of loop electrode assemblies (320, 340) and needle electrode (360) that face second region (380) are covered with an electrically insulating material; while the portions of loop electrode assemblies (320, 340) and needle electrode (360) that face first region (370) are left exposed. In such versions, loop electrode assemblies (320, 340) and needle electrode (360) may only apply RF energy to tissue that is located within the first region (370). By way of example only, approximately 30% to approximately 60% of the surface of loop electrode assemblies (320, 340) and needle electrode (360) that face second region (380) may be covered with insulating material. In other versions, the portions of loop electrode assemblies (320, 340) and needle electrode (360) that face second region (380) are left exposed, such that loop electrode assemblies (320, 340) and needle electrode (360) may apply RF energy to tissue that is located within the second region (380).

During use of instrument (300), the operator may press loop electrode assemblies (320, 340) against the tissue that the operator wishes to ablate (or otherwise apply RF energy to), using a stamping type of motion. With the tissue adequately engaged by loop electrode assemblies (320, 340), the operator may then activate RF generator (202), with loop electrode assemblies (320, 340) serving as electrodes applying bipolar RF energy to the tissue against which loop electrode assemblies (320, 340) are pressed. This may provide ablation that is relatively shallow. In scenarios where the operator wishes to provide a relatively deep ablation, the operator may advance needle electrode (360) into tissue and activate needle electrode (360) to apply RF energy to the tissue in which needle electrode (360) is disposed. In scenarios where the operator wishes to apply volumetric ablation, the operator may activate needle electrode (360) simultaneously with at least one loop electrode assembly (320, 340). By way of further example only, instrument (300) may be used to perform a vidian neuroectomy, a posterior nasal neurectomy, a turbinate reduction, or any other suitable procedure. In some cases, a combination of loop electrode assemblies (320, 340) and needle electrode (360) may be used to perform a turbinate reduction. Other suitable ways in which loop electrode assemblies (320, 340) and/or needle electrode (360) may be used to apply RF energy to tissue will be apparent to those skilled in the art in view of the teachings herein.

While not shown, instrument (300) may also include one or more position sensors that are operable to generate signals indicative of the position of loop electrode assemblies (320, 340) and/or needle electrode (360), or some other component of instrument (300), in three-dimensional space. Such a position sensor may further indicate the orientation of needle electrode (360), thereby assisting the operator in determining the location of regions (370, 380) in relation to loop electrode assemblies (320, 340) and needle electrode (360). Such a position sensor may take the form of one or more coils that generate signals in response to the presence of an alternating magnetic field. The position data generated by such position signals may be processed by a system that provides a visual indication to the operator to show the operator where loop electrode assemblies (320, 340) and/or needle electrode (360), or some other component of instrument (300), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

V. ABLATION INSTRUMENT WITH SINGLE AXIAL LOOP ELECTRODE ASSEMBLIES AND DOUBLE NEEDLE ELECTRODES

FIGS. 16A-18 show a distal portion of another example of an instrument (400) that may be used to deliver RF energy to tissue. For instance, instrument (400) may be used to ablate a nerve (e.g., the posterior nasal nerve (40)), ablate a turbinate (e.g., any of turbinates (20, 22, 24)), or ablate any other kind of anatomical structure in the head of a patient. Instrument (400) of this example includes a shaft (410), a loop electrode assembly (420), a first needle electrode (460), and a second needle electrode (470). These features of instrument (400) may be readily incorporated into instrument (100) or instrument (200), as will be apparent to those skilled in the art in view of the teachings herein.

Loop electrode assembly (420) extends along a plane that extends along dimensions that are aligned with and perpendicular to the longitudinal axis of shaft (410). Loop electrode assembly (420) includes a first longitudinally extending segment (422) extending distally from the distal end of shaft (410), a first arcuate segment (424) extending distally from first longitudinally extending segment (422), a distally positioned transversely extending segment (426), a second arcuate segment (428) extending proximally from transversely extending segment (426), and a fourth longitudinally extending segment (430) extending from second arcuate segment (428) into shaft (410).

In the present example, loop electrode assembly (420) defines a generally elliptical shape. Alternatively, loop electrode assembly (420) may define a different shape in other versions. Moreover, while loop electrode assembly (420) is symmetric about the longitudinal axis of shaft (410), loop electrode assembly (420) may be asymmetric if desired. Loop electrode assembly (420) of the present example is also formed of a resilient material (e.g., nitinol, etc.), such that loop electrode assembly (420) is resiliently biased to form the generally elliptical shape, though loop electrode assembly (420) is configured to deform laterally, inwardly, and otherwise. For instance, loop electrode assembly (420) may deform when loop electrode assembly (420) is pressed against tissue, when loop electrode assembly (420) is contained within a sheath, etc.

Needle electrodes (460, 470) are nested within the perimeter defined by loop electrode assembly (420). First needle electrode (460) includes a straight proximal portion (462), a curved distal portion (464), and a sharp distal tip (466). First needle electrode (460) is configured to penetrate tissue. In some versions, first needle electrode (460) further includes a lumen and an opening at distal tip (466), such that first needle electrode (460) may be used to deliver fluid (e.g., irrigation fluid, therapeutic agent, etc.) to tissue. In the present example, first needle electrode (460) is formed of a resilient material (e.g., nitinol, etc.), such that first needle electrode (460) is resiliently biased to form a curve at curved distal portion (464).

Second needle electrode (470) includes a straight proximal portion (472), a curved distal portion (474), and a sharp distal tip (476). In some versions, straight proximal portion (472) extends integrally from straight proximal portion (462) or curved distal portion (464) of first needle electrode (460). In some other versions, straight proximal portion (472) extends directly from the distal end of shaft (410). As another variation, a tubular element or other frame member may extend from the distal end of shaft (410) and may support needle electrodes (460, 470). Such a tubular element or other frame member may have lateral openings or other passageways from which needle electrodes (460, 470) may protrude transversely relative to the longitudinal axis of shaft (410). Other ways in which needle electrodes (460, 470) may be supported, guided, or otherwise engaged will be apparent to those skilled in the art in view of the teachings herein.

Like first needle electrode (460), second needle electrode (470) is configured to penetrate tissue. In some versions, second needle electrode (470) further includes a lumen and an opening at distal tip (476), such that second needle electrode (470) may be used to deliver fluid (e.g., irrigation fluid, therapeutic agent, etc.) to tissue. In the present example, second needle electrode (470) is formed of a resilient material (e.g., nitinol, etc.), such that first needle electrode (470) is resiliently biased to form a curve at curved distal portion (474).

Figure 16A:
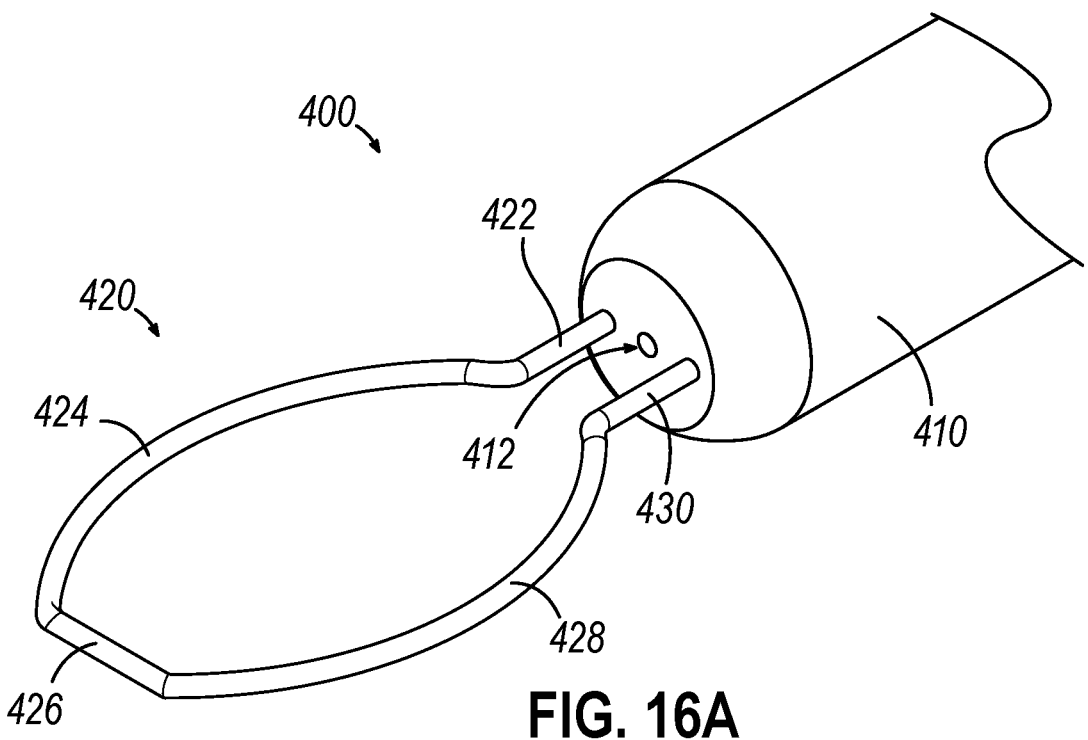
FIG. 16A depicts a perspective view of a distal portion of another example of an instrument that may be used to perform an ablation procedure in a nasal cavity, with a loop electrode, and with a pair of needle electrodes in a retracted position.
Figure 16B:
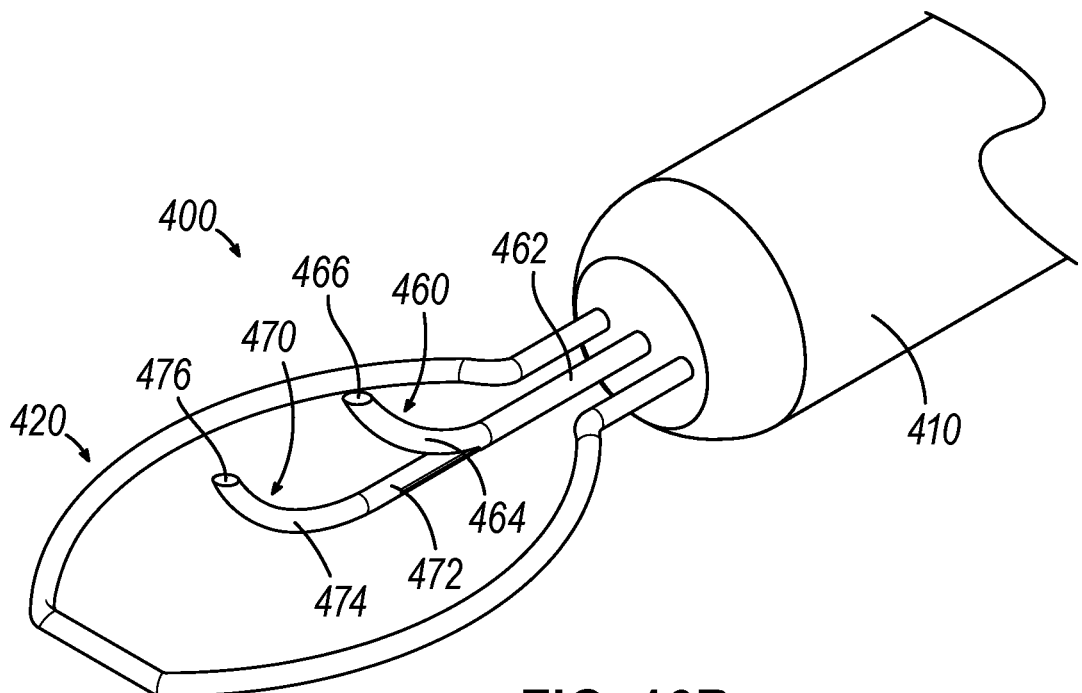
FIG. 16B depicts a perspective view of the distal portion of the instrument of FIG. 16A, with the needle electrodes in an advanced position.
Figure 17:
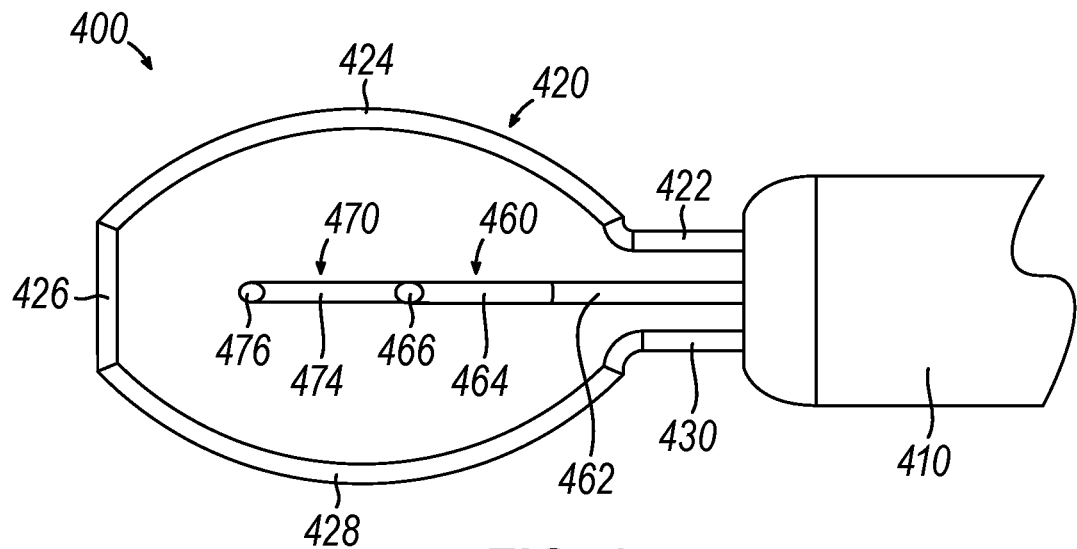
FIG. 17 depicts a top plan view of the distal portion of the instrument of FIG. 16A, with the needle electrodes in the advanced position.

As shown in FIGS. 136A-16B, needle electrodes (460, 470) may be selectively advanced and retracted relative to shaft (410) through a passageway (412) formed in shaft (410). Such advancement and retraction may be controlled by a sliding actuator like sliders (114, 116, 220, 222) described above or via any other suitable user input feature. In some variations, loop electrode assembly (420) may also be selectively advanced and retracted relative to shaft (410) by an actuator. Alternatively, needle electrodes (460, 470) and/or loop electrode assembly (420) may be longitudinally fixed relative to shaft (410). In such versions, needle electrodes (460, 470) and/or loop electrode assembly (420) may be selectively contained within, or exposed by, an outer sheath (not shown) that is slidably disposed relative to shaft (410). For instance, shaft (410) may slide longitudinally relative to such an outer sheath, or the outer sheath may slide longitudinally relative to shaft (410), to selectively contain or expose needle electrodes (460, 470) and/or loop electrode assembly (420). Regardless of how needle electrodes (460, 470) and/or loop electrode assembly (420) are advanced, retracted, contained, or exposed, the degree of advancement, retraction, containment, or exposure may be selected and adjusted in a manner similar to that described above with reference to FIGS. 10A-10C to thereby vary the degree of tissue contact.

Loop electrode assembly (420) and needle electrodes (460, 470) are operable to apply bipolar RF energy to tissue. In some versions, first arcuate segment (424) provides a first polarity of RF energy while arcuate segment (428) provides a second polarity of RF energy. In such versions, transversely extending segment (426) may include an electrically insulating material, such that transversely extending segment (426) provides structural support between arcuate segments (424, 428) without providing a path for short-circuiting between arcuate segments (424, 428). Needle electrode (460) may also provide either the first polarity of RF energy or the second polarity of RF energy; and needle electrode (470) may provide either the first polarity of RF energy or the second polarity of RF energy. As another example, first arcuate segment (424) and first needle electrode (460) may provide the first polarity of RF energy while second arcuate segment (428) and second needle electrode (470) provide the second polarity of RF energy. Other suitable ways in which polarities may be allocated among loop electrode assembly (420) and needle electrodes (460, 470) will be apparent to those skilled in the art in view of the teachings herein.

Figure 18:
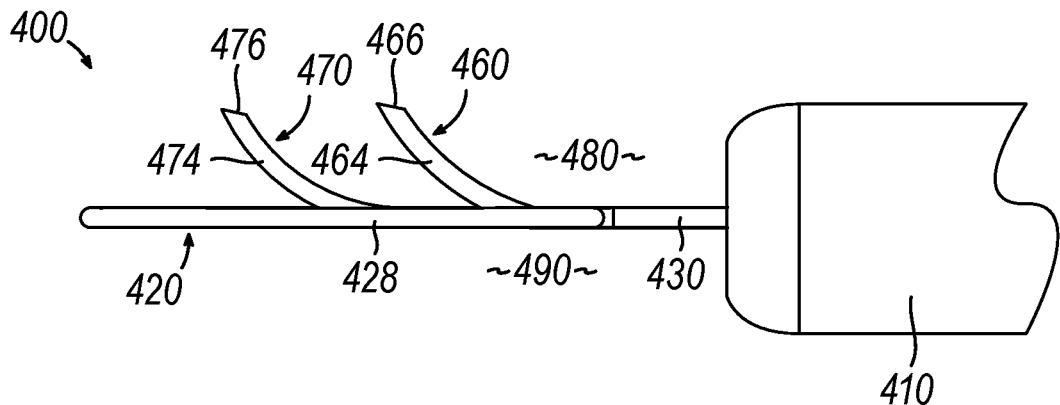
FIG. 18 depicts a side elevation view of the distal portion of the instrument of FIG. 16A, with the needle electrodes in the advanced position.

As shown in FIG. 18, needle electrodes (460, 470) protrude into a first region (480) above loop electrode assembly (420). A second region (490) is defined on the opposite side of loop electrode assembly (420). In some versions, the portions of loop electrode assembly (420) and needle electrodes (460, 470) that face second region (490) are covered with an electrically insulating material; while the portions of loop electrode assembly (420) and needle electrodes (460, 470) that face first region (480) are left exposed. In such versions, loop electrode assembly (420) and needle electrodes (460, 470) may only apply RF energy to tissue that is located within the first region (480). By way of example only, approximately 30% to approximately 60% of the surface of loop electrode assembly (420) and needle electrodes (460, 470) that face second region (490) may be covered with insulating material. In other versions, the portions of loop electrode assembly (420) and needle electrodes (460, 470) that face second region (490) are left exposed, such that loop electrode assembly (420) and needle electrodes (460, 470) may apply RF energy to tissue that is located within the second region (490).

During use of instrument (400), the operator may press loop electrode assembly (420) against the tissue that the operator wishes to ablate (or otherwise apply RF energy to), using a stamping type of motion. With the tissue adequately engaged by loop electrode assembly (420), the operator may then activate RF generator (202), with arcuate segments (424, 428) serving as electrodes applying bipolar RF energy to the tissue against which arcuate segments (424, 428) are pressed. This may provide ablation that is relatively shallow. In scenarios where the operator wishes to provide a relatively deep ablation, the operator may advance needle electrodes (460, 470) into tissue and activate needle electrodes (460, 470) to apply RF energy to the tissue in which needle electrodes (460, 470) are disposed. In scenarios where the operator wishes to apply volumetric ablation, the operator may activate needle electrodes (460, 470) simultaneously with loop electrode assembly (420). By way of further example only, instrument (400) may be used to perform a vidian neuroectomy, a posterior nasal neurectomy, a turbinate reduction, or any other suitable procedure. In some cases, a combination of needle electrodes (460, 470) and loop electrode assembly (420) may be used to perform a turbinate reduction. Other suitable ways in which loop electrode assembly (420) and/or needle electrodes (460, 470) may be used to apply RF energy to tissue will be apparent to those skilled in the art in view of the teachings herein.

While not shown, instrument (400) may also include one or more position sensors that are operable to generate signals indicative of the position of loop electrode assembly (420) and/or needle electrodes (460, 470), or some other component of instrument (300), in three-dimensional space. Such a position sensor may further indicate the orientation of needle electrodes (460, 470), thereby assisting the operator in determining the location of regions (480, 490) in relation to loop electrode assembly (420) and needle electrodes (460, 470). Such a position sensor may take the form of one or more coils that generate signals in response to the presence of an alternating magnetic field. The position data generated by such position signals may be processed by a system that provides a visual indication to the operator to show the operator where loop electrode assembly (420) and/or needle electrodes (460, 470), or some other component of instrument (400), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

VI. ABLATION INSTRUMENT WITH TRANSVERSE LOOP ELECTRODE AND LATERALLY OFFSET NEEDLE ELECTRODES

Figure 19A:
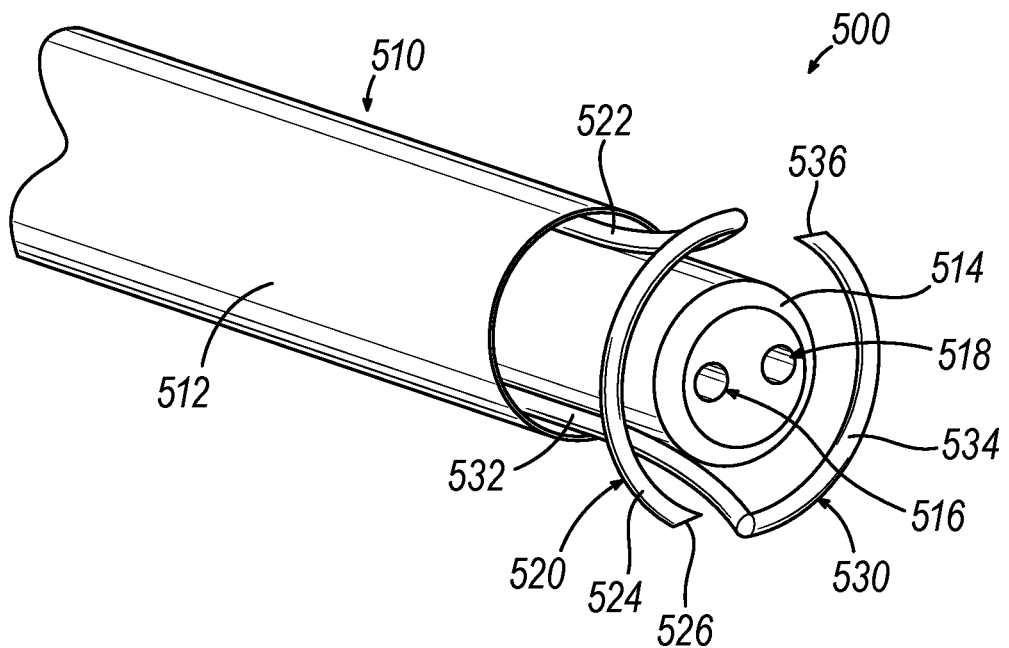
FIG. 19A depicts a perspective view of a distal portion of another example of an instrument that may be used to perform an ablation procedure in a nasal cavity, with a pair of transverse loop-forming electrodes, and with a pair of needle electrodes in a retracted position.
Figure 19B:
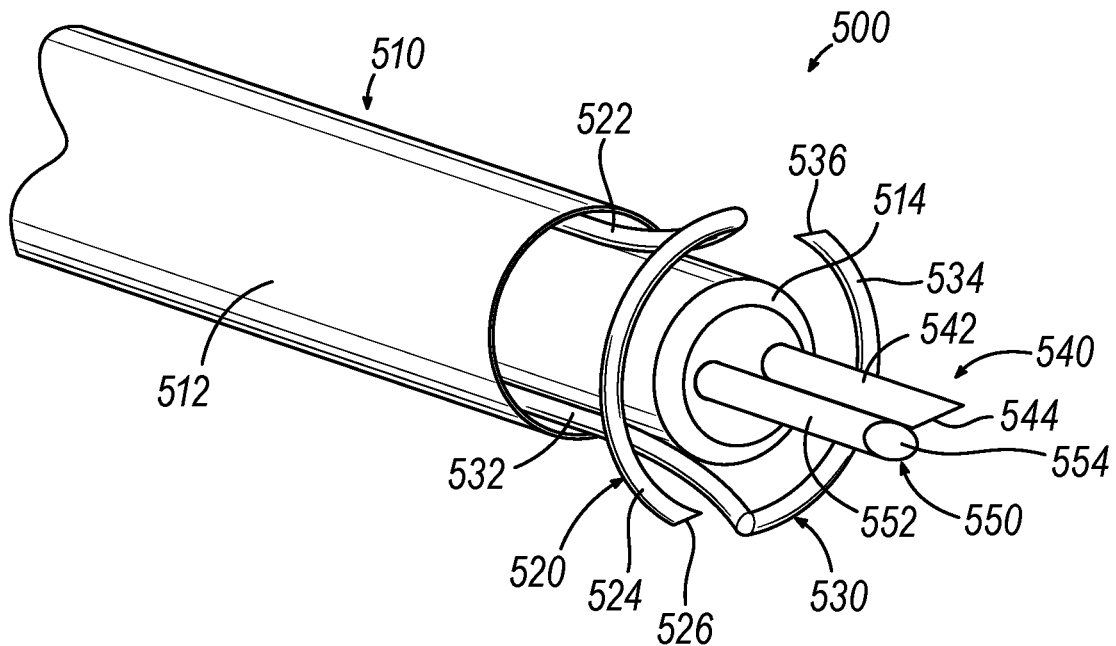
FIG. 19B depicts a perspective view of the distal portion of the instrument of FIG. 19A, with the needle electrodes in an advanced position.

FIGS. 19A-19B show a distal portion of another example of an instrument (500) that may be used to deliver RF energy to tissue. For instance, instrument (500) may be used to ablate a nerve (e.g., the posterior nasal nerve (40)), ablate a turbinate (e.g., any of turbinates (20, 22, 24)), or ablate any other kind of anatomical structure in the head of a patient. Instrument (500) of this example includes an outer sheath (512), an inner shaft (514), a first loop electrode segment (520), a second loop electrode segment (530), a first needle electrode (540), and a second needle electrode (550). These features of instrument (500) may be readily incorporated into instrument (100) or instrument (200), as will be apparent to those skilled in the art in view of the teachings herein.

Loop electrode segments (520, 530) are coplanar with each other, extending along a plane that is perpendicular to the longitudinal axis shared by sheath (512) and shaft (514). Loop electrode segment (520) includes a deployment arm (522), an arcuate arm (524), and a sharp tip (526). Deployment arm (522) extends along a space between sheath (512) and shaft (514). Arcuate arm (524) extends along a plane that is distal to the distal end of shaft (514), such that arcuate arm (524) is effectively distally spaced in relation to the distal end of shaft (514). Similarly, loop electrode segment (530) includes a deployment arm (532), an arcuate arm (534), and a sharp tip (536). Deployment arm (532) extends along a space between sheath (512) and shaft (514). Arcuate arm (534) extends along a plane that is distal to the distal end of shaft (514), such that arcuate arm (534) is effectively distally spaced in relation to the distal end of shaft (514).

In the present example, loop electrode segments (520, 530) together define a generally circular shape, though loop electrode segments (520, 530) do not contact each other. In other words, there is a slight gap between tip (526) and arcuate arm (534); and between tip (536) and arcuate arm (524). Alternatively, loop electrode segments (520, 530) may define any other suitable shape. Moreover, while loop electrode segments (520, 530) are symmetric with each other in the present example, loop electrode segments (520, 530) may be asymmetric in other versions. Each loop electrode segment (520, 530) of the present example is formed of a resilient material (e.g., nitinol, etc.), such that arcuate arms (524, 534) are resiliently biased to form the generally circular shape. Arcuate arms (524, 534) are nevertheless configured to deform to fit within the space between sheath (512) and shaft (514) when sheath (512) is distally positioned in relation to shaft (514) (e.g., during transit through the nasal cavity toward the target ablation site). Moreover, arcuate arms (524, 534) may deform when arcuate arms (524, 534) are pressed against tissue.

In some versions, each loop electrode segment (520, 530) further defines a lumen with an opening at tip (526, 536), such that loop electrode segments (520, 530) may be used to deliver fluid (e.g., irrigation fluid, therapeutic agent, etc.) to tissue. While tips (526, 536) are sharp in the present example, tips (526, 536) may instead be blunt or otherwise atraumatic in other versions.

Needle electrode (540) includes a shaft (542) and a sharp distal tip (544). As shown in FIGS. 19A-19B, needle electrode (540) is operable to be proximally retracted into, or advanced distally relative to, a passageway (518) within shaft (514). Needle electrode (550) includes a shaft (552) and a sharp distal tip (554). Needle electrode (550) is operable to be proximally retracted into, or advanced distally relative to, a passageway (518) within shaft (516). When needle electrodes (540, 550) are advanced fully distally, tips (544, 554) are positioned distally in relation to the transverse plane (i.e., circular shape) defined by arcuate arms (524, 534). In some versions, each needle electrode (540, 550) further defines a lumen with an opening at tip (544, 554), such that needle electrodes (540, 550) may be used to deliver fluid (e.g., irrigation fluid, therapeutic agent, etc.) to tissue. While needle electrodes (540, 550) are shown as being straight in this example, some versions of needle electrodes (540, 550) may be resiliently biased to splay outwardly or provide any other suitable configuration.

As noted above, some versions of instrument (500) provide longitudinal advancement and retraction of sheath (512) relative to shaft (514). Alternatively, shaft (514) may be operable to longitudinally advance and retract relative to sheath (512). In either case, such longitudinal movement may be driven by a sliding actuator like sliders (114, 116, 220, 222) described above or via any other suitable user input feature. Similarly, longitudinal movement of needle electrodes (540, 550) relative to shaft (514) may be driven by a sliding actuator like sliders (114, 116, 220, 222) described above or via any other suitable user input feature. In some versions, needle electrodes (540, 550) translate relative to shaft (514) simultaneously; while in others, needle electrodes (540, 550) translate relative to shaft (514) independently of each other. As yet another variation, some versions of instrument (500) may provide fixed longitudinal positioning of needle electrodes (540, 550) relative to shaft (514).

Loop electrode segments (520, 530) and needle electrodes (540, 550) are operable to apply bipolar RF energy to tissue. In some versions, first loop electrode segment (520) provides a first polarity of RF energy while second loop electrode segment (530) provides a second polarity of RF energy. Needle electrode (540) may also provide either the first polarity of RF energy or the second polarity of RF energy; and needle electrode (550) may provide either the first polarity of RF energy or the second polarity of RF energy. As another example, first loop electrode segment (520) and needle electrode (550) may provide the first polarity of RF energy while second electrode segment (530) and needle electrode (540) provide the second polarity of RF energy. Other suitable ways in which polarities may be allocated among loop electrode segments (520, 530) and needle electrodes (540, 550) will be apparent to those skilled in the art in view of the teachings herein.

During use of instrument (500), the operator may press arcuate arms (524, 534) against the tissue that the operator wishes to ablate (or otherwise apply RF energy to), using a stamping type of motion. With the tissue adequately engaged by arcuate arms (524, 534), the operator may then activate RF generator (202), with arcuate arms (524, 534) serving as electrodes applying bipolar RF energy to the tissue against which arcuate arms (524, 534) are pressed. This may provide ablation that is relatively shallow. In scenarios where the operator wishes to provide a relatively deep ablation, the operator may advance needle electrodes (540, 550) into tissue and activate needle electrodes (540, 550) to apply RF energy to the tissue in which needle electrodes (540, 550) are disposed. In scenarios where the operator wishes to apply volumetric ablation, the operator may activate needle electrodes (540, 550) simultaneously with at least one arcuate arm (524, 534). By way of further example only, instrument (500) may be used to perform a vidian neuroectomy, a posterior nasal neurectomy, a turbinate reduction, or any other suitable procedure. In some cases, a combination of arcuate arms (524, 534) and needle electrodes (540, 550) may be used to perform a turbinate reduction. Other suitable ways in which arcuate arms (524, 534) and/or needle electrodes (540, 550) may be used to apply RF energy to tissue will be apparent to those skilled in the art in view of the teachings herein.

While not shown, instrument (500) may also include one or more position sensors that are operable to generate signals indicative of the position of arcuate arms (524, 534) and/or needle electrodes (540, 550), or some other component of instrument (500), in three-dimensional space. Such a position sensor may take the form of one or more coils that generate signals in response to the presence of an alternating magnetic field. The position data generated by such position signals may be processed by a system that provides a visual indication to the operator to show the operator where arcuate arms (524, 534) and/or needle electrodes (540, 550), or some other component of instrument (500), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

VII. ABLATION INSTRUMENT WITH TRANSVERSE LOOP ELECTRODE AND LONGITUDINALLY OFFSET NEEDLE ELECTRODES

Figure 20A:
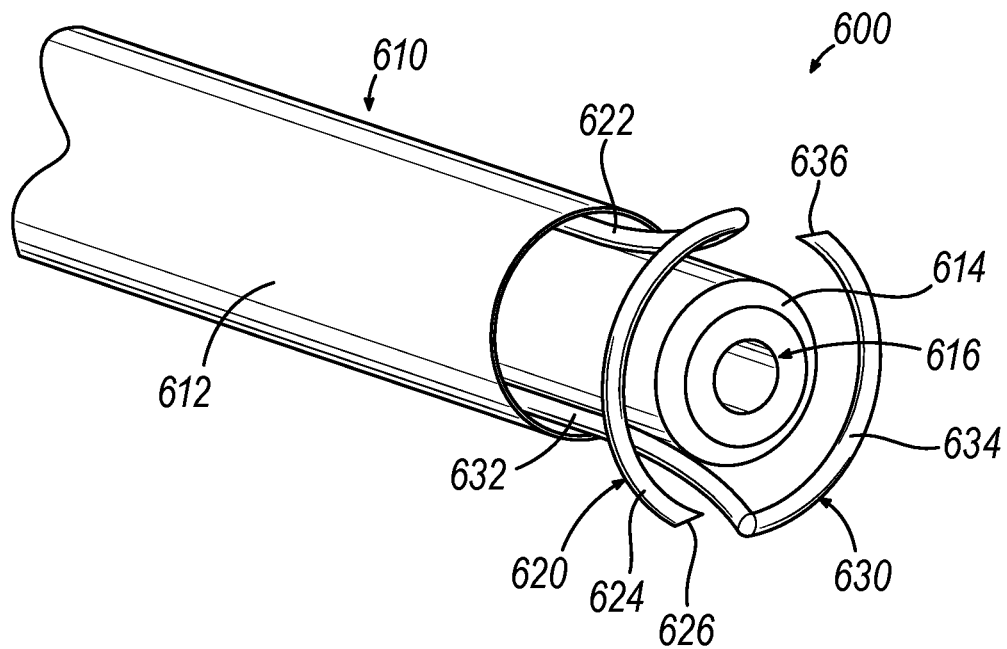
FIG. 20A depicts a perspective view of a distal portion of another example of an instrument that may be used to perform an ablation procedure in a nasal cavity, with a pair of transverse loop-forming electrodes, and with a needle electrode and ring electrode in a retracted position.
Figure 20B:
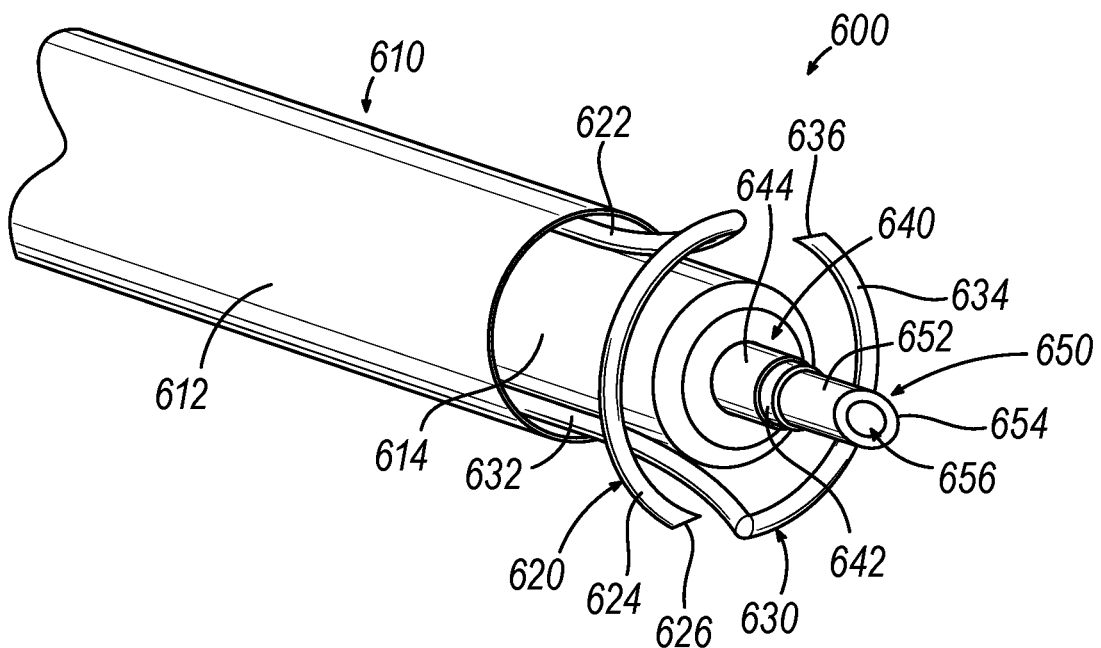
FIG. 20B depicts a perspective view of the distal portion of the instrument of FIG. 20A, with the needle electrode and ring electrode in an advanced position.

FIGS. 20A-20B show a distal portion of another example of an instrument (600) that may be used to deliver RF energy to tissue. For instance, instrument (600) may be used to ablate a nerve (e.g., the posterior nasal nerve (40)), ablate a turbinate (e.g., any of turbinates (20, 22, 24)), or ablate any other kind of anatomical structure in the head of a patient. Instrument (600) of this example includes an outer sheath (612), an inner shaft (614), a first loop electrode segment (620), a second loop electrode segment (630), and a needle electrode assembly (640). These features of instrument (300) may be readily incorporated into instrument (100) or instrument (200), as will be apparent to those skilled in the art in view of the teachings herein.

Loop electrode segments (620, 630) are coplanar with each other, extending along a plane that is perpendicular to the longitudinal axis shared by sheath (612) and shaft (614). Loop electrode segment (620) includes a deployment arm (622), an arcuate arm (624), and a sharp tip (626). Deployment arm (622) extends along a space between sheath (612) and shaft (614). Arcuate arm (624) extends along a plane that is distal to the distal end of shaft (614), such that arcuate arm (624) is effectively distally spaced in relation to the distal end of shaft (614). Similarly, loop electrode segment (630) includes a deployment arm (632), an arcuate arm (634), and a sharp tip (636). Deployment arm (632) extends along a space between sheath (612) and shaft (614). Arcuate arm (634) extends along a plane that is distal to the distal end of shaft (614), such that arcuate arm (634) is effectively distally spaced in relation to the distal end of shaft (614).

In the present example, loop electrode segments (620, 630) together define a generally circular shape, though loop electrode segments (620, 630) do not contact each other. In other words, there is a slight gap between tip (626) and arcuate arm (634); and between tip (636) and arcuate arm (624). Alternatively, loop electrode segments (620, 630) may define any other suitable shape. Moreover, while loop electrode segments (620, 630) are symmetric with each other in the present example, loop electrode segments (620, 630) may be asymmetric in other versions. Each loop electrode segment (620, 630) of the present example is formed of a resilient material (e.g., nitinol, etc.), such that arcuate arms (624, 634) are resiliently biased to form the generally circular shape. Arcuate arms (624, 634) are nevertheless configured to deform to fit within the space between sheath (612) and shaft (614) when sheath (612) is distally positioned in relation to shaft (614) (e.g., during transit through the nasal cavity toward the target ablation site). Moreover, arcuate arms (624, 634) may deform when arcuate arms (624, 634) are pressed against tissue.

In some versions, each loop electrode segment (620, 630) further defines a lumen with an opening at tip (626, 636), such that loop electrode segments (620, 630) may be used to deliver fluid (e.g., irrigation fluid, therapeutic agent, etc.) to tissue. While tips (626, 636) are sharp in the present example, tips (626, 636) may instead be blunt or otherwise atraumatic in other versions.

Needle electrode assembly (640) includes a shaft (642) with a ring electrode (644) secured coaxially to shaft (642); and a needle electrode (650) extending distally from shaft (642). Needle electrode (650) includes a needle shaft (652) with a sharp distal tip (654) and a lumen (656) extending to an opening at tip (654). Needle electrode (650) may be used to deliver fluid (e.g., irrigation fluid, therapeutic substance, etc.) to tissue via lumen (656). Alternatively, lumen (656) may be omitted in some versions. As shown in FIGS. 20A-20B, needle electrode assembly (640) is operable to be proximally retracted into, or advanced distally relative to, a passageway (616) within shaft (614). When needle electrode assembly (640) is advanced fully distally, electrodes (644, 650) are positioned distally in relation to the transverse plane (i.e., circular shape) defined by arcuate arms (624, 634). While needle electrode assembly (640) is shown as being straight in this example, some versions of needle electrode assembly (640) may be resiliently biased to deflect laterally outwardly or provide any other suitable configuration.

As noted above, some versions of instrument (600) provide longitudinal advancement and retraction of sheath (612) relative to shaft (614). Alternatively, shaft (614) may be operable to longitudinally advance and retract relative to sheath (612). In either case, such longitudinal movement may be driven by a sliding actuator like sliders (114, 116, 220, 222) described above or via any other suitable user input feature. Similarly, longitudinal movement of needle electrode assembly (640) relative to shaft (614) may be driven by a sliding actuator like sliders (114, 116, 220, 222) described above or via any other suitable user input feature. In some versions, shafts (642, 652) translate relative to shaft (614) simultaneously; while in others, shafts (642, 652) translate relative to shaft (614) independently of each other. As yet another variation, some versions of instrument (600) may provide fixed longitudinal positioning of needle electrode assembly (640) relative to shaft (614).

Loop electrode segments (620, 630) and electrodes (644, 650) are operable to apply bipolar RF energy to tissue. In some versions, first loop electrode segment (620) provides a first polarity of RF energy while second loop electrode segment (630) provides a second polarity of RF energy. Ring electrode (644) may also provide either the first polarity of RF energy or the second polarity of RF energy; and needle electrode (650) may provide either the first polarity of RF energy or the second polarity of RF energy. As another example, first loop electrode segment (620) and ring electrode (644) may provide the first polarity of RF energy while second electrode segment (630) and needle electrode (650) provide the second polarity of RF energy. Other suitable ways in which polarities may be allocated among loop electrode segments (620, 630) and electrodes (644, 650) will be apparent to those skilled in the art in view of the teachings herein.

During use of instrument (600), the operator may press arcuate arms (624, 634) against the tissue that the operator wishes to ablate (or otherwise apply RF energy to), using a stamping type of motion. With the tissue adequately engaged by arcuate arms (624, 634), the operator may then activate RF generator (202), with arcuate arms (624, 634) serving as electrodes applying bipolar RF energy to the tissue against which arcuate arms (624, 634) are pressed. This may provide ablation that is relatively shallow. In scenarios where the operator wishes to provide a relatively deep ablation, the operator may advance needle electrode assembly (640) into tissue and activate electrodes (644, 650) to apply RF energy to the tissue in which needle electrode assembly (640) is disposed. In scenarios where the operator wishes to apply volumetric ablation, the operator may activate electrodes (644, 650) simultaneously with at least one arcuate arm (624, 634). By way of further example only, instrument (600) may be used to perform a vidian neuroectomy, a posterior nasal neurectomy, a turbinate reduction, or any other suitable procedure. In some cases, a combination of arcuate arms (624, 634) and electrodes (644, 650) may be used to perform a turbinate reduction. Other suitable ways in which arcuate arms (624, 634) and/or needle electrode assembly (640) may be used to apply RF energy to tissue will be apparent to those skilled in the art in view of the teachings herein.

While not shown, instrument (600) may also include one or more position sensors that are operable to generate signals indicative of the position of arcuate arms (624, 634) and/or needle electrode assembly (640), or some other component of instrument (600), in three-dimensional space. Such a position sensor may take the form of one or more coils that generate signals in response to the presence of an alternating magnetic field. The position data generated by such position signals may be processed by a system that provides a visual indication to the operator to show the operator where arcuate arms (624, 634) and/or needle electrode assembly (640), or some other component of instrument (600), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein

VIII. EXAMPLE OF RF ABLATION INSTRUMENT WITH LOOP ELECTRODE ASSEMBLY AND NEEDLE ELECTRODES

Figure 21:
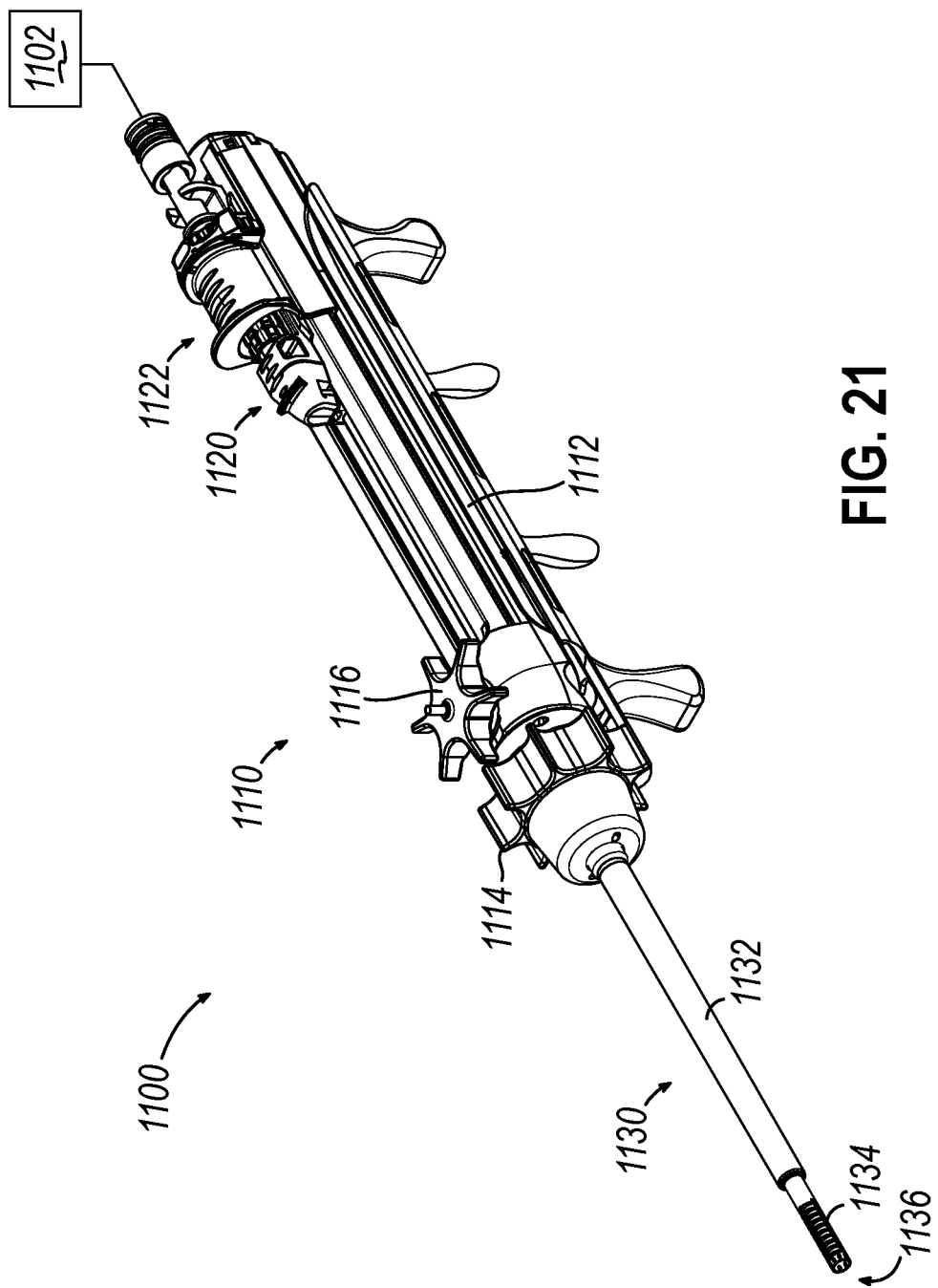
FIG. 21 depicts a perspective view of an example of an instrument that may be used to perform an ablation procedure in a nasal cavity, with a loop electrode assembly of the instrument in a proximal retracted position relative to a shaft assembly of the instrument, and with a pair of needle electrodes of the instrument in a proximal retracted position relative to the shaft assembly.
Figure 22A:
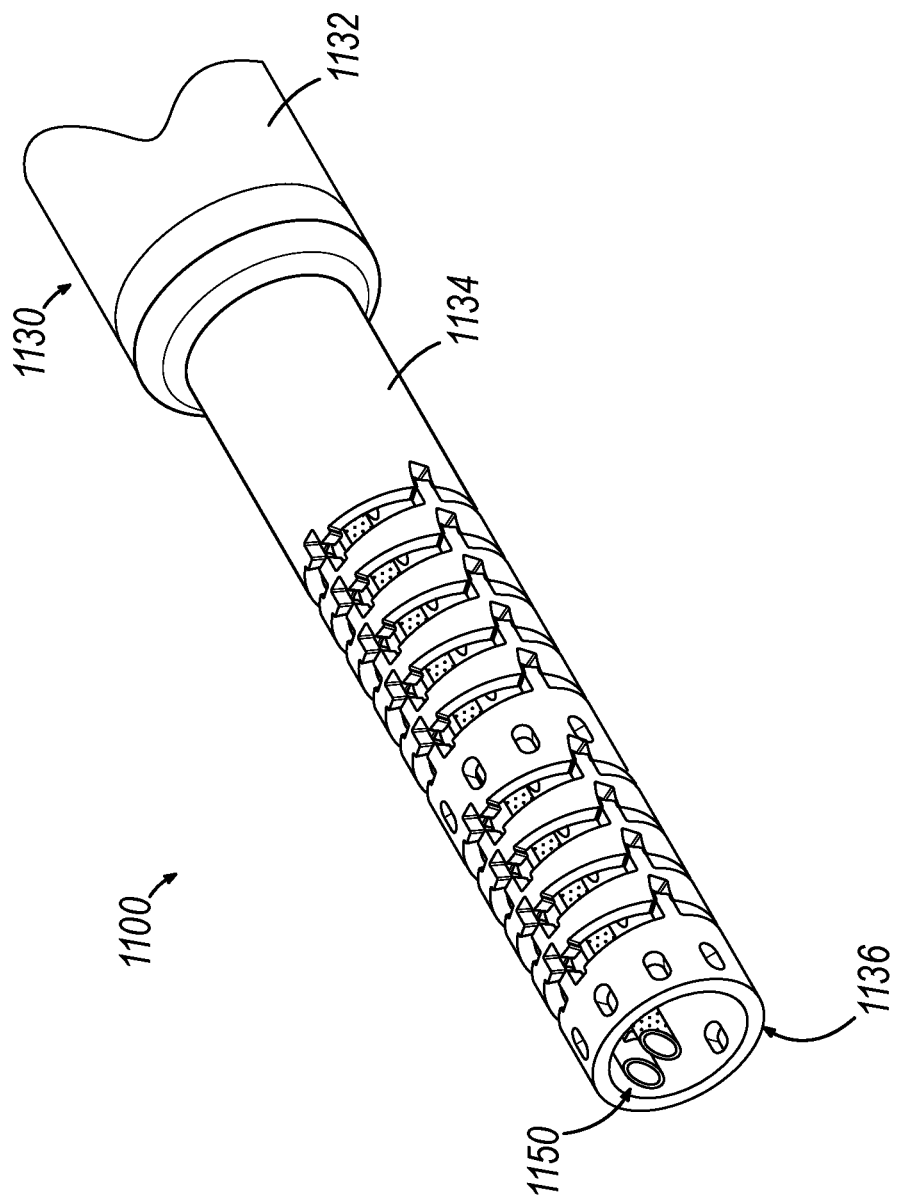
FIG. 22A depicts a perspective view of a distal portion of the shaft assembly of the instrument of FIG. 21, with the loop electrode assembly in the proximal retracted position relative to the shaft assembly, and with the pair of needle electrodes in the proximal retracted position relative to the shaft assembly.
Figure 22B:
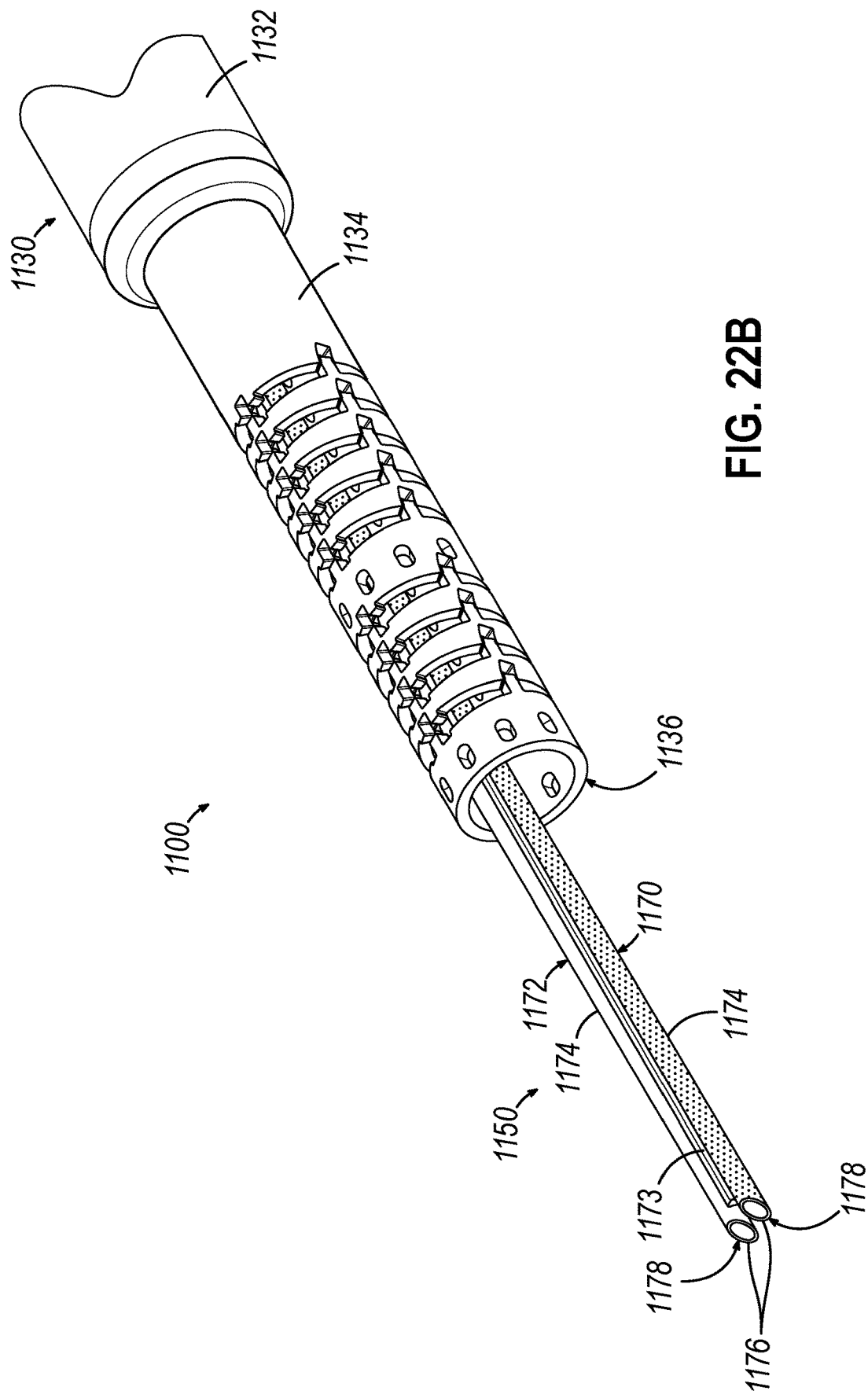
FIG. 22B depicts a perspective view of the distal portion of the shaft assembly of the instrument of FIG. 21, with the loop electrode assembly in the proximal retracted position relative to the shaft assembly, and with the pair of needle electrodes in a distal extended position relative to the shaft assembly.
Figure 22C:
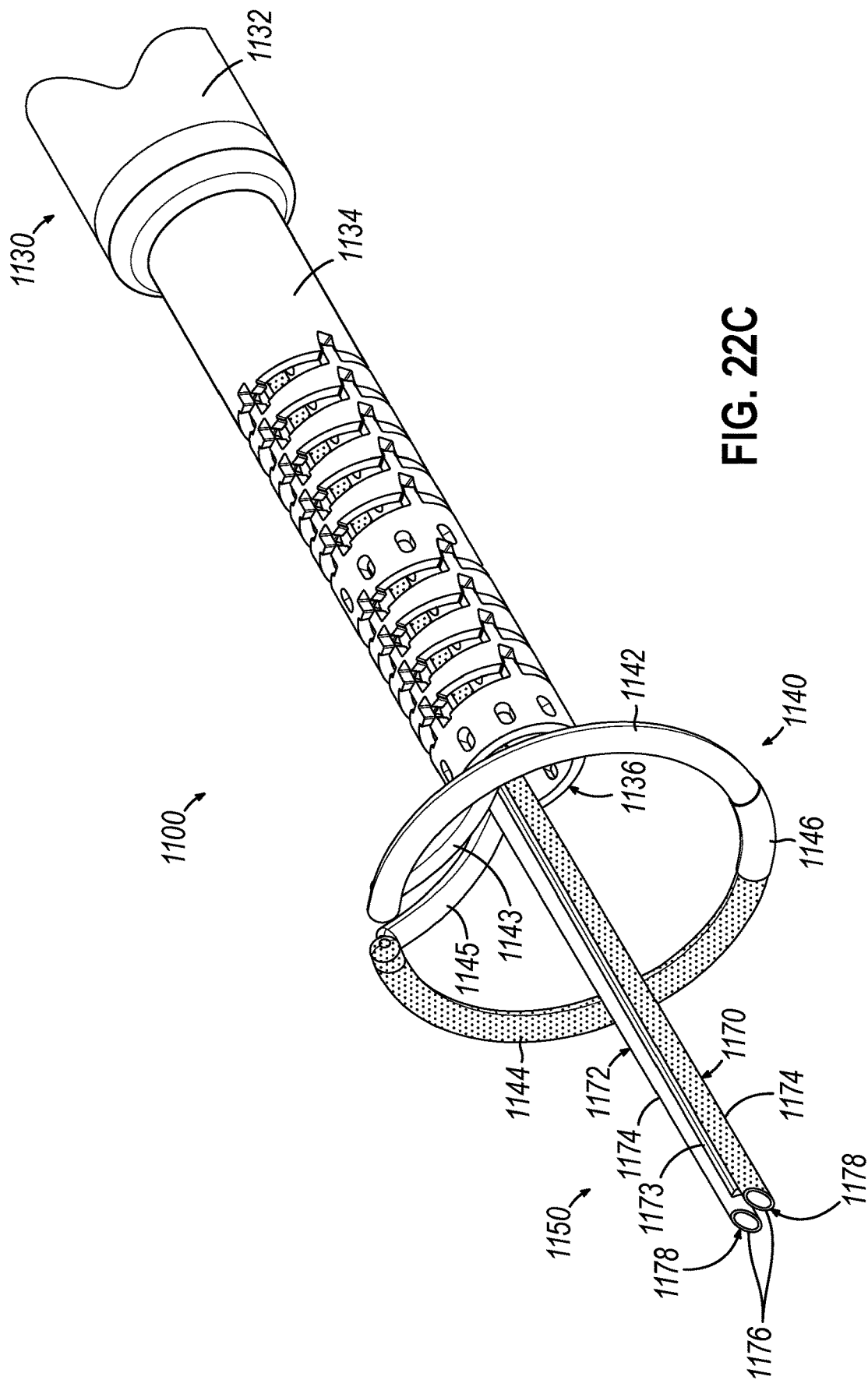
FIG. 22C depicts a perspective view of the distal portion of the shaft assembly of the instrument of FIG. 21, with the loop electrode assembly in a distal extended position relative to the shaft assembly, and with the pair of needle electrodes in the distal extended position relative to the shaft assembly.

FIGS. 21-22C show an example of an instrument (1100) that may be used to deliver RF energy to tissue. For instance, instrument (1100) may be used to ablate a nerve (e.g., the posterior nasal nerve (40)); ablate a turbinate (e.g., any of turbinates (20, 22, 24)); or ablate, electroporate (e.g., to promote absorption of therapeutic agents, etc.), or apply resistive heating to any other kind of anatomical structure in the head of a patient. Instrument (1100) of this example includes a handle assembly (1110), a shaft assembly (1130), a loop electrode assembly (1140), and a needle electrode assembly (1150). Instrument (1100) is coupled with an RF generator (1102), which is operable to generate RF electrosurgical energy for delivery to tissue via electrodes (1142, 1144, 1170, 1172) as will be described in greater detail below.

Handle assembly (1110) of this example includes a body (1112), a first slider (1120), and a second slider (1122). Body (1112) is sized and configured to be grasped and operated by a single hand of an operator, such as via a power grip, a pencil grip, or any other suitable kind of grip. Each slider (1120, 1122) is operable to translate longitudinally relative to body (1112). Sliders (1120, 1122) are operable to translate independently relative to each other in some versions. Slider (1120) is coupled with loop electrode assembly (1140) and is thus operable to translate loop electrode assembly (1140) longitudinally as will be described in greater detail below. The transition from FIG. 22B to FIG. 22C shows loop electrode assembly (1140) being driven by slider (1120) from a proximal position to a distal position. Slider (1122) is coupled with needle electrode assembly (1150) and is thus operable to translate needle electrode assembly (1150) longitudinally as will be described in greater detail below. The transition from FIG. 22A to FIG. 22B shows needle electrode assembly (1150) being driven by slider (1122) from a proximal position to a distal position.

Shaft assembly (1130) of the present example includes a rigid portion (1132), a flexible portion (1134) distal to rigid portion (1132), and an open distal end (1136). A pull-wire (not shown) is coupled with flexible portion (1134) and with a deflection control knob (1116) of handle assembly (1110). Deflection control knob (1116) is rotatable relative to body (1112), about an axis that is perpendicular to the longitudinal axis of shaft assembly (1130), to selectively retract the pull-wire proximally. As the pull-wire is retracted proximally, flexible portion (1134) bends and thereby deflects distal end (1136) laterally away from the longitudinal axis of rigid portion (1132). Deflection control knob (1116), the pull-wire, and flexible portion (1134) thus cooperate to impart steerability to shaft assembly (1130). By way of example only, such steerability of shaft assembly (1130) may be provided in accordance with at least some of the teachings of U.S. Pat. App. No. 63/028,609, entitled "Shaft Deflection Control Assembly for ENT Guide Instrument," filed May 22, 2020, the disclosure of which is incorporated by reference herein, in its entirety. Other versions may provide some other kind of user input feature to drive steering of flexible portion (1134), instead of deflection control knob (1116). In some alternative versions, deflection control knob (1116) is omitted, and flexible portion (1134) is malleable. In still other versions, the entire length of shaft assembly (1130) is rigid.

Shaft assembly (1130) is also rotatable relative to handle assembly (1110), about the longitudinal axis of rigid portion (1132). Such rotation may be driven via rotation control knob (1114), which is rotatably coupled with body (1112) of handle assembly (1110). Alternatively, shaft assembly (1130) may be rotated via some other form of user input; or may be non-rotatable relative to handle assembly (1110). It should also be understood that the example of handle assembly (1110) described herein is merely an illustrative example. Shaft assembly (1130) may instead be coupled with any other suitable kind of handle assembly or other supporting body.

As best seen in FIG. 22C, loop electrode assembly (1140) of the present example includes a pair of arcuate arms (1142, 1144). One end of arcuate arm (1142) is secured to a deployment arm (1143); while the other end of arcuate arm (1142) is secured to a junction (1146). Similarly, one end of arcuate arm (1144) is secured to a deployment arm (1145); while the other end of arcuate arm (1144) is secured to junction (1146). In some versions, arcuate arm (1142) and deployment arm (1143) are unitarily formed from the same first metallic wire; while arcuate arm (1144) and deployment arm (1145) are unitarily formed from the same second metallic wire. Deployment arms (1143, 1145) extend along the length of shaft assembly (1130) and are coupled with first slider (1120). Each deployment arm (1143, 1145) may include an electrically insulative coating or sheath to prevent short circuiting within shaft assembly (1130), with arcuate arms (1142, 1144) being left exposed to serve as electrodes. Each arcuate arm (1142, 1144) is coupled with a corresponding one or more wire(s), trace(s), and/or other conductive element(s) that electrically couple arcuate arms (1142, 1144) with RF generator (1102). Arcuate arm (1142) is configured to apply RF energy at a first polarity; while arcuate arm (1144) is configured to apply RF energy at a second polarity. Arcuate arms (1142, 1144) thus serve as electrodes that are operable to apply bipolar RF energy to tissue contacting arcuate arms (1142, 1144). Junction (1146) is formed of an electrically insulative material that prevents short circuiting between arcuate arms (1142, 1144) while mechanically securing the corresponding ends of arcuate arms (1142, 1144) together.

As shown in FIG. 22C, arcuate arms (1142, 1144) are resiliently biased to define arcuate configurations when arcuate arms (1142, 1144) are exposed relative to distal end (1136) of shaft assembly (1130). By way of example only, arcuate arms (1142, 1144) may be formed of nitinol. In the present example, arcuate arms (1142, 1144) extend along a curve defined by a single radius. Arcuate arms (1142, 1144) and junction (1146) thus cooperate to define a generally circular shape. In some other versions, arcuate arms (1142, 1144) and junction (1146) cooperate to define a shape that is elliptical, oval-shaped, square, triangular, or otherwise non-circular. In the present example, the generally circular shape defined by arcuate arms (1142, 1144) and junction (1146) extends along a plane that is perpendicular to the longitudinal axis of shaft assembly (1130). In some other versions, the generally circular shape (or other non-circular shape) defined by arcuate arms (1142, 1144) and junction (1146) extends along a plane that is obliquely oriented or otherwise transverse to the longitudinal axis of shaft assembly (1130).

During use of loop electrode assembly (1140), when loop electrode assembly (1140) is fully deployed from distal end (1136) of shaft assembly (1130) as shown in FIG. 22C, the operator may press loop electrode assembly (1140) against the tissue that the operator wishes to ablate (or otherwise apply RF energy to), using a stamping type of motion. With the tissue adequately engaged by arcuate arms (1142, 1144), the operator may then activate RF generator (1102), with arcuate arms (1142, 1144) serving as electrodes applying bipolar RF energy to the tissue against which loop electrode assembly (1140) is pressed. This may provide ablation that is relatively shallow as compared to ablation provided via needle electrodes (1170, 1172) described below. In some scenarios, saline or other irrigation fluid may be expelled through shaft assembly (1130) while RF energy is being applied to tissue via electrode assembly (1140), thereby promoting electrical continuity. In addition, or in the alternative, suction may be applied via shaft assembly (1130) to evacuate smoke, vapor, etc. that is generated during the ablation procedure.

In some instances, an operator may wish to only partially deploy loop electrode assembly (1140) from distal end (1136) of shaft assembly (1130). As shown in FIG. 22B, with first slider (1120) in a proximal-most position, loop electrode assembly (1140) may be fully contained within shaft assembly (1130). When first slider (1120) is partially advanced distally to an intermediate longitudinal position (not shown), loop electrode assembly (1140) may partially extend distally from distal end (1136) of shaft assembly (1130) (not shown). In this state, the resilience of loop electrode assembly (1140) may provide some degree of outward bowing of arcuate arms (1142, 1144), without arcuate arms (1142, 1144) defining a generally circular shape. The operator may nevertheless press arcuate arms (1142, 1144) against tissue when loop electrode assembly (1140) is in a partially deployed state, and then activate arcuate arms (1142, 1144) to apply RF energy to tissue. If the operator chooses to fully deploy loop electrode assembly (1140) in addition to or in lieu of applying RF energy to tissue while loop electrode assembly (1140) is in the partially deployed state, the operator may continue to advance first slider (1120) to a distal position. With first slider (1120) in a distal position, loop electrode assembly (1140) may be fully deployed and thereby define the generally circular shape shown in FIG. 22C. By way of example only, such partial and/or full deployment of loop electrode assembly (1140) may be provided in accordance with at least some of the teachings of U.S. Pat. App. No. 63/067,495, entitled "ENT Ablation Instrument with Electrode Loop," filed Aug. 19, 2020, the disclosure of which is incorporated by reference herein, in its entirety.

As best seen in FIGS. 22B and 22C, needle electrode assembly (1150) of the present example includes a pair of needle electrodes (1170, 1172) that are fixed longitudinally relative to each other by a barrier (1173). While two needle electrodes (1170, 1172) are shown, any other suitable number of needle electrodes (1170, 1172) may be provided. Each needle electrode (1170, 1172) of this example includes a needle shaft (1174) with a sharp distal tip (1176) and a lumen (1178) extending to an opening at tip (1176). Needle electrodes (1170, 1172) may be used to deliver fluid (e.g., irrigation fluid, therapeutic agent, etc.) to tissue via lumens (1178). Alternatively, lumens (1178) may be omitted in some versions.

When second slider (1122) is advanced distally, needle electrodes (1170, 1172) are driven to extend distally past the transverse plane defined by loop electrode assembly (1140), as shown in FIG. 22C. The operator may arrest distal advancement of second slider (1122) at any suitable position along the length of body (1112) of handle assembly (1110) to achieve any suitable depth of penetration of needle electrodes (1170, 1172) into tissue. Each needle electrode (1170, 1172) may include an electrically insulative coating or sheath to prevent short circuiting within shaft assembly (1130), distal portions of the respective needle shafts (1174) being left exposed to serve as electrodes. Each needle shaft (1174) is coupled with a corresponding one or more wire(s), trace(s), and/or other conductive element(s) that electrically couple needle shafts (1174) with RF generator (1102). Needle electrodes (1170, 1172) are thus operable to apply RF energy to tissue in which needle electrode assembly (1150) is disposed. Barrier (1173) is formed of an electrically insulative material (e.g., plastic, etc.) that prevents short circuiting between needle shafts (1174) (e.g., in cases where needle shafts (1174) are configured to apply RF energy at different polarities from each other, as described below); while mechanically securing the corresponding sides of needle shafts (1174) together. In some versions, barrier (1173) is formed of a flexible material to accommodate bending or other deflecting of needle electrodes (1170, 1172), such as laterally away from the longitudinal axis of rigid portion (1132). Barrier (1173) may also include a heat resistant material, to avoid melting or other deformation of barrier (1173) in the event that needle electrodes (1170, 1172) heat up while applying RF energy.

In the present example, needle electrodes (1170, 1172) are straight and configured to extend along or parallel to the longitudinal axis of shaft assembly (1130) when needle electrodes (1170, 1172) are distally positioned as shown in FIG. 22B. In some versions, needle electrodes (1170, 1172) may be resiliently biased to splay outwardly relative to the longitudinal axis of shaft assembly (1130) when needle electrodes (1170, 1172) are distally positioned. By way of example only, such biasing and/or outward splaying of needle electrodes (1170, 1172) may be provided in accordance with at least some of the teachings of U.S. Pat. App. No. 63/067,495, entitled "ENT Ablation Instrument with Electrode Loop," filed Aug. 19, 2020.

In some versions, both needle electrodes (1170, 1172) have the same polarity. In such versions, needle electrodes (1170, 1172) may cooperate with an electrode pad in contact with the skin of the patient to provide monopolar RF energy. In some other such versions, needle electrodes (1170, 1172) may serve as active electrodes (or return electrodes) while loop electrode assembly (1140) serves as a return electrode (or active electrode) to provide bipolar RF energy to tissue. As another variation, needle electrodes (1170, 1172) may cooperate with each other to apply bipolar RF energy to tissue. For instance, needle electrode (1170) may serve as an active electrode while needle electrode (1172) may serve as a return electrode. In such versions, arcuate arm (1142) may serve as a return electrode while arcuate arm (1144) may serve as an active electrode. In this manner, needle electrode (1170) and arcuate arm (1142), which are each generally positioned on a first lateral side relative to barrier (1173), may cooperate with each other to provide bipolar RF energy to tissue between needle electrode (1170) and arcuate arm (1142). Likewise, needle electrode (1172) and arcuate arm (1144), which are each generally positioned on a second lateral side relative to barrier (1173), may cooperate with each other to provide bipolar RF energy to tissue between needle electrode (1172) and arcuate arm (1144).

When needle electrodes (1170, 1172) are used to deliver RF energy to tissue, needle electrodes (1170, 1172) may be advanced into the tissue such that needle electrodes (1170, 1172) penetrate the tissue; then needle electrodes (1170, 1172) may be activated to apply the RF energy to the penetrated tissue. When loop electrode assembly (1140) is used to deliver RF energy to tissue, loop electrode assembly (1140) may be pressed against the tissue such that loop electrode assembly (1140) engages the tissue; then loop electrode assembly (1140) may be activated to apply the RF energy to the engaged tissue.

As indicated above, instrument (1100) allows an operator to choose between applying RF energy to a surface of tissue (e.g., via loop electrode assembly (1140)) and/or within penetrated tissue (e.g., via needle electrodes (1170, 1172)). Thus, instrument (1100) may be used to perform a relatively shallow ablation (e.g., via loop electrode assembly (1140)), a relatively deep ablation (e.g., via needle electrodes (1170, 1172)), or a volumetric ablation (e.g., via loop electrode assembly (1140) in combination with needle electrodes (1170, 1172)). By way of further example only, instrument (1100) may be used to perform a vidian neurectomy, a posterior nasal neurectomy, a turbinate reduction, or any other suitable procedure. In some cases, a combination of loop electrode assembly (1140) and needle electrodes (1170, 1172) may be used to perform a turbinate reduction. Other suitable ways in which needle electrodes (1170, 1172) and/or loop electrode assembly (1140) may be used to apply RF energy to tissue will be apparent to those skilled in the art in view of the teachings herein.

While not shown, instrument (1100) may also include one or more position sensors that are operable to generate signals indicative of the position of distal end (1136), or some other component of instrument (1100), in three-dimensional space. Such a position sensor may be integrated directly into shaft assembly (1130) or elsewhere into instrument. In addition, or in the alternative, such a position sensor may be integrated into a guidewire or other component that is disposed in shaft assembly (1130). Such a position sensor may take the form of one or more coils that generate signals in response to the presence of an alternating magnetic field. The position data generated by such position signals may be processed by a system that provides a visual indication to the operator to show the operator where the distal end (1136), or some other component of instrument (1100), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

As shown in FIGS. 22A-22C, loop electrode assembly (1140) and needle electrode assembly (1150) may be selectively advanced and retracted relative to shaft assembly (1130) via sliders (1120, 1122). Alternatively, loop electrode assembly (1140) and/or needle electrode assembly (1150) may be longitudinally fixed relative to shaft assembly (1130). In such versions, loop electrode assembly (1140) and/or needle electrode assembly (1150) may be selectively contained within, or exposed by, an outer sheath (not shown) that is slidably disposed relative to shaft assembly (1130).

For instance, shaft assembly (1130) may slide longitudinally relative to such an outer sheath, or the outer sheath may slide longitudinally relative to shaft assembly (1130), to selectively contain or expose loop electrode assembly (1140) and/or needle electrode assembly (1150). Regardless of how loop electrode assembly (1140) and needle electrode assembly (1150) are advanced, retracted, contained, or exposed, the degree of advancement, retraction, containment, or exposure may be selected and adjusted in a manner similar to that described above to thereby vary the degree of tissue contact.

IX. EXAMPLE OF RF ABLATION INSTRUMENT WITH LOOP ELECTRODE ASSEMBLY AND NEEDLE ELECTRODE ASSEMBLY HAVING MULTIPLE POLARITIES

Figure 23A:
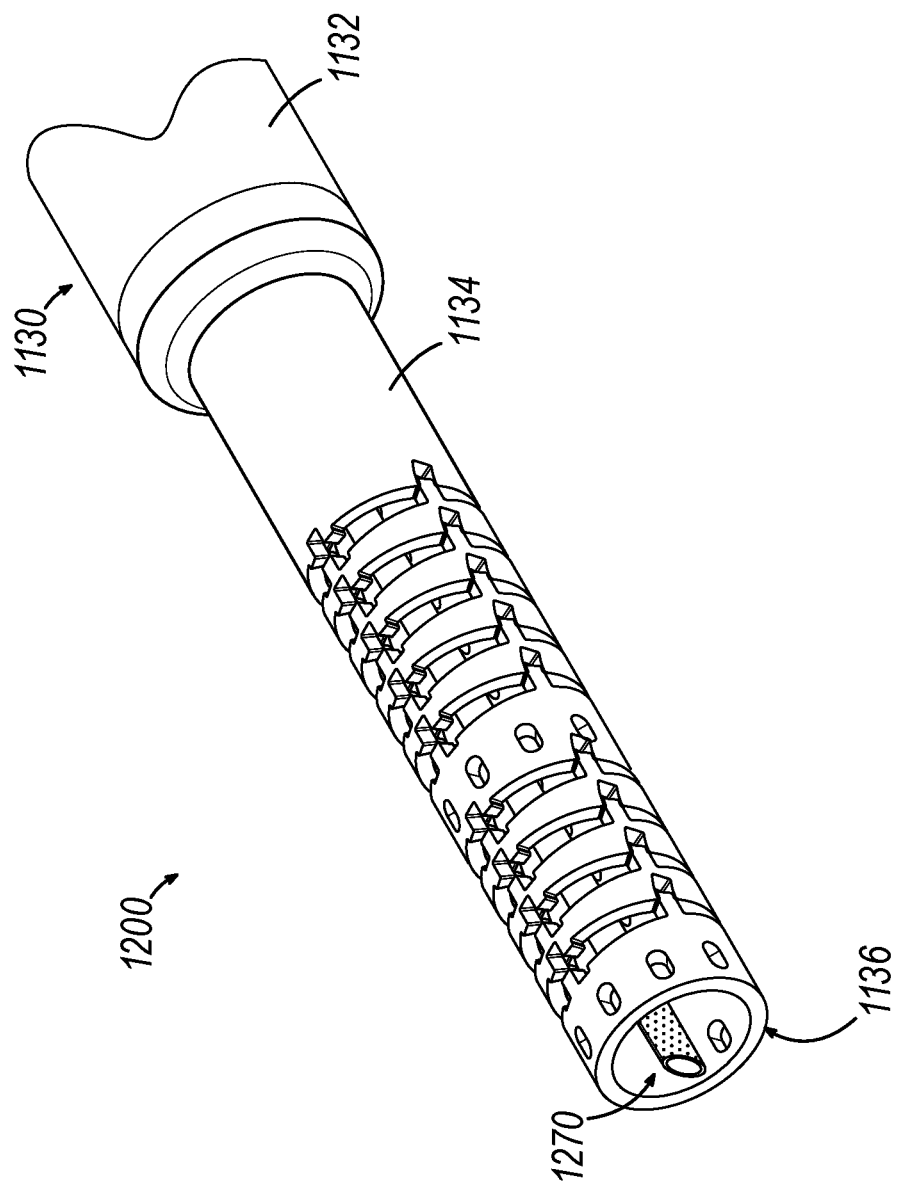
FIG. 23A depicts a perspective view of a distal portion of a shaft assembly of another example of an instrument that may be used to perform an ablation procedure in a nasal cavity, with a loop electrode assembly of the instrument in a proximal retracted position relative to the shaft assembly, and with a needle electrode assembly of the instrument in a proximal retracted position relative to the shaft assembly.
Figure 23B:
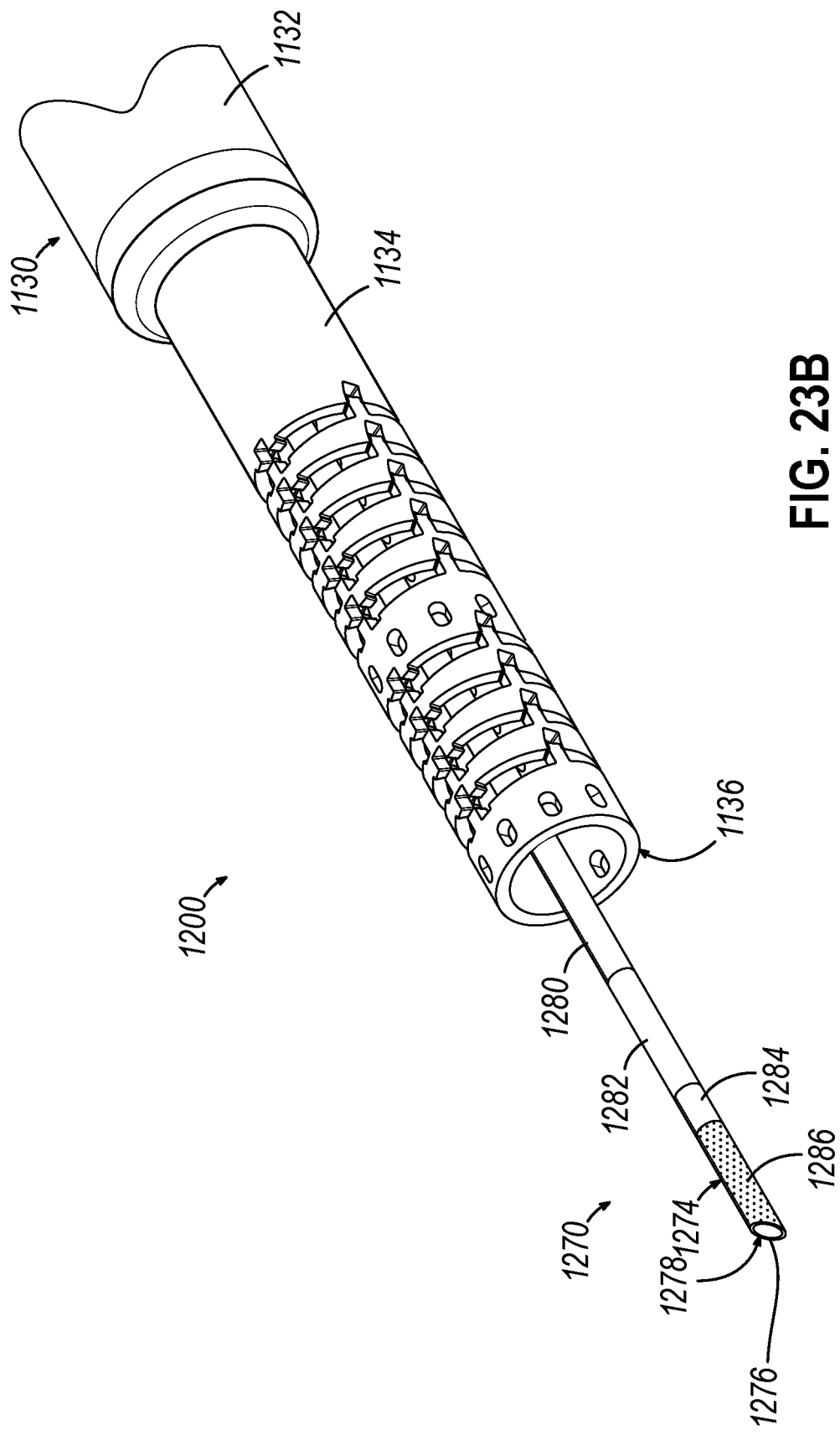
FIG. 23B depicts a perspective view of the distal portion of the shaft assembly of the instrument of FIG. 23A, with the loop electrode assembly in the proximal retracted position relative to the shaft assembly, and with the needle electrode assembly in a distal extended position relative to the shaft assembly.
Figure 23C:
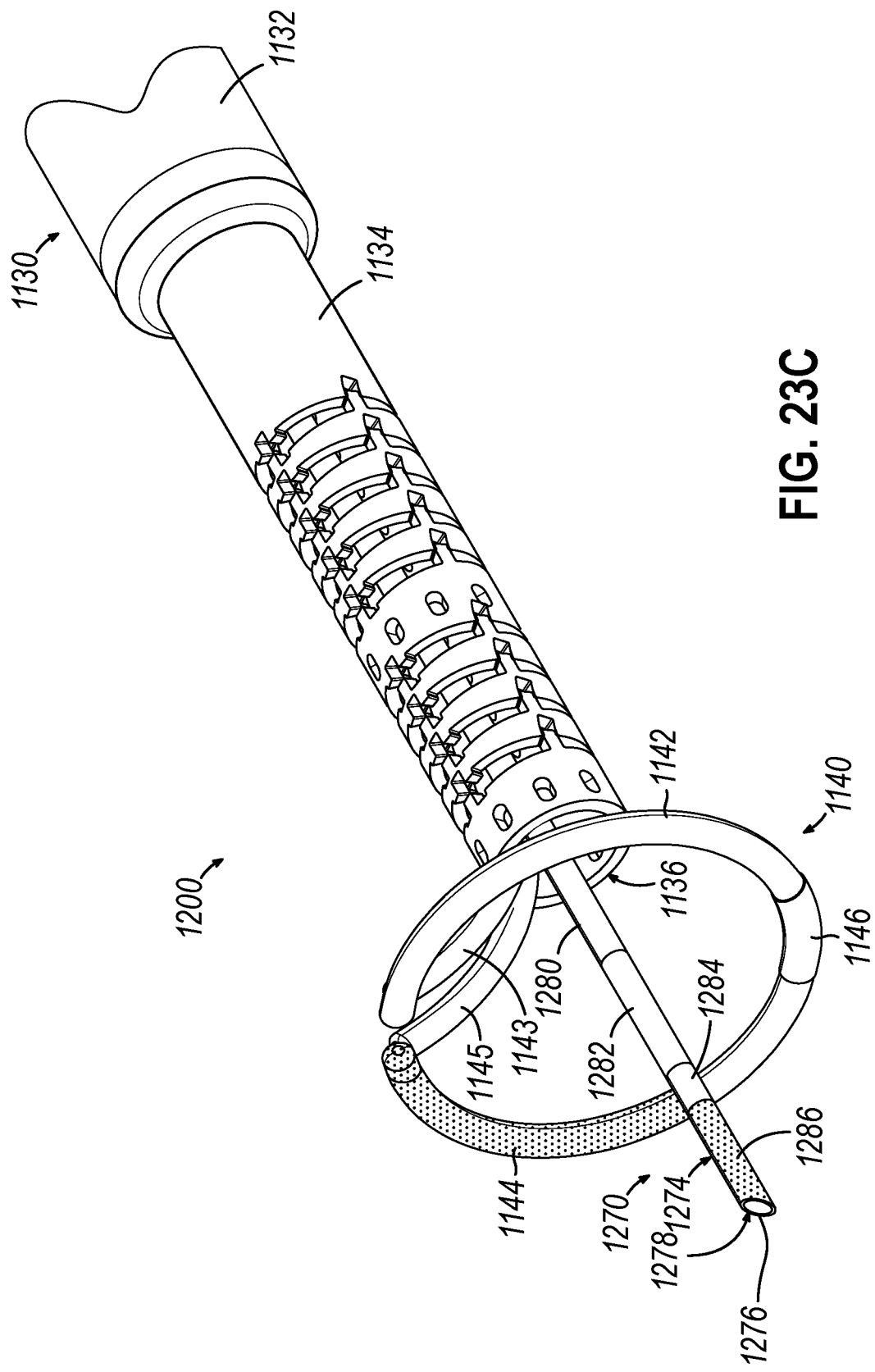
FIG. 23C depicts a perspective view of the distal portion of the shaft assembly of the instrument of FIG. 23A, with the loop electrode assembly in a distal extended position relative to the shaft assembly, and with the needle electrode assembly in the distal extended position relative to the shaft assembly.

FIGS. 23A-23C show a distal portion of another example of an instrument (1200) that may be used to deliver RF energy to tissue. For instance, instrument (1200) may be used to ablate a nerve (e.g., the posterior nasal nerve (40)), ablate a turbinate (e.g., any of turbinates (20, 22, 24)), or ablate, electroporate (e.g., to promote absorption of therapeutic agents, etc.), or apply resistive heating to any other kind of anatomical structure in the head of a patient. Instrument (1200) is substantially similar to instrument (1100) except as otherwise described herein. Instrument (1200) of this example includes handle assembly (1110), shaft assembly (1130), loop electrode assembly (1140), and a needle electrode assembly (1270). Instrument (1200) is coupled with RF generator (1102), which is operable to generate RF electrosurgical energy for delivery to tissue via electrodes (1142, 1144, 1282, 1286) as will be described in greater detail below. The transition from FIG. 23A to FIG. 23B shows needle electrode assembly (1270) being driven by slider (1122) from a proximal position to a distal position. The transition from FIG. 23B to FIG. 23C shows loop electrode assembly (1140) being driven by slider (1120) from a proximal position to a distal position. Of course, handle assembly (1110) is just an illustrative example; and sliders (1120, 1122) may be substituted with any other suitable kinds of structures to drive translation of loop electrode assembly (1140) and needle electrode assembly (1270).

As best shown in FIGS. 23B and 23C, needle electrode assembly (1270) of this example includes a needle shaft (1274) with a sharp distal tip (1276) and a lumen (1278) extending to an opening at tip (1276). Needle electrode assembly (1270) may be used to deliver fluid (e.g., irrigation fluid, therapeutic agent, etc.) to tissue via lumen (1278). Alternatively, lumen (1278) may be omitted in some versions. When second slider (1122) is advanced distally, needle electrode assembly (1270) is driven to extend distally past the transverse plane defined by loop electrode assembly (1140), as shown in FIG. 23C. The operator may arrest distal advancement of second slider (1122) at any suitable position along the length of body (1112) of handle assembly (1110) to achieve any suitable depth of penetration of needle electrode assembly (1270) into tissue.

Needle shaft (1274) includes a proximal insulative segment (1280), a proximal conductive segment (1282) positioned distally of proximal insulative segment (1280), a distal insulative segment (1284) positioned distally of proximal conductive segment (1282), and a distal conductive segment (1286) positioned distally of distal insulative segment (1284). While two conductive segments (1282, 1286) are shown, any other suitable number of conductive segments (1282, 1286) may be provided. In some versions, proximal and distal insulative segments (1280, 1284) are unitarily formed from the same first insulative body (e.g., cylindrical tube), and proximal conductive segment (1282) may have a greater diameter than that of proximal and distal insulative segments (1280, 1284) to permit distal insulative segment (1284) to electrically isolate proximal conductive segment (1282) from distal conductive segment (1286). Each conductive segment (1282, 1286) is coupled with a corresponding one or more wire(s), trace(s), and/or other conductive element(s) that electrically couple conductive segments (1282, 1286) with RF generator (1102), such that conductive segments (1282, 1286) are operable to serve as corresponding RF electrodes. Needle electrode assembly (1270) is thus operable to apply RF energy to tissue in which needle electrode assembly (1270) is disposed. Distal insulative segment (1284) is formed of an electrically insulative material that prevents short circuiting between conductive segments (1282, 1286) (e.g., in cases where conductive segments (1282, 1286) are configured to apply RF energy at different polarities from each other, as described below).

Loop electrode assembly (1140) and needle electrode assembly (1270) are operable to apply bipolar RF energy to tissue. In some versions, loop electrode assembly (1140) provides a first polarity of RF energy while needle electrode assembly (1270) provides a second polarity of RF energy. As another example, loop electrode assembly (1140) may itself be configured to apply bipolar RF energy to tissue. For instance, arcuate arm (1142) may be configured to provide a first polarity of RF energy while arcuate arm (1144) may be configured to provide a second polarity of RF energy. Some versions of needle electrode assembly (1270) may itself also be configured to apply bipolar RF energy to tissue. For instance, proximal conductive segment (1282) may be configured to provide a first polarity of RF energy while distal conductive segment (1286) may be configured to provide a second polarity of RF energy. In some versions, distal conductive segment (1286) may serve as an active electrode while proximal conductive segment (1282) may serve as a return electrode. In other versions, proximal conductive segment (1282) may serve as an active electrode while distal conductive segment (1286) may serve as a return electrode. Other suitable ways in which polarities may be allocated among loop electrode assembly (1140) and needle electrode assembly (1270) will be apparent to those skilled in the art in view of the teachings herein.

During use of instrument (1200), the operator may press loop electrode assembly (1140) against the tissue that the operator wishes to ablate (or otherwise apply RF energy to), using a stamping type of motion. With the tissue adequately engaged by loop electrode assembly (1140), the operator may then activate RF generator (1102), with arcuate arms (1142, 1144) of loop electrode assembly (1140) serving as electrodes applying bipolar RF energy to the tissue against which loop electrode assembly (1140) is pressed. This may provide ablation that is relatively shallow. In scenarios where the operator wishes to provide a relatively deep ablation, the operator may advance needle electrode assembly (1270) into tissue and activate needle electrode assembly (1270) to apply RF energy to the tissue in which needle electrode assembly (1270) is disposed. In scenarios where the operator wishes to apply volumetric ablation, the operator may activate at least one conductive segment (1282, 1286) of needle electrode assembly (1270) simultaneously with at least one arcuate arm (1142, 1144) of loop electrode assembly (1140). By way of further example only, instrument (1200) may be used to perform a vidian neurectomy, a posterior nasal neurectomy, a turbinate reduction, or any other suitable procedure. In some cases, a combination of loop electrode assembly (1140) and needle electrode assembly (1270) may be used to perform a turbinate reduction. Other suitable ways in which loop electrode assembly (1140) and/or needle electrode assembly (1270) may be used to apply RF energy to tissue will be apparent to those skilled in the art in view of the teachings herein.

While not shown, instrument (1200) may also include one or more position sensors that are operable to generate signals indicative of the position of loop electrode assembly (1140) and/or needle electrode assembly (1270), or some other component of instrument (1200), in three-dimensional space. Such a position sensor may be integrated directly into shaft assembly (1130) or elsewhere into instrument. In addition, or in the alternative, such a position sensor may be integrated into a guidewire or other component that is disposed in shaft assembly (1130). Such a position sensor may take the form of one or more coils that generate signals in response to the presence of an alternating magnetic field. The position data generated by such position signals may be processed by a system that provides a visual indication to the operator to show the operator where loop electrode assembly (1140) and/or needle electrode assembly (1270), or some other component of instrument (1200), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

X. EXAMPLE OF RF ABLATION INSTRUMENT WITH LOOP ELECTRODE ASSEMBLY AND NEEDLE ELECTRODE ASSEMBLY HAVING INSULATIVE NEEDLE SHAFT AND CONDUCTIVE RINGS

Figure 24A:
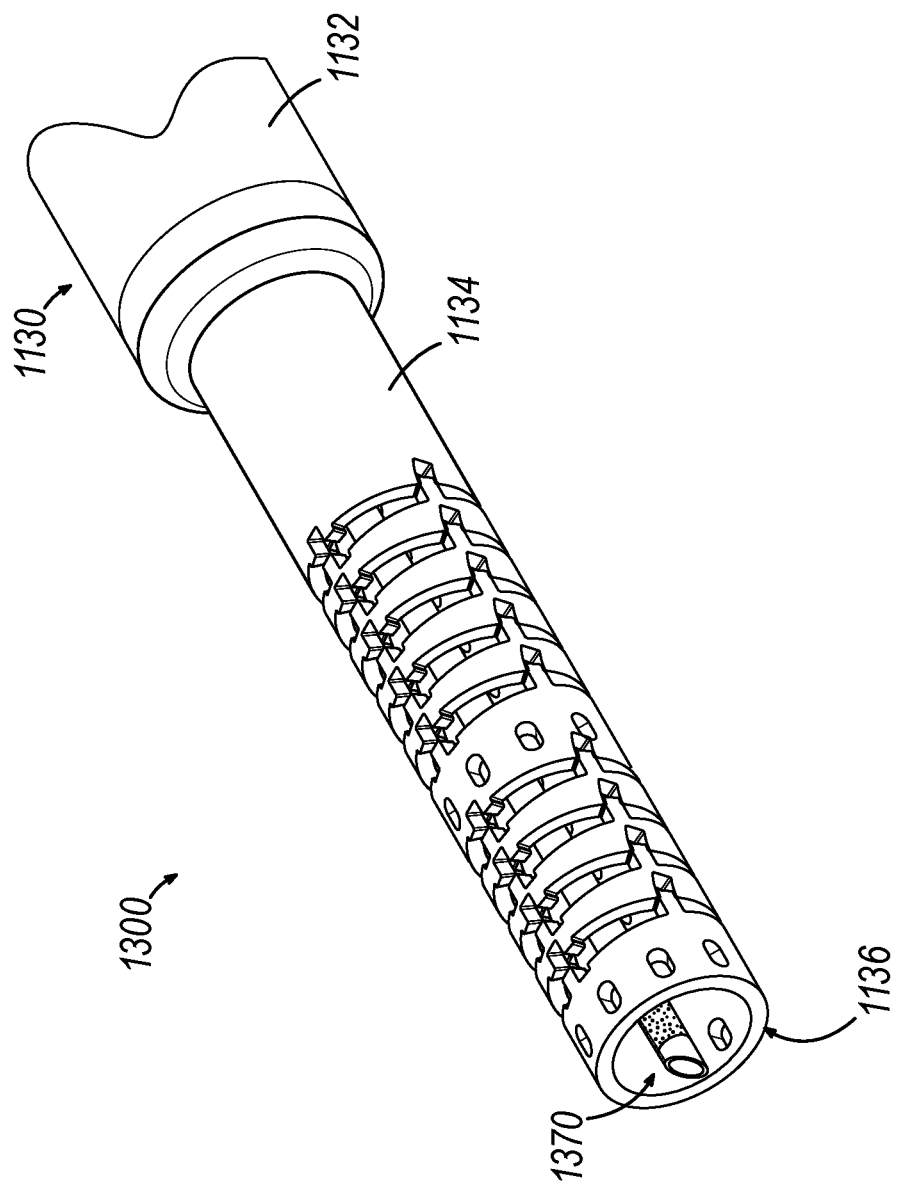
FIG. 24A depicts a perspective view of a distal portion of a shaft assembly of another example of an instrument that may be used to perform an ablation procedure in a nasal cavity, with a loop electrode assembly of the instrument in a proximal retracted position relative to the shaft assembly, and with a needle electrode assembly of the instrument in a proximal retracted position relative to the shaft assembly.
Figure 24B:
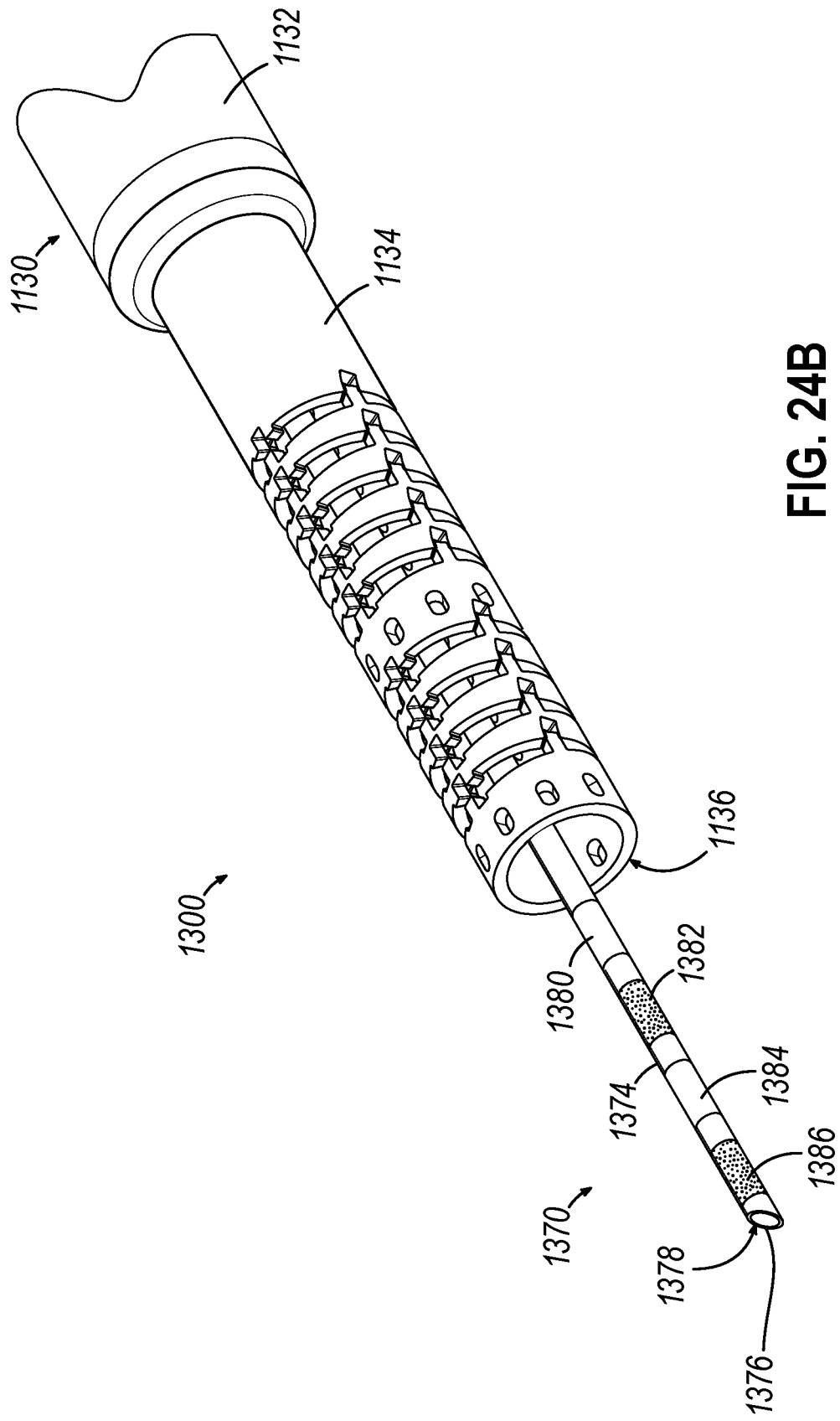
FIG. 24B depicts a perspective view of the distal portion of the shaft assembly of the instrument of FIG. 24A, with the loop electrode assembly in the proximal retracted position relative to the shaft assembly, and with the needle electrode assembly in a distal extended position relative to the shaft assembly.
Figure 24C:
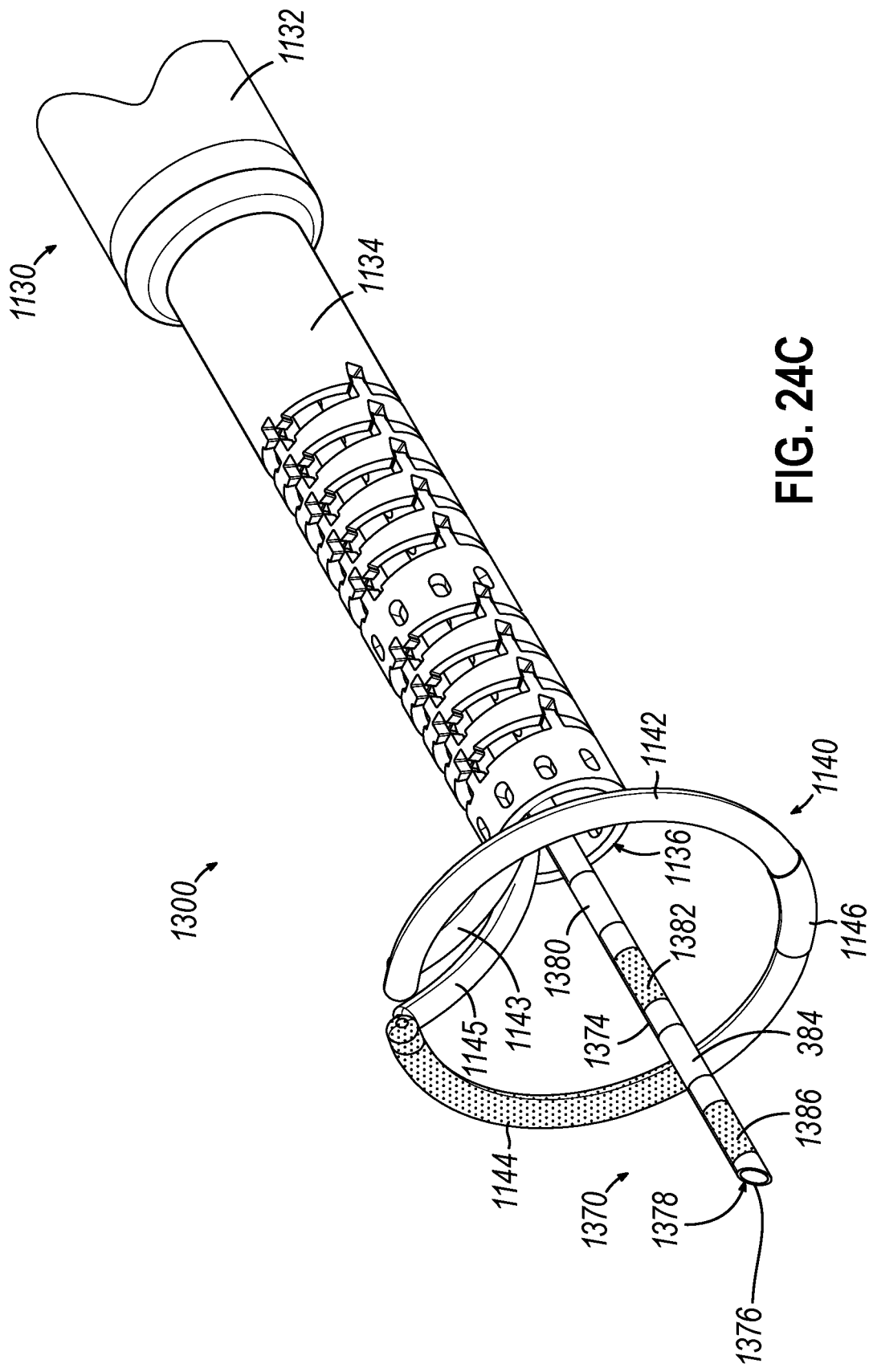
FIG. 24C depicts a perspective view of the distal portion of the shaft assembly of the instrument of FIG. 24A, with the loop electrode assembly in a distal extended position relative to the shaft assembly, and with the needle electrode assembly in the distal extended position relative to the shaft assembly.

FIGS. 24A-24C show a distal portion of another example of an instrument (1300) that may be used to deliver RF energy to tissue. For instance, instrument (1300) may be used to ablate a nerve (e.g., the posterior nasal nerve (40)), ablate a turbinate (e.g., any of turbinates (20, 22, 24)), or ablate, electroporate (e.g., to promote absorption of therapeutic agents, etc.), or apply resistive heating to any other kind of anatomical structure in the head of a patient. Instrument (1300) is substantially similar to instrument (1100) except as otherwise described herein. Instrument (1300) of this example includes handle assembly (1110), shaft assembly (1130), loop electrode assembly (1140), and a needle electrode assembly (1370). Instrument (1300) is coupled with RF generator (1102), which is operable to generate RF electrosurgical energy for delivery to tissue via electrodes (1142, 1144, 1380, 1382, 1384, 1386) as will be described in greater detail below. The transition from FIG. 24A to FIG. 24B shows needle electrode assembly (1370) being driven by slider (1122) from a proximal position to a distal position. The transition from FIG. 24B to FIG. 24C shows loop electrode assembly (1140) being driven by slider (1120) from a proximal position to a distal position. Of course, handle assembly (1110) is just an illustrative example; and sliders (1120, 1122) may be substituted with any other suitable kinds of structures to drive translation of loop electrode assembly (1140) and needle electrode assembly (1370).

As best shown in FIGS. 24B and 24C, needle electrode assembly (1370) of this example includes a needle shaft (1374) with a sharp distal tip (1376) and a lumen (1378) extending to an opening at tip (1376). Needle electrode assembly (1370) may be used to deliver fluid (e.g., irrigation fluid, therapeutic agent, etc.) to tissue via lumen (1278). Alternatively, lumen (1378) may be omitted in some versions. When second slider (1122) is advanced distally, needle electrode assembly (1370) is driven to extend distally past the transverse plane defined by loop electrode assembly (1140), as shown in FIG. 24C. The operator may arrest distal advancement of second slider (1122) at any suitable position along the length of body (1112) of handle assembly (1110) to achieve any suitable depth of penetration of needle electrode assembly (1370) into tissue. Needle electrode assembly (1370) of this example further includes a plurality of conductive rings (1380, 1382, 1384, 1386) positioned circumferentially about shaft (1374) and axially spaced apart from each other therealong. More particularly, needle electrode assembly (1370) includes a first conductive ring (1380), a second conductive ring (1382) positioned distally of first conductive ring (1380), a third conductive ring (1384) positioned distally of second conductive ring (1382), and a fourth conductive ring (1386) positioned distally of third conductive ring (1384). While four conductive rings (1380, 1382, 1384, 1386) are shown, any other suitable number of conductive rings (1380, 1382, 1384, 1386) may be provided. Each conductive ring (1380, 1382, 1384, 1386) is coupled with a corresponding one or more wire(s), trace(s), and/or other conductive element(s) that electrically couple conductive rings (1380, 1382, 1384, 1386) with RF generator (1102), such that conductive rings (1380, 1382, 1384, 1386) are operable to serve as corresponding RF electrodes. Needle electrode assembly (1370) is thus operable to apply RF energy to tissue in which needle electrode assembly (1370) is disposed. Needle shaft (1374) may be formed of an electrically insulative material that prevents short circuiting between conductive rings (1380, 1382, 1384, 1386) (e.g., in cases where conductive rings (1380, 1382, 1384, 1386) are configured to apply RF energy at different polarities from each other, as described below).

Loop electrode assembly (1140) and needle electrode assembly (1370) are operable to apply bipolar RF energy to tissue. In some versions, loop electrode assembly (1140) provides a first polarity of RF energy while needle electrode assembly (1370) provides a second polarity of RF energy. As another example, loop electrode assembly (1140) may itself be configured to apply bipolar RF energy to tissue. For instance, arcuate arm (1142) may be configured to provide a first polarity of RF energy while arcuate arm (1144) may be configured to provide a second polarity of RF energy. Some versions of needle electrode assembly (1370) may itself also be configured to apply bipolar RF energy to tissue. For instance, first and third conductive rings (1380, 1384) may be configured to provide a first polarity of RF energy while second and fourth conductive rings (1382, 1386) may be configured to provide a second polarity of RF energy to provide alternating polarities in the axial direction along needle shaft (1374). In some versions, second and fourth conductive rings (1382, 1386) may serve as active electrodes while first and third conductive rings (1380, 1384) may serve as return electrodes. Other suitable ways in which polarities may be allocated among loop electrode assembly (1140) and needle electrode assembly (1370) will be apparent to those skilled in the art in view of the teachings herein.

During use of instrument (1300), the operator may press loop electrode assembly (1140) against the tissue that the operator wishes to ablate (or otherwise apply RF energy to), using a stamping type of motion. With the tissue adequately engaged by loop electrode assembly (1140), the operator may then activate RF generator (1102), with arcuate arms (1142, 1144) of loop electrode assembly (1140) serving as electrodes applying bipolar RF energy to the tissue against which loop electrode assembly (1140) is pressed. This may provide ablation that is relatively shallow. In scenarios where the operator wishes to provide a relatively deep ablation, the operator may advance needle electrode assembly (1370) into tissue and activate at least two conductive rings (1380, 1382, 1384, 1386) of needle electrode assembly (1370) to apply RF energy to the tissue in which needle electrode assembly (1370) is disposed. In scenarios where the operator wishes to apply volumetric ablation, the operator may activate at least one conductive ring (1380, 1382, 1384, 1386) of needle electrode assembly (1370) simultaneously with at least one arcuate arm (1142, 1144) of loop electrode assembly (1140). By way of further example only, instrument (1300) may be used to perform a vidian neurectomy, a posterior nasal neurectomy, a turbinate reduction, or any other suitable procedure. In some cases, a combination of loop electrode assembly (1140) and needle electrode assembly (1370) may be used to perform a turbinate reduction. Other suitable ways in which loop electrode assembly (1140) and/or needle electrode assembly (1370) may be used to apply RF energy to tissue will be apparent to those skilled in the art in view of the teachings herein.

While not shown, instrument (1300) may also include one or more position sensors that are operable to generate signals indicative of the position of loop electrode assembly (1140) and/or needle electrode assembly (1370), or some other component of instrument (1300), in three-dimensional space. Such a position sensor may be integrated directly into shaft assembly (1130) or elsewhere into instrument. In addition, or in the alternative, such a position sensor may be integrated into a guidewire or other component that is disposed in shaft assembly (1130). Such a position sensor may take the form of one or more coils that generate signals in response to the presence of an alternating magnetic field. The position data generated by such position signals may be processed by a system that provides a visual indication to the operator to show the operator where loop electrode assembly (1140) and/or needle electrode assembly (1370), or some other component of instrument (1300), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

XI. EXAMPLE OF RF ABLATION INSTRUMENT WITH BLUNT DISTAL TIP ELECTRODES AND NEEDLE ELECTRODES

Figure 25A:
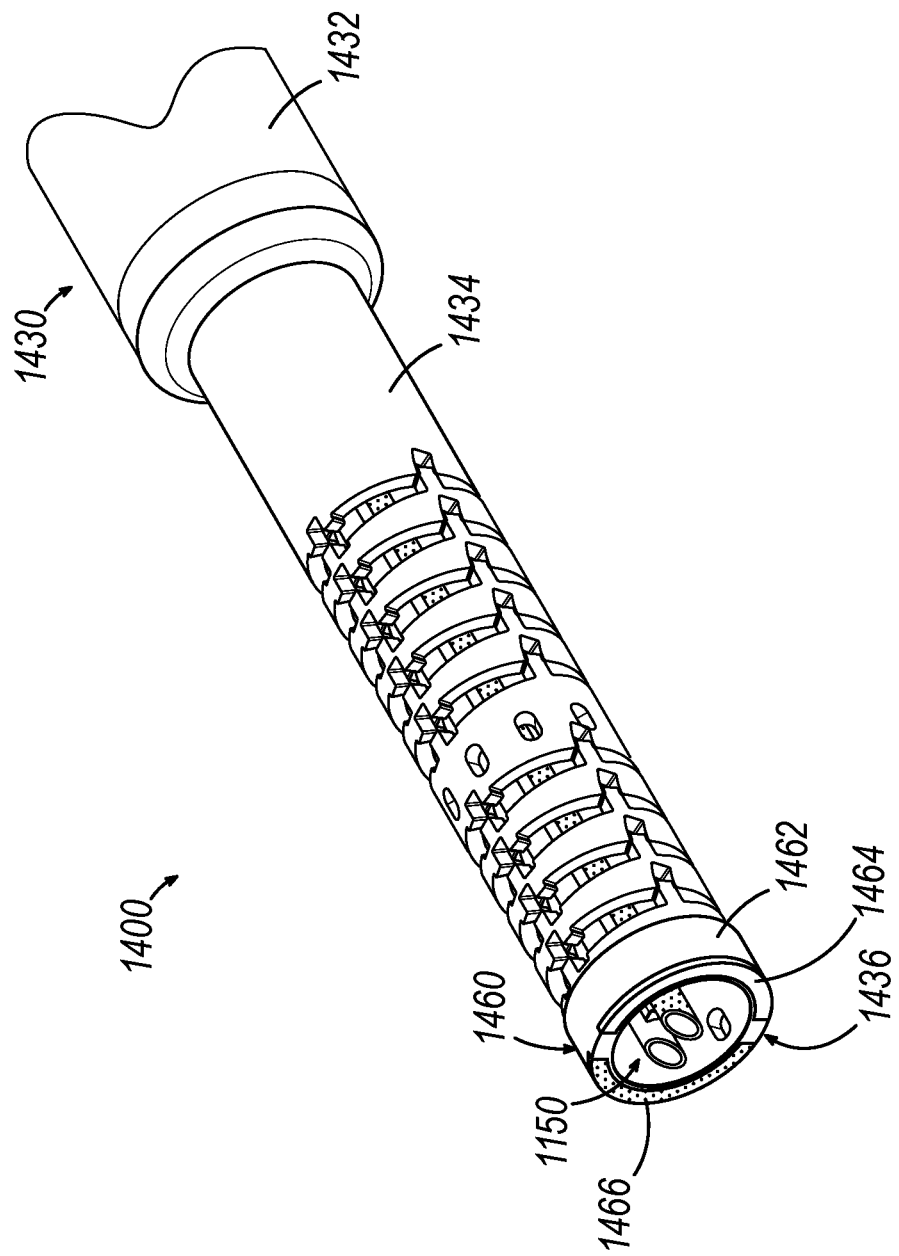
FIG. 25A depicts a perspective view of a distal portion of a shaft assembly of another example of an instrument that may be used to perform an ablation procedure in a nasal cavity, the instrument having a pair of distal tip electrodes, with a pair of needle electrodes of the instrument in a proximal retracted position relative to the shaft assembly.
Figure 25B:
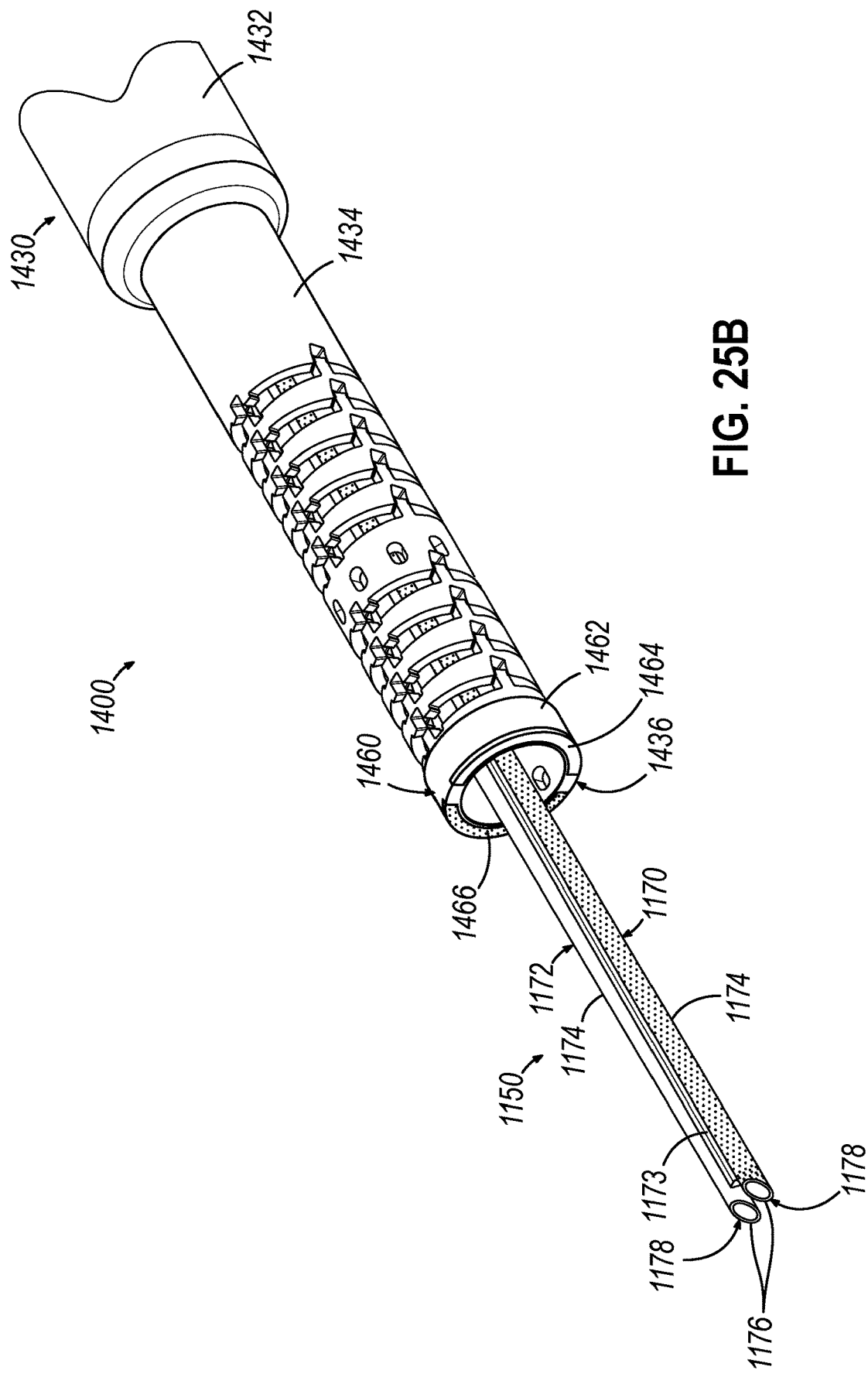
FIG. 25B depicts a perspective view of the distal portion of the shaft assembly of the instrument of FIG. 25A, with the pair of needle electrodes in a distal extended position relative to the shaft assembly.

FIGS. 25A-25B show a distal portion of another example of an instrument (1400) that may be used to deliver RF energy to tissue. For instance, instrument (1400) may be used to ablate a nerve (e.g., the posterior nasal nerve (40)), ablate a turbinate (e.g., any of turbinates (20, 22, 24)), or ablate, electroporate (e.g., to promote absorption of therapeutic agents, etc.), or apply resistive heating to any other kind of anatomical structure in the head of a patient. Instrument (1400) is substantially similar to instrument (1100) except as otherwise described herein. Instrument (1400) of this example includes handle assembly (1110), a shaft assembly (1430), and needle electrode assembly (1150). While needle electrode assembly (1150) is shown in the present example, instrument (1400) may alternatively include any other suitable type of needle electrode or needle electrode assembly, such as needle electrode assembly (1270) or needle electrode assembly (1370) discussed above. Instrument (1400) is coupled with RF generator (1102), which is operable to generate RF electrosurgical energy for delivery to tissue via electrodes (1170, 1172, 1464, 1466) as will be described in greater detail below. The transition from FIG. 25A to FIG. 25B shows needle electrode assembly (1150) being driven by slider (1122) from a proximal position to a distal position. Of course, handle assembly (1110) is just an illustrative example; and slider (1122) may be substituted with any other suitable kinds of structures to drive translation of needle electrode assembly (1150).

Shaft assembly (1430) of the present example includes a rigid portion (1432), a flexible portion (1434) distal to rigid portion (1432), and an open distal end (1436). A pull-wire (not shown) is coupled with flexible portion (1434) and with deflection control knob (1116) of handle assembly (1110) to impart steerability to shaft assembly (1430) as described above with respect to shaft assembly (1130). Shaft assembly (1430) may also be rotatable relative to handle assembly (1110), about the longitudinal axis of rigid portion (1432), as described above with respect to shaft assembly (1130).

Shaft assembly (1430) of this example further includes a generally ring-shaped, blunt distal tip electrode assembly (1460) positioned at open distal end (1436). Distal tip electrode assembly (1460) includes an annular tip body (1462) fixedly secured to flexible portion (1434) at open distal end (1436). In some versions, tip body (1462) comprises plastic and/or some other electrically insulative material while flexible portion (1434) comprises a metallic material. Distal tip electrode assembly (1460) of this example further includes a pair of arcuate conductive elements (1464, 1466) angularly spaced apart from each other on a distally-facing surface of tip body (1462). In the present example, conductive elements (1464, 1466) extend along a curve defined by a single radius. Conductive elements (1464, 1466) and tip body (1462) thus cooperate to define a generally circular shape. In some other versions, conductive elements (1464, 1466) and tip body (1462) cooperate to define a shape that is elliptical, oval-shaped, square, triangular, or otherwise non-circular. In the present example, the generally circular shape defined by conductive elements (1464, 1466) and tip body (1462) extends along a plane that is perpendicular to the longitudinal axis of shaft assembly (1430). In some other versions, the generally circular shape (or other non-circular shape) defined by conductive elements (1464, 1466) and tip body (1462) extends along a plane that is obliquely oriented or otherwise transverse to the longitudinal axis of shaft assembly (1430).

In some versions, conductive elements (1464, 1466) may each include any one or more of a conductive wire, plate, film, and/or coating, and may be formed of any suitable material or combination of materials including but not limited to metallic conductive materials such as copper, gold, steel, aluminum, silver, nitinol, etc. and/or non-metallic conductive materials such as conducting polymers, silicides, graphite, etc. Conductive elements (1464, 1466) may be secured to tip body (1462) is any suitable fashion, including but not limited to being secured via an adhesive, via vapor deposition, or otherwise. While two conductive (1464, 1466) elements are shown, any other suitable number of conductive elements (1464, 1466) may be provided. Each conductive element (1464, 1466) is coupled with a corresponding one or more wire(s), trace(s), and/or other conductive element(s) that electrically couple conductive elements (1464, 1466) with RF generator (1102).

In the present example, conductive element (1464) is configured to apply RF energy at a first polarity; while conductive element (1466) is configured to apply RF energy at a second polarity. Conductive elements (1464, 1466) thus serve as electrodes that are operable to apply bipolar RF energy to tissue contacting conductive elements (1464, 1466). Tip body (1462) may be formed of an electrically insulative material, such as a plastic material, that prevents short circuiting between conductive elements (1464, 1466) while mechanically securing conductive elements (1464, 1466) relative to each other in a spaced-apart relationship.

Distal tip electrode assembly (1460) and needle electrode assembly (1150) are operable to apply bipolar RF energy to tissue. For instance, conductive element (1466) may serve as an active electrode while conductive element (1464) may serve as a return electrode. In such versions, needle electrode (1172) may serve as a return electrode while needle electrode (1170) may serve as an active electrode. In this manner, needle electrode (1170) and conductive element (1464), which are each generally positioned on a first lateral side relative to barrier (1173), may cooperate with each other to provide bipolar RF energy to tissue between needle electrode (1170) and conductive element (1464). Likewise, needle electrode (1172) and conductive element (1466), which are each generally positioned on a second lateral side relative to barrier (1173), may cooperate with each other to provide bipolar RF energy to tissue between needle electrode (1172) and conductive element (1466).

During use of instrument (1400), the operator may press distal tip electrode assembly (1460) against the tissue that the operator wishes to ablate (or otherwise apply RF energy to), using a stamping type of motion. With the tissue adequately engaged by distal tip electrode assembly (1460), the operator may then activate RF generator (1102), with conductive elements (1464, 1466) of distal tip electrode assembly (1460) serving as electrodes applying bipolar RF energy to the tissue against which distal tip electrode assembly (1460) is pressed. This may provide ablation that is relatively shallow. In scenarios where the operator wishes to provide a relatively deep ablation, the operator may advance needle electrode assembly (1150) into tissue and activate needle electrode assembly (1150) to apply RF energy to the tissue in which needle electrode assembly (1150) is disposed. In scenarios where the operator wishes to apply volumetric ablation, the operator may activate at least one needle electrode (1170, 1172) of needle electrode assembly (1150) simultaneously with at least one conductive element (1464, 1466) of distal tip electrode assembly (1460). By way of further example only, instrument (1400) may be used to perform a vidian neurectomy, a posterior nasal neurectomy, a turbinate reduction, or any other suitable procedure. In some cases, a combination of distal tip electrode assembly (1460) and needle electrode assembly (1150) may be used to perform a turbinate reduction. Other suitable ways in which distal tip electrode assembly (1460) and/or needle electrode assembly (1150) may be used to apply RF energy to tissue will be apparent to those skilled in the art in view of the teachings herein.

While not shown, instrument (1400) may also include one or more position sensors that are operable to generate signals indicative of the position of distal tip electrode assembly (1460) and/or needle electrode assembly (1150), or some other component of instrument (1400), in three-dimensional space. Such a position sensor may be integrated directly into shaft assembly (1130) or elsewhere into instrument. In addition, or in the alternative, such a position sensor may be integrated into a guidewire or other component that is disposed in shaft assembly (1130). Such a position sensor may take the form of one or more coils that generate signals in response to the presence of an alternating magnetic field. The position data generated by such position signals may be processed by a system that provides a visual indication to the operator to show the operator where distal tip electrode assembly (1460) and/or needle electrode assembly (1150), or some other component of instrument (1400), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

XII. EXAMPLE OF RF ABLATION INSTRUMENT WITH BLUNT DISTAL TIP ELECTRODES AND NEEDLE ELECTRODES AND VISUALIZATION AND IRRIGATION ASSEMBLY

FIGS. 26-31 show a distal portion of another example of an instrument (1500) that may be used to deliver RF energy to tissue. For instance, instrument (1500) may be used to ablate a nerve (e.g., the posterior nasal nerve (40)), ablate a turbinate (e.g., any of turbinates (20, 22, 24)), or ablate, electroporate (e.g., to promote absorption of therapeutic agents, etc.), or apply resistive heating to any other kind of anatomical structure in the head of a patient. Instrument (1500) is substantially similar to instrument (1100) except as otherwise described herein. Instrument (1500) of this example includes handle assembly (1110), a shaft assembly (1510), a distal tip electrode assembly (1530), and a visualization and irrigation assembly (1700). Instrument (1500) is coupled with RF generator (1102), which is operable to generate RF electrosurgical energy for delivery to tissue via electrodes (1540, 1550) as will be described in greater detail below. While instrument (1500) is described as including handle assembly (1110) in this example, handle assembly (1110) is just an illustrative example; and shaft assembly (1510) may extend from any other suitable kind of body.

Shaft assembly (1510) of the present example includes a rigid proximal portion (1512), a flexible portion (1514) distal to rigid proximal portion (1512), a rigid distal portion (1516) distal to flexible portion (1514), and an open distal end (1518). A pull-wire (not shown) is coupled with flexible portion (1514) and with deflection control knob (1116) of handle assembly (1110) to impart steerability to shaft assembly (1510) as described above with respect to shaft assembly (1130). Shaft assembly (1510) may also be rotatable relative to handle assembly (1110), about the longitudinal axis of rigid proximal portion (1512), as described above with respect to shaft assembly (1130).

Shaft assembly (1510) of this example further includes a generally ring-shaped, blunt distal tip electrode assembly (1530) positioned at open distal end (1518). Distal tip electrode assembly (1530) includes an annular tip body (1520) fixedly secured to rigid distal portion (1516) at open distal end (1518). In some versions, tip body (1520) comprises plastic and/or some other electrically insulative material while rigid distal portion (1516) comprises a metallic material. Distal tip electrode assembly (1530) of this example further includes a pair of arcuate conductive elements (1540, 1550) angularly spaced apart from each other on a distally-facing surface of tip body (1520). In the present example, conductive elements (1540, 1550) extend along a curve defined by a single radius. Conductive elements (1540, 1550) and tip body (1520) thus cooperate to define a generally circular shape. In some other versions, conductive elements (1540, 1550) and tip body (1520) cooperate to define a shape that is elliptical, oval-shaped, square, triangular, or otherwise non-circular. In the present example, the generally circular shape defined by conductive elements (1540, 1550) and tip body (1520) extends along a plane that is perpendicular to the longitudinal axis of shaft assembly (1510). In some other versions, the generally circular shape (or other non-circular shape) defined by conductive elements (1540, 1550) and tip body (1520) extends along a plane that is obliquely oriented or otherwise transverse to the longitudinal axis of shaft assembly (1510).

In some versions, conductive elements (1540, 1550) may each include any one or more of a conductive wire, plate, film, and/or coating, and may be formed of any suitable material or combination of materials including but not limited to metallic conductive materials such as copper, gold, steel, aluminum, silver, nitinol, etc. and/or non-metallic conductive materials such as conducting polymers, silicides, graphite, etc. Conductive elements (1540, 1550) may be secured to tip body (1520) is any suitable fashion, including but not limited to being secured via an adhesive, via vapor deposition, or otherwise. Conductive element (1540) of the present example includes a distally-facing, circumferentially-extending portion (1542), an inwardly-facing, circumferentially-extending portion (1544), and an outwardly-facing, circumferentially-extending portion (1546). Similarly, conductive element (1550) of the present example includes a distally-facing, circumferentially-extending portion (1552), an inwardly-facing, circumferentially-extending portion (1554), and an outwardly-facing, circumferentially-extending portion (1556). While two conductive elements (1540, 1550) are shown, any other suitable number of conductive elements (1540, 1550) may be provided. Each conductive element (1540, 1550) is coupled with a corresponding one or more wire(s), trace(s), and/or other conductive element(s) that electrically couple conductive elements (1540, 1550) with RF generator (1102).

In some versions, conductive elements (1540, 1550) are substantially flush with the outer surface of tip body (1520). In some other versions, conductive elements (1540, 1550) are proud relative to the outer surface of tip body (1520). In some other versions, conductive elements (1540, 1550) are recessed relative to the outer surface of tip body (1520).

In the present example, conductive element (1540) is configured to apply RF energy at a first polarity; while conductive element (1550) is configured to apply RF energy at a second polarity. Conductive elements (1540, 1550) thus serve as electrodes that are operable to apply bipolar RF energy to tissue contacting conductive elements (1540, 1550). By way of example only, conductive element (1540) may serve as an active electrode while conductive element (1550) may serve as a return electrode. Tip body (1520) may be formed of an electrically insulative material, such as a plastic material, that prevents short circuiting between conductive elements (1540, 1550) while mechanically securing conductive elements (1540, 1550) relative to each other in a spaced-apart relationship. With this spacing maintained by tip body (1520), a first angular gap (1532) is defined between respective first free ends of conductive elements (1540, 1550); while a second angular gap (1534) is defined between respective second free ends of conductive elements (1540, 1550). Gaps (1532, 1534) are angularly offset from each other by approximately 180 degrees in the present example.

While distal tip electrode assembly (1530) is operable to apply bipolar RF energy to tissue in the present example, other instrumentation may be used in combination with instrument (1500) to ablate tissue. By way of example only, any of the various needle electrodes described herein and/or other electrode assemblies may be advanced along a working channel (1560) defined by shaft assembly (1510) to ablate tissue. Such ancillary ablation instrumentation may be used in combination with, or in lieu of, distal tip electrode assembly (1530).

During use of instrument (1500), the operator may press distal tip electrode assembly (1530) against the tissue that the operator wishes to ablate (or otherwise apply RF energy to), using a stamping type of motion. With the tissue adequately engaged by distal tip electrode assembly (1530), the operator may then activate RF generator (1102), with conductive elements (1540, 1550) of distal tip electrode assembly (1530) serving as electrodes applying bipolar RF energy to the tissue against which distal tip electrode assembly (1530) is pressed. This may provide ablation that is relatively shallow. In scenarios where the operator wishes to provide a relatively deep ablation, the operator may advance a needle electrode assembly via working channel (1560) into tissue and activate the needle electrode assembly to apply RF energy to the tissue in which the needle electrode assembly is disposed. In scenarios where the operator wishes to apply volumetric ablation, the operator may activate at least one needle electrode (e.g., at least one needle electrode extending distally from working channel (1560), etc.) simultaneously with at least one conductive element (1540, 1550) of distal tip electrode assembly (1530). By way of further example only, instrument (1500) may be used to perform a vidian neurectomy, a posterior nasal neurectomy, a turbinate reduction, or any other suitable procedure. In some cases, a combination of distal tip electrode assembly (1530) and some other electrode assembly (e.g., an electrode assembly disposed in working channel (1560), etc.) may be used to perform a turbinate reduction. Other suitable ways in which distal tip electrode assembly (1530) may be used to apply RF energy to tissue will be apparent to those skilled in the art in view of the teachings herein.

Figure 27:
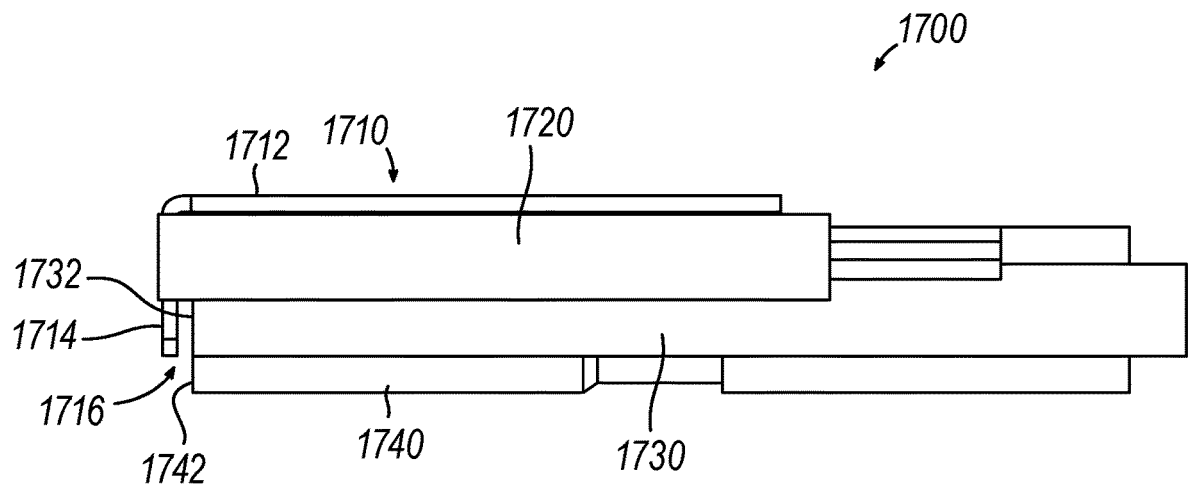
FIG. 27 depicts a side elevation view of a visualization and irrigation assembly of the instrument of FIG. 26.
Figure 28:
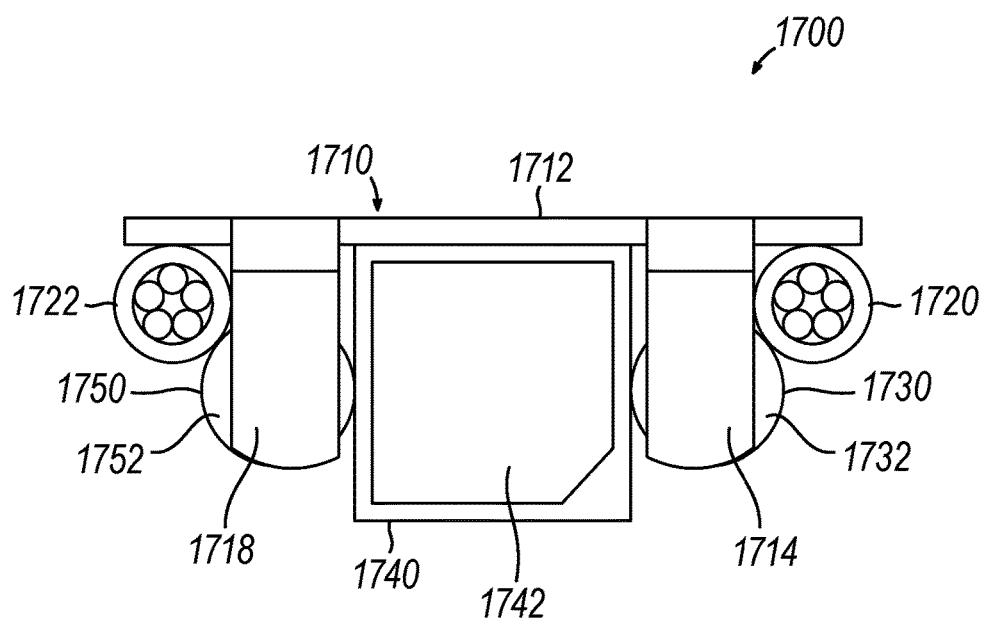
FIG. 28 depicts a front elevation view of the visualization and irrigation assembly of FIG. 27.
Figure 29:
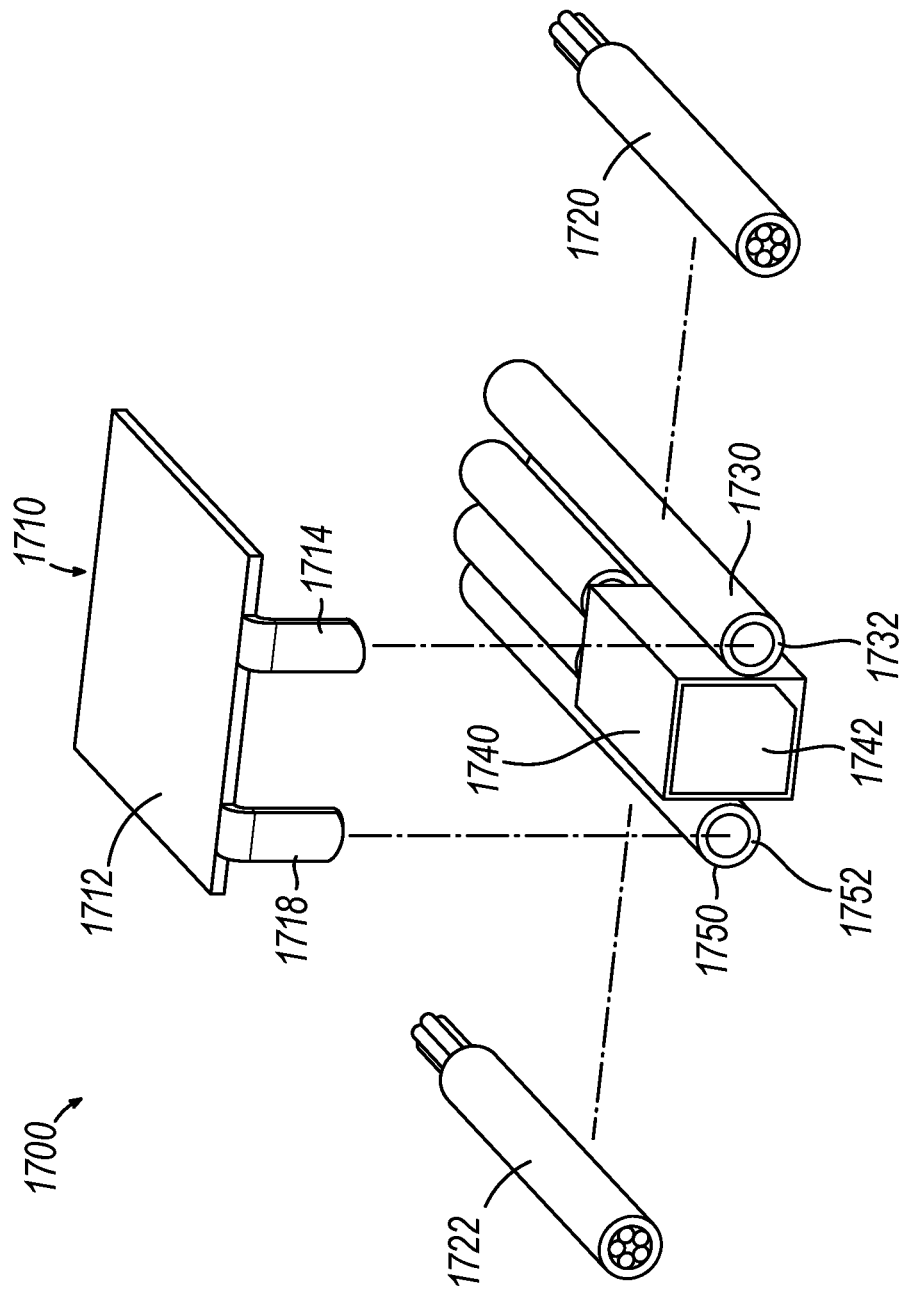
FIG. 29 depicts an exploded perspective view of the visualization and irrigation assembly of FIG. 27.

As noted above, instrument (1500) of the present example further includes visualization and irrigation assembly (1700), which is disposed within shaft assembly (1510). Visualization and irrigation assembly (1700) is operable to provide visualization and irrigation at a target tissue site distal to distal end (1518) of shaft assembly (1510). As best seen in FIGS. 27-29, visualization and irrigation assembly (1700) of this example includes a plate member (1710), a camera (1740), a pair of illuminating elements (1720, 1722), and a pair of fluid conduits (1730, 1750). Camera (1740) may be in the form of a camera that is suitably sized to fit within shaft assembly (1510) while still permitting space for a working channel (1560) to extend along shaft assembly (1510), thereby permitting additional instrumentation, suction, fluids, etc. to pass through open distal end (1518) adjacent to camera (1740).

Illuminating elements (1720, 1722) are configured and operable to illuminate the field of view of camera (1740). As best seen in FIG. 28, illuminating element (1720) is positioned at one lateral side of camera (1740) while illuminating element (1722) is positioned at the other lateral side of camera (1740). While two illuminating elements (1720, 1722) are used in the present example, other versions may employ just one illuminating element (1720, 1722) or more than two illuminating elements (1720, 1722). In the present example, illuminating elements (1720, 1722) include LEDs. In some other versions, illuminating elements (1720, 1722) include fiber optic components. For instance, each illuminating element (1720, 1722) may include a lens that is optically coupled with one or more respective optical fibers or optical fiber bundles. Such optical fibers or optical fiber bundles may extend along shaft assembly (1510) and be optically coupled with a source of light that is either integrated into handle assembly (1110) (or some other body from which shaft assembly (1510) extends) or otherwise provided.

Regardless of the form taken by illuminating elements (1720, 1722), in some versions illuminating elements (1720, 1722) are driven to emit light at one or more wavelengths selected to facilitate visualization of a tissue state. For instance, one or both of illuminating elements (1720, 1722) may be driven to emit light at a wavelength associated with the color of tissue that has been sufficiently ablated. In some such versions, the light may provide visual emphasis to the operator to assist the operator in visually confirming that the ablation is complete. In addition, or in the alternative, one or both of illuminating elements (1720, 1722) may be driven to emit light at a wavelength associated with the color of tissue that should be ablated. As another example, some versions may provide selectable variation of the wavelength of light emitted by one or both of illuminating elements (1720, 1722), such that the wavelength may be varied based on operator selection and/or based on the stage of the procedure. For instance, one or more sensors (e.g., tissue impedance detectors, thermistors, etc.) may provide real-time feedback on the state of the target tissue; and this feedback may be used to automatically vary the wavelength of light emitted by one or both of illuminating elements (1720, 1722). Alternatively, the light emitted by one or both of illuminating elements (1720, 1722) may have any other suitable properties.

Conduits (1730, 1750) laterally flank camera (1740) in this example. In particular, conduit (1730) is positioned outboard relative to camera (1740) while being positioned inboard relative to illuminating element (1720). Conduit (1750) is positioned outboard relative to camera (1740) while being positioned inboard relative to illuminating element (1722). In some versions, both conduits (1730, 1750) are in fluid communication with a source of liquid (e.g., saline, etc.). In some other versions, both conduits (1730, 1750) are in fluid communication with a source of suction. In some other versions, one conduit (1730 or 1750) is in fluid communication with a source of liquid while the other conduit (1750 or 1730) is in fluid communication with a source of suction. In still other versions, one or both of conduits (1730, 1750) may be in fluid communication with a valve assembly, where the valve assembly is coupled with a source of liquid and a source of suction. In such versions, the valve assembly may be used to selectively couple one or both of conduits (1730, 1750) with the source of liquid or the source of suction. Various suitable ways in which either or both of conduits (1730, 1750) may be coupled with a source of liquid and/or a source of suction will be apparent to those skilled in the art in view of the teachings herein.

In versions where at least one of conduits (1730, 1750) is in communication with a source of liquid, such conduit(s) (1730, 1750) may be used to deliver such liquid to the distal end (1742) of camera (1740). By flushing distal end (1742) with liquid, conduits (1730, 1750) may be used to keep distal end (1742) clear of debris and thereby maintain appropriate visualization via camera (1740). When distal tip electrode assembly (1530) is being used to apply RF energy to tissue, liquid expelled via one or both of conduits (1730, 1750) may also assist in promoting electrical continuity and reduce impedance at the target ablation site, thereby promoting suitable ablation. Thus, liquid expelled via one or both of conduits (1730, 1750) may simultaneously or sequentially promote visualization and ablation.

In versions where at least one of conduits (1730, 1750) is in communication with a source of suction, such conduit(s) (1730, 1750) may be used to draw away excess liquids (e.g., liquid expelled via the other conduit (1730), etc.). In addition, or in the alternative, suction may be applied via one or both of conduits (1730, 1750) to aspirate smoke, vapor, and/or other aspiratable results from a tissue ablation process. Such aspiration may further promote visualization during and after the ablation process by helping to clear the visual field of view for camera (1740).

Plate member (1710) of this example includes a plate (1712) and a pair of transversely extending tabs (1714, 1718). Plate (1712) is positioned over camera (1740) and may thus serve to shied camera (1740) from getting snagged and perhaps damaged by other instruments that are advanced along working channel (1560). Tabs (1714, 1718) are positioned to correspond with the locations of respective distal ends (1732, 1752) of conduits (1730, 1750). In particular, as best seen in FIG. 28, tab (1714) is positioned just distal to distal end (1732) of conduit (1730); while tab (1718) is positioned just distal to distal end (1752) of conduit (1750). As best seen in FIG. 27, tab (1714) is further positioned to leave a gap (1716) between the proximal face of tab (1714) and distal end (1732) of conduit (1730). While not shown, a similar gap may be left between the proximal face of tab (1718) and distal end (1752) of conduit (1750). These gaps (1716) may be sized to allow liquid to escape from distal ends (1732, 1752); and to allow suction to be applied via distal ends (1732, 1752). However, the presence of tabs (1714, 1718) may assist in diverting liquid expelled via distal ends (1732, 1752) toward distal end (1742) of camera (1740). In other words, when liquid is conveyed along either or both of conduits (1730, 1750), and such liquid exits the distal end(s) (1732, 1752) of such conduit(s) (1730, 1750), the corresponding tab(s) (1714, 1718) may divert the expelled liquid toward distal end (1742) of camera (1740) and thereby assist in flushing debris away from camera (1740). In some other versions, tabs (1714, 1718) are omitted. Plate member (1710) is merely optional.

In addition to the foregoing, at least part of visualization and irrigation assembly (1700) and/or other components of instrument (1500) may be configured and operable in accordance with at least some of the teachings of U.S. Provisional Pat. App. No. 63/037,640, entitled "ENT Guide with Advanceable Instrument and Advanceable Endoscope Shaft," filed Jun. 11, 2020, the disclosure of which is incorporated by reference herein, in its entirety.

In some versions, instrument (1500) is operable to provide relative translation between distal end (1518) of shaft assembly (1510) and visualization and irrigation assembly (1700). In some such versions, distal end (1518) of shaft assembly (1510) is operable to translate longitudinally relative to handle assembly (1110) or some other body from which shaft assembly (1510) extends; while visualization and irrigation assembly (1700) remains longitudinally stationary relative to handle assembly (1110) or some other body from which shaft assembly (1510) extends. In some other versions, visualization and irrigation assembly (1700) is operable to translate longitudinally relative to handle assembly (1110) or some other body from which shaft assembly (1510) extends; while distal end (1518) of shaft assembly (1510) remains longitudinally stationary relative to handle assembly (1110) or some other body from which shaft assembly (1510) extends. In either case, the relative longitudinal movement between distal end (1518) of shaft assembly (1510) and visualization and irrigation assembly (1700) may enable the operator to more readily visualize a tissue region that is targeted for ablation before the ablation occurs, visualize the targeted tissue region during ablation, and/or visualize the targeted tissue region after ablation.

Figure 26:
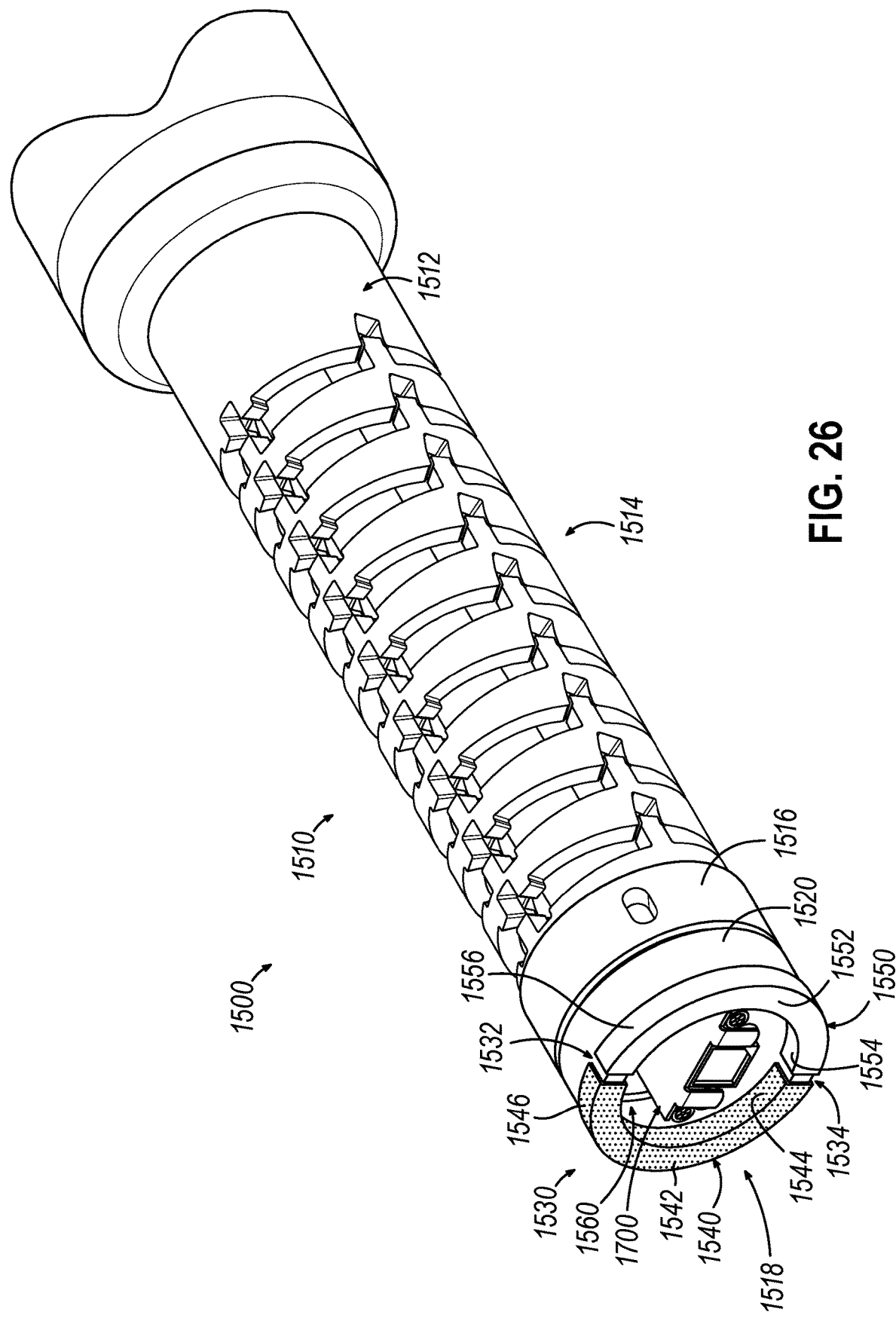
FIG. 26 depicts a perspective view of a distal portion of a shaft assembly of another example of an instrument that may be used to perform an ablation procedure in a nasal cavity.
Figure 30:
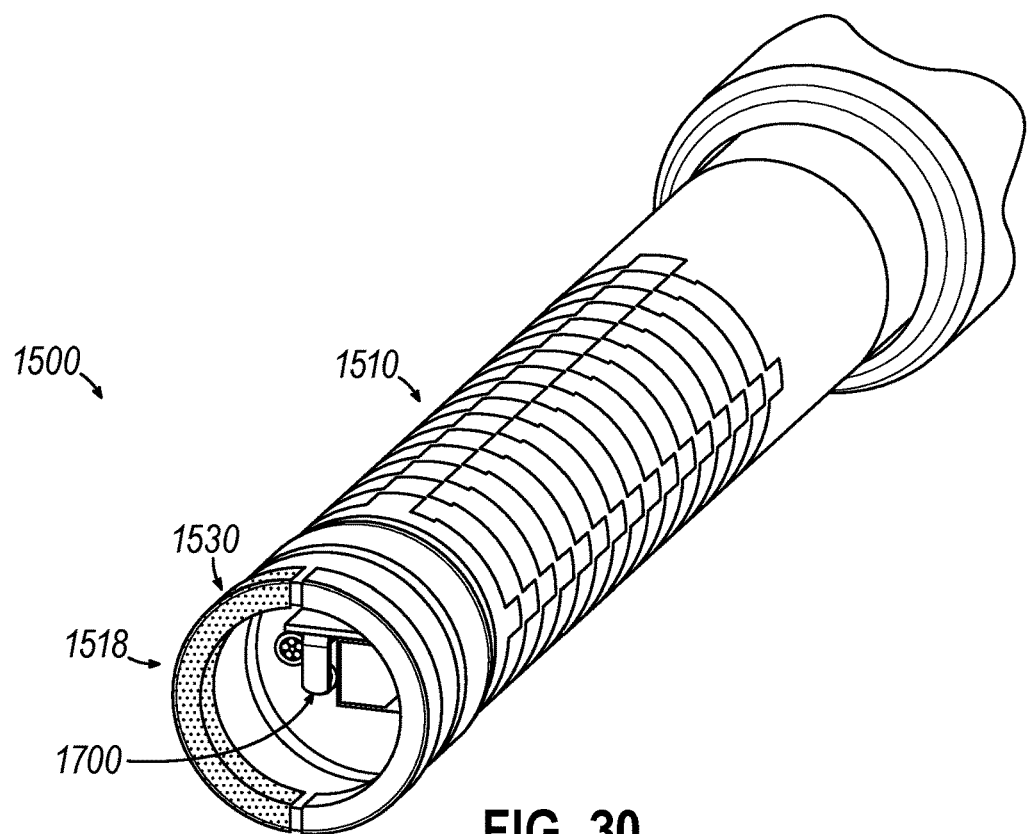
FIG. 30 depicts a perspective view of the distal portion of the shaft assembly of the instrument of FIG. 26, with the visualization and irrigation assembly of FIG. 27 in a proximal position relative to the distal end of the shaft assembly.
Figure 31:
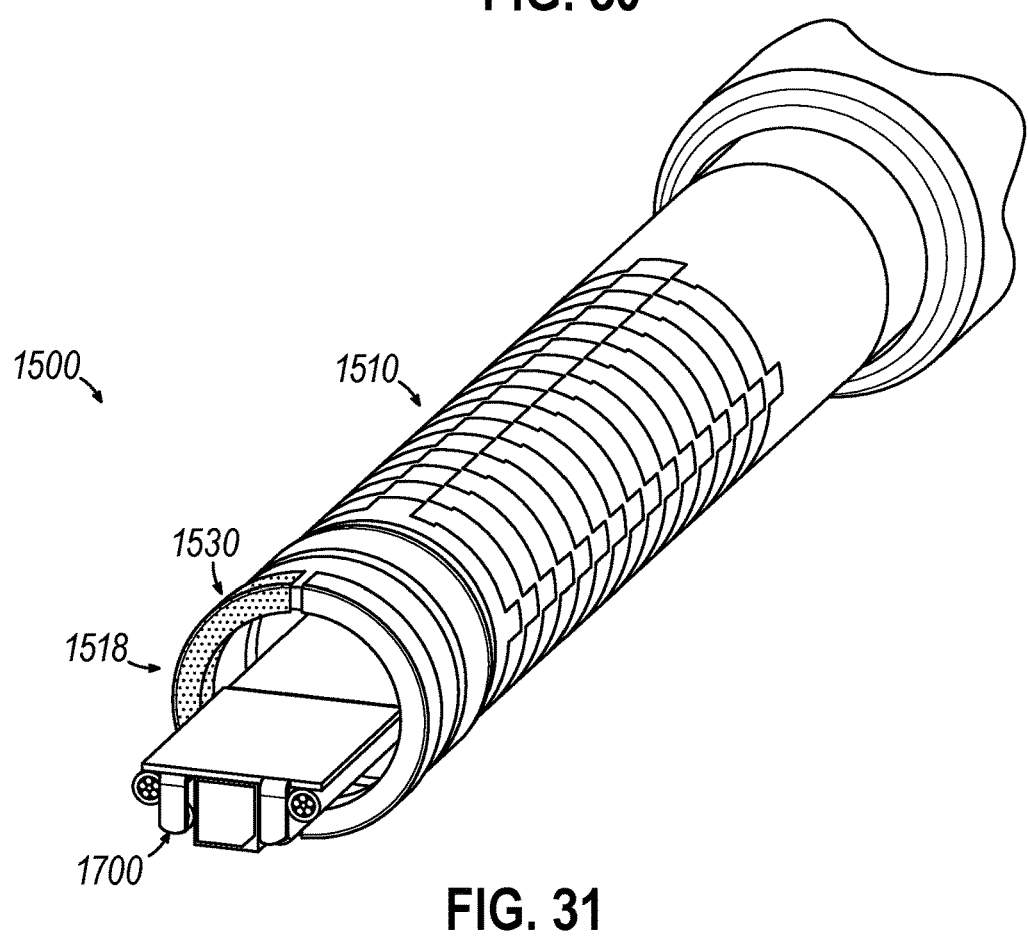
FIG. 31 depicts a perspective view of the distal portion of the shaft assembly of the instrument of FIG. 26, with the visualization and irrigation assembly of FIG. 27 in a distal position relative to the distal end of the shaft assembly.

In versions permitting relative longitudinal movement between distal end (1518) of shaft assembly (1510) and visualization and irrigation assembly (1700), an operator may wish to have distal end (1518) of shaft assembly (1510) and visualization and irrigation assembly (1700) at substantially the same longitudinal position, as shown in FIG. 26, while the operator maneuvers distal end (1518) toward the targeted tissue region. Once the operator reaches the targeted tissue region and presses distal tip electrode assembly (1530) against the targeted tissue, the operator may wish to have visualization and irrigation assembly (1700) retracted proximally relative to distal end (1518) of shaft assembly (1510), as shown in FIG. 30, while applying the RF energy to the tissue via distal tip electrode assembly (1530). Once the operator believes that the ablation is complete, the operator may wish to have visualization and irrigation assembly (1700) advanced distally relative to distal end (1518) of shaft assembly (1510), as shown in FIG. 31, to better visualize the ablated tissue to confirm that they are satisfied with the ablation. Other suitable ways in which an operator may wish to utilize instrument (1500) with visualization and irrigation assembly (1700) at different longitudinal positions relative to distal end (1518) of shaft assembly (1510) will be apparent to those skilled in the art in view of the teachings herein. Similarly, various suitable actuators and mechanisms, etc., that may be used to provide relative longitudinal movement between distal end (1518) of shaft assembly (1510) and visualization and irrigation assembly (1700) will be apparent to those skilled in the art in view of the teachings herein.

As another merely illustrative example, instrument (1500) may be configured and operable such that conductive elements (1540, 1550) are operable to translate longitudinally relative to tip body (1520).

In versions that provide longitudinal movement of visualization and irrigation assembly (1700) relative to handle assembly (1110) (or relative to whatever body from which shaft assembly (1510) extends), it may be necessary to account for such movement in or relative to wires, traces, or other electrically conductive paths that couple camera (1740) with an image processor that is also coupled with handle assembly (1110) (or some other body from which shaft assembly (1510) extends). In versions where illuminating elements (1720, 1722) include LEDs, it may also be necessary to account for longitudinal movement in or relative to wires, traces, or other electrically conductive paths that couple LEDs of illuminating elements (1720, 1722) with a power source that is also coupled with handle assembly (1110) (or some other body from which shaft assembly (1510) extends). Even in scenarios where visualization and irrigation assembly (1700) is longitudinally fixed within shaft assembly (1510), there may still be a need to account for longitudinal movement in or relative to wires, traces, or other electrically conductive paths that couple electrical components of visualization and irrigation assembly (1700) with other components that are coupled with handle assembly (1110) (or some other body from which shaft assembly (1510) extends). For instance, such longitudinal movement may occur when flexible portion (1514) is deflected laterally relative to the longitudinal axis of rigid portion (1512), as such deflection may lengthen or shorten the effective length between visualization and irrigation assembly (1700) and handle assembly (1110) (or some other body from which shaft assembly (1510) extends). By way of example only, the electrical path(s) between electrical components of visualization and irrigation assembly (1700) and other components that are coupled with handle assembly (1110) (or some other body from which shaft assembly (1510) extends) may include sliding slip couplings, service loops, extensible features, or other features that are configured to maintain electrical continuity while permitting relative longitudinal movement between components of the circuit. By way of further example only, an extensible circuit component may include an extensible flex-circuit substrate with one or more traces formed thereon, where the one or more traces have a zigzag or wave shape that allows the traces to effectively expand as the extensible flex-circuit substrate stretches longitudinally.

While not shown, instrument (1500) may also include one or more position sensors that are operable to generate signals indicative of the position of distal tip electrode assembly (1530) and/or visualization and irrigation assembly (1700), or some other component of instrument (1500), in three-dimensional space. Such a position sensor may be integrated directly into shaft assembly (1510) or elsewhere into instrument. In addition, or in the alternative, such a position sensor may be integrated into a guidewire or other component that is disposed in shaft assembly (1510). Such a position sensor may take the form of one or more coils that generate signals in response to the presence of an alternating magnetic field. The position data generated by such position signals may be processed by a system that provides a visual indication to the operator to show the operator where distal tip electrode assembly (1530) and/or visualization and irrigation assembly (1700), or some other component of instrument (1500), is located within the patient in real time. Such a visual indication may be provided as an overlay on one or more preoperatively obtained images (e.g., CT scans) of the patient's anatomy. Such position sensing and navigation capabilities may be provided in accordance with at least some of the teachings of the various references cited herein.

XIII. EXAMPLE OF RF ABLATION INSTRUMENT WITH BLUNT DISTAL TIP ELECTRODES AND NON-CONDUCTIVE NEEDLE

Figure 32:
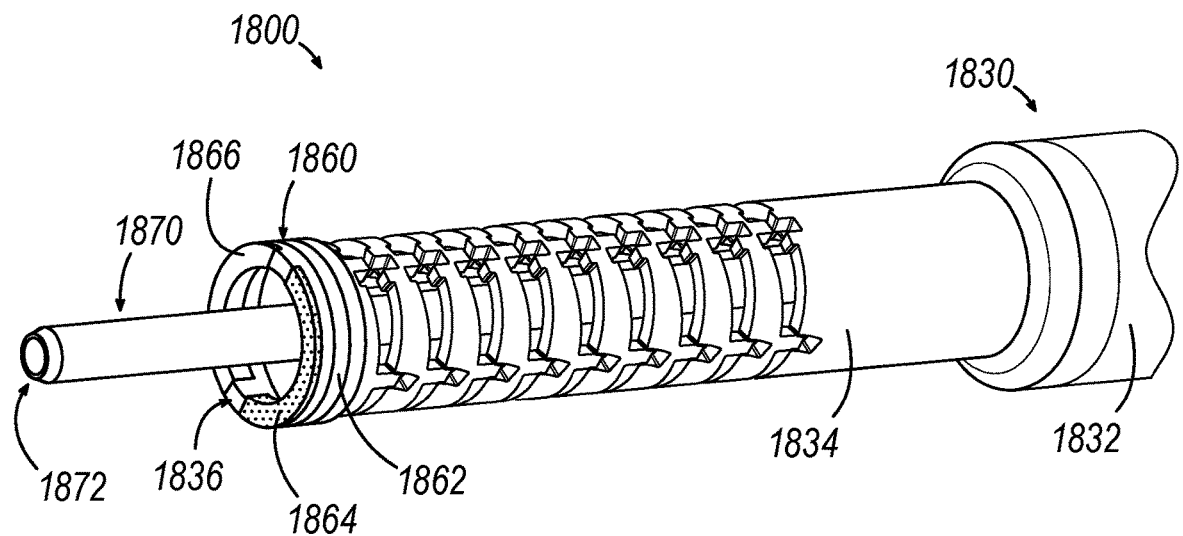
FIG. 32 depicts a perspective view of a distal portion of a shaft assembly of another example of an instrument that may be used to perform an ablation procedure in a nasal cavity, the instrument having a pair of distal tip electrodes, with a non-conductive needle of the instrument in a distal extended position relative to the distal end of the shaft assembly.

FIG. 32 shows a distal portion of another example of an instrument (1800) that may be used to deliver RF energy to tissue. Instrument (1800) is substantially similar to instrument (1100) except as otherwise described herein. Instrument (1800) of this example includes handle assembly (1110), a shaft assembly (1830), and an electrically non-conductive (e.g., insulative) needle (1870). FIG. 32 shows needle (1870) having been driven by slider (1122) from a proximal position to a distal position. By way of example only, needle (1870) may be used to perform a core biopsy, deliver therapeutic agent, or perform any other suitable function as will be apparent to those skilled in the art in view of the teachings herein. Needle (1870) may include a sharpened distal tip (e.g., annular blade) (1872) to promote penetration of tissue by needle (1870).

Shaft assembly (1830) of the present example includes a rigid portion (1832), a flexible portion (1834) distal to rigid portion (1832), and an open distal end (1836). Shaft assembly (1830) of this example further includes a generally ring-shaped, blunt distal tip electrode assembly (1860) positioned at open distal end (1836). Distal tip electrode assembly (1860) includes an annular tip body (1862) fixedly secured to flexible portion (1834) at open distal end (1836). Distal tip electrode assembly (1860) of this example further includes a pair of arcuate conductive elements (1864, 1866) angularly spaced apart from each other on a distally-facing surface of tip body (1862). In some versions, conductive elements (1864, 1866) are configured to apply RF energy at first and second polarities, respectively, to serve as electrodes that are operable to apply bipolar RF energy to tissue contacting conductive elements (1864, 1866).

XIV. EXAMPLE OF RF ABLATION INSTRUMENT WITH BLUNT DISTAL TIP ELECTRODES AND SPLAYED NEEDLE ELECTRODES

Figure 33:
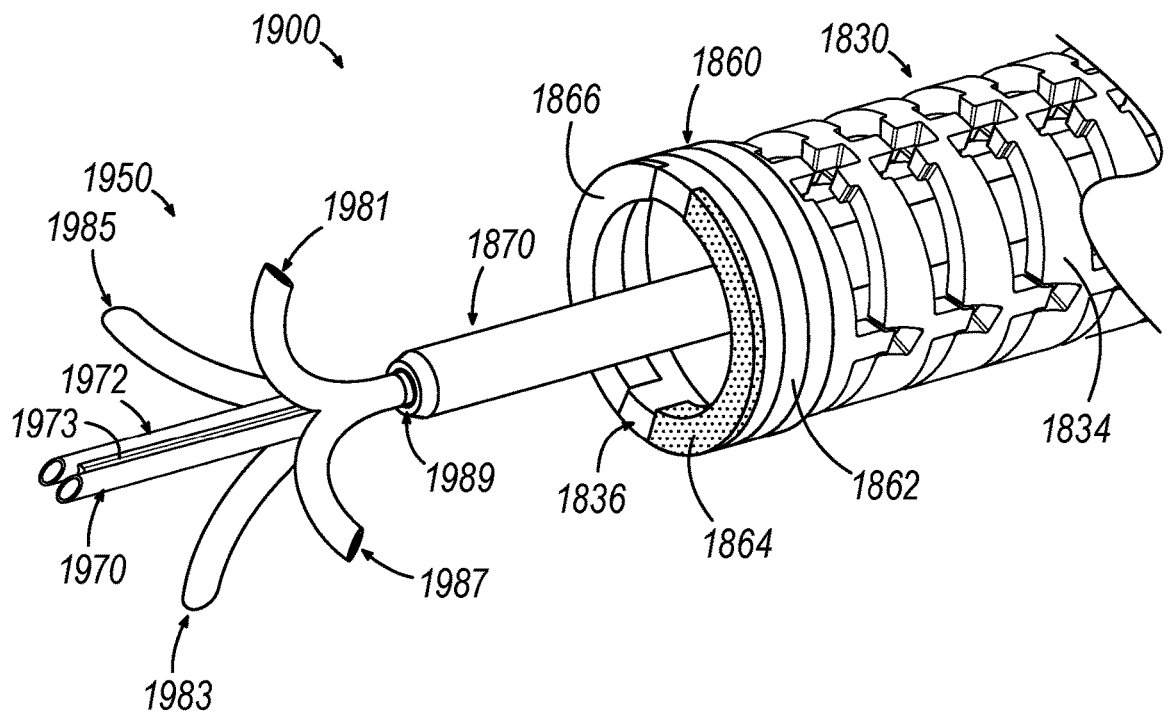
FIG. 33 depicts a perspective view of a distal portion of a shaft assembly of another example of an instrument that may be used to perform an ablation procedure in a nasal cavity, the instrument having a pair of distal tip electrodes, with a plurality of conductive needles of the instrument in a distal extended position relative to the distal end of the shaft assembly.

FIG. 33 shows a distal portion of another example of an instrument (1900) that may be used to deliver RF energy to tissue. Instrument (1900) is substantially similar to instrument (1100) except as otherwise described herein. Instrument (1900) of this example includes handle assembly (1110), shaft assembly (1830), and a needle electrode assembly (1950) extendable from and retractable into electrically non-conductive needle (1870). FIG. 33 shows needle electrode assembly (1950) having been driven by slider (1122) from a proximal position to a distal position. Needle electrode assembly (1950) of the present example includes a pair of straight needle electrodes (1970, 1972) that are fixed longitudinally relative to each other by a barrier (1973) and configured to extend along or parallel to the longitudinal axis of shaft assembly (1830) when straight needle electrodes (1970, 1972) are distally positioned as shown in FIG. 33. Needle electrode assembly (1950) of the present example further includes a plurality of oblique needle electrodes (1981, 1983, 1985, 1987) that are resiliently biased to splay outwardly relative to the longitudinal axis of shaft assembly (1830) when oblique needle electrodes (1981, 1983, 1985, 1987) are distally positioned as shown in FIG. 33. By way of example only, such biasing and/or outward splaying of oblique needle electrodes (1981, 1983, 1985, 1987) may be provided in accordance with at least some of the teachings of U.S. Pat. App. No. 63/067,495, entitled "ENT Ablation Instrument with Electrode Loop," filed Aug. 19, 2020, the disclosure of which is incorporated by reference herein, in its entirety.

In the example shown, proximal portions of needle electrodes (1970, 1972, 1981, 1983, 1985, 1987) are secured to each other within a collar (1989). In some versions, needle electrodes (1970, 1981, 1983) are configured to apply RF energy at a first polarity and needle electrodes (1972, 1985, 1987) are configured to apply RF energy at a second polarity, to serve as electrodes that are operable to apply bipolar RF energy to tissue penetrated by needle electrodes (1970, 1972, 1981, 1983, 1985, 1987) (e.g., by cooperating with each other and/or with conductive elements (1864, 1866)).

XV. EXAMPLE OF RF ABLATION INSTRUMENT WITH BLUNT DISTAL TIP ELECTRODES, SPLAYED NEEDLE ELECTRODES, AND VISUALIZATION AND IRRIGATION ASSEMBLY

Figure 34:
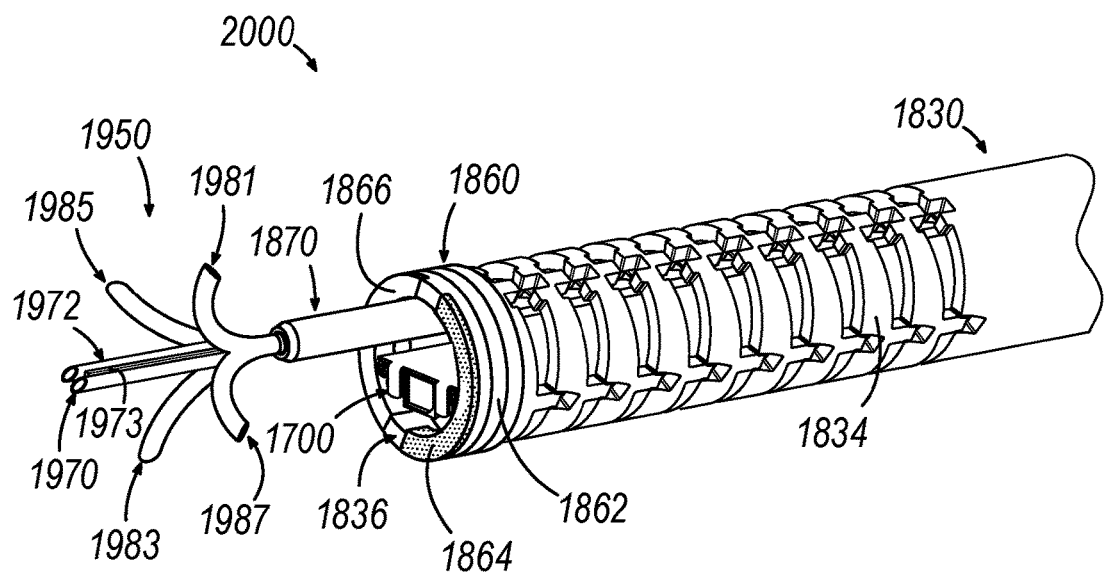
FIG. 34 depicts a perspective view of a distal portion of a shaft assembly of another example of an instrument that may be used to perform an ablation procedure in a nasal cavity, the instrument having a pair of distal tip electrodes and a visualization and irrigation assembly, with a plurality of conductive needles of the instrument in a distal extended position relative to the distal end of the shaft assembly.

FIG. 34 shows a distal portion of another example of an instrument (2000)) that may be used to deliver RF energy to tissue. Instrument (2000)) is substantially similar to instrument (1100) except as otherwise described herein. Instrument (2000)) of this example includes handle assembly (1110), shaft assembly (1830), needle electrode assembly (1950) extendable from and retractable into electrically non-conductive needle (1870), and visualization and irrigation assembly (1700). FIG. 34 shows needle electrode assembly (1950) having been driven by slider (1122) from a proximal position to a distal position. Needle electrode assembly (1950) shown in FIG. 34 may be configured and operable just like needle electrode assembly (1950) shown in FIG. 33 and described above. Visualization and irrigation assembly (1700) shown in FIG. 34 may be configured and operable just like visualization and irrigation assembly (1700) shown in FIGS. 26-31 and described above. In versions where visualization and irrigation assembly (1700) is translatable relative to the rest of shaft assembly (1830), visualization and irrigation assembly (1700) may be translatable relative to the rest of shaft assembly (1830) independently of needle electrode assembly (1950) translating relative to the rest of shaft assembly (1830).

XVI. EXAMPLE OF RF ABLATION INSTRUMENT WITH BLUNT DISTAL TIP ELECTRODES, DILATION ASSEMBLY, AND VISUALIZATION AND IRRIGATION ASSEMBLY

Figure 35:
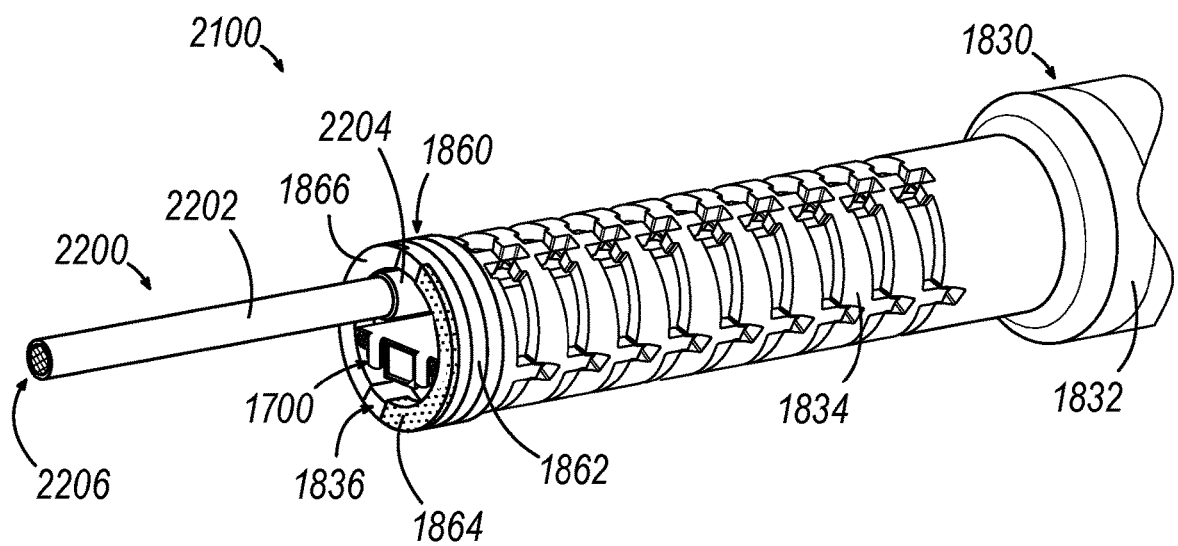
FIG. 35 depicts a perspective view of a distal portion of a shaft assembly of another example of an instrument that may be used to perform an ablation procedure in a nasal cavity, the instrument having a pair of distal tip electrodes and a visualization and irrigation assembly, with an inflatable balloon of the instrument in a distal extended position relative to the distal end of the shaft assembly.

FIG. 35 shows a distal portion of another example of an instrument (2100)) that may be used to deliver RF energy to tissue. Instrument (2100)) is substantially similar to instrument (1100) except as otherwise described herein. Instrument (2100)) of this example includes handle assembly (1110), shaft assembly (1830), a dilation assembly (2200), and visualization and irrigation assembly (1700). FIG. 35 shows dilation assembly (2200) having been driven by slider (1122) from a proximal position to a distal position. Dilation assembly (2200) of the present example includes an elongate shaft (2202), an expandable dilator in the form of an inflatable balloon (2204), and a blunt distal tip electrode (2206). Balloon (2204) is depicted in a deflated state, though balloon (2204) may be inflated to dilate various anatomical passageways (e.g., Eustachian tube, paranasal sinus ostia, etc.) within the ear, nose, or throat. In some versions, distal tip electrode (2206) is configured to apply RF energy at a first polarity to serve as an electrode that is operable to apply monopolar RF energy to tissue contacting distal tip electrode (2206) and/or that is operable to apply bipolar RF energy to tissue contacting distal tip electrode (2206) (e.g., by cooperating with conductive elements (1864, 1866)). In versions where visualization and irrigation assembly (1700) is translatable relative to the rest of shaft assembly (1830), visualization and irrigation assembly (1700) may be translatable relative to the rest of shaft assembly (1830) independently of dilation assembly (2200) translating relative to the rest of shaft assembly (1830).

XVII. EXAMPLE OF RF ABLATION INSTRUMENT WITH BLUNT DISTAL TIP ELECTRODES AND DILATION ASSEMBLY

Figure 36:
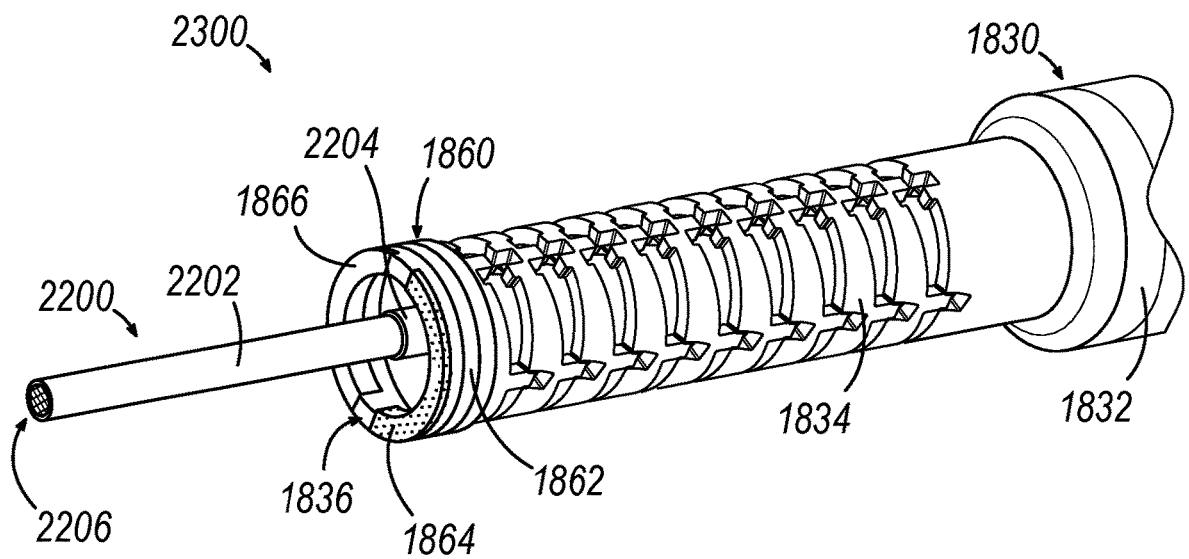
FIG. 36 depicts a perspective view of a distal portion of a shaft assembly of another example of an instrument that may be used to perform an ablation procedure in a nasal cavity, the instrument having a pair of distal tip electrodes, with an inflatable balloon of the instrument in a distal extended position relative to the distal end of the shaft assembly.

FIG. 36 shows a distal portion of another example of an instrument (2300) that may be used to deliver RF energy to tissue. Instrument (1300) is substantially similar to instrument (1100) except as otherwise described herein. Instrument (2300) of this example includes handle assembly (1110), shaft assembly (1830), and dilation assembly (2200).

FIG. 36 shows dilation assembly (2200) having been driven by slider (1122) from a proximal position to a distal position. Instrument (2300) shown in FIG. 36 may be configured and operable just like instrument (2100)) shown in FIG. 35 and described above, except that visualization and irrigation assembly (1700) is omitted from instrument (2300) of FIG. 36.

XVIII. EXAMPLE OF RF ABLATION INSTRUMENT WITH BLUNT DISTAL TIP ELECTRODES, BIOPSY ASSEMBLY, AND VISUALIZATION AND IRRIGATION ASSEMBLY

Figure 37:
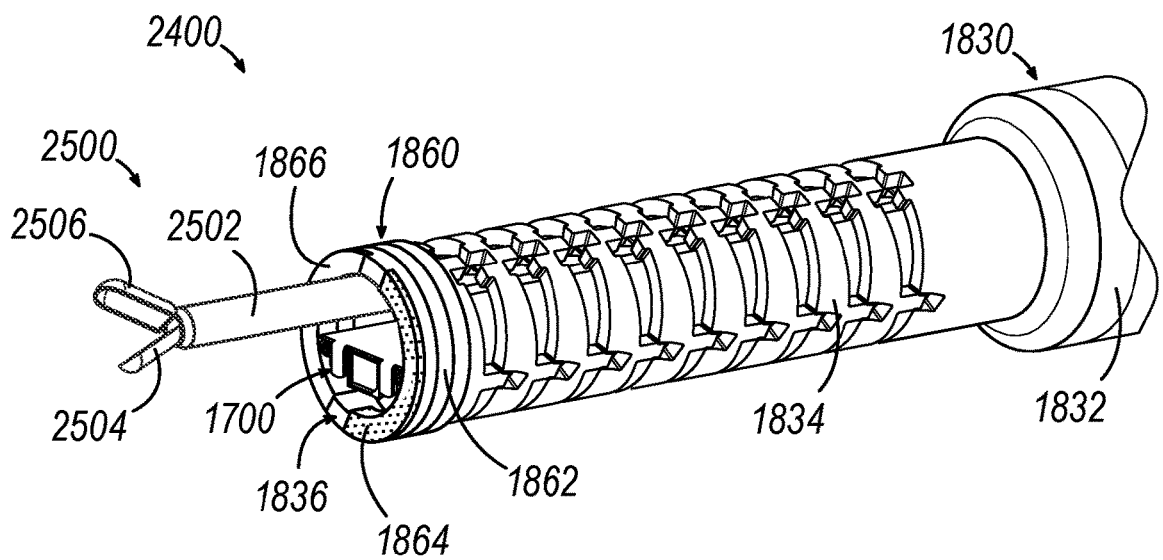
FIG. 37 depicts a perspective view of a distal portion of a shaft assembly of another example of an instrument that may be used to perform an ablation procedure in a nasal cavity, the instrument having a pair of distal tip electrodes and a visualization and irrigation assembly, with a pair of distal biopsy jaws of the instrument in a distal extended position relative to the distal end of the shaft assembly.

FIG. 37 shows a distal portion of another example of an instrument (2400) that may be used to deliver RF energy to tissue. Instrument (2400) is substantially similar to instrument (1100) except as otherwise described herein. Instrument (2400) of this example includes handle assembly (1110), shaft assembly (1830), a biopsy assembly (2500), and visualization and irrigation assembly (1700). FIG. 37 shows biopsy assembly (2500) having been driven by slider (1122) from a proximal position to a distal position. Biopsy assembly (2500) of the present example includes an elongate shaft (2502) and an opposed pair of distal biopsy jaws (2504, 2506) pivotably coupled to shaft (2502) for selectively chomping and capturing tissue therebetween. In versions where visualization and irrigation assembly (1700) is translatable relative to the rest of shaft assembly (1830), visualization and irrigation assembly (1700) may be translatable relative to the rest of shaft assembly (1830) independently of biopsy assembly (2500) translating relative to the rest of shaft assembly (1830).

XIX. EXEMPLARY METHOD OF ABLATING POSTERIOR NASAL NERVE

Having described exemplary features of instruments (1100, 1200, 1300, 1400, 1500, 1800, 1900, 2000, 2100, 2300, 2400) above, an exemplary method of performing an ablation on a posterior nasal nerve (40) of a patient with instrument (1100) will now be described in connection with FIGS. 38A-38B. While the exemplary method is showing being performed with instrument (1100), it will be appreciated that similar methods may be performed using instruments (1200, 1300, 1400, 1500, 1800, 1900, 2000, 2100, 2300, 2400). Additionally, while instrument (1100) is shown and described for treating a posterior nasal nerve, it will be appreciated that instrument (1100) may be employed in various other surgical applications for ablating other nerves or anatomical structures within the nasal cavity (10), or for ablating tissues in various other anatomical regions of a patient. For instance, the teachings herein may be combined with at least some of the teachings of U.S. Pat. Pub. No. 2019/0374280, entitled "Apparatus and Method for Performing Vidian Neurectomy Procedure," published Dec. 12, 2019, the disclosure of which is incorporated by reference herein, in its entirety; and/or with at least some of the teachings of U.S. Pat. App. No. 63/080,066, entitled "ENT Instrument with Expandable Ablation Feature," filed Sep. 18, 2020, the disclosure of which is incorporated by reference herein, in its entirety.

Figure 38A:
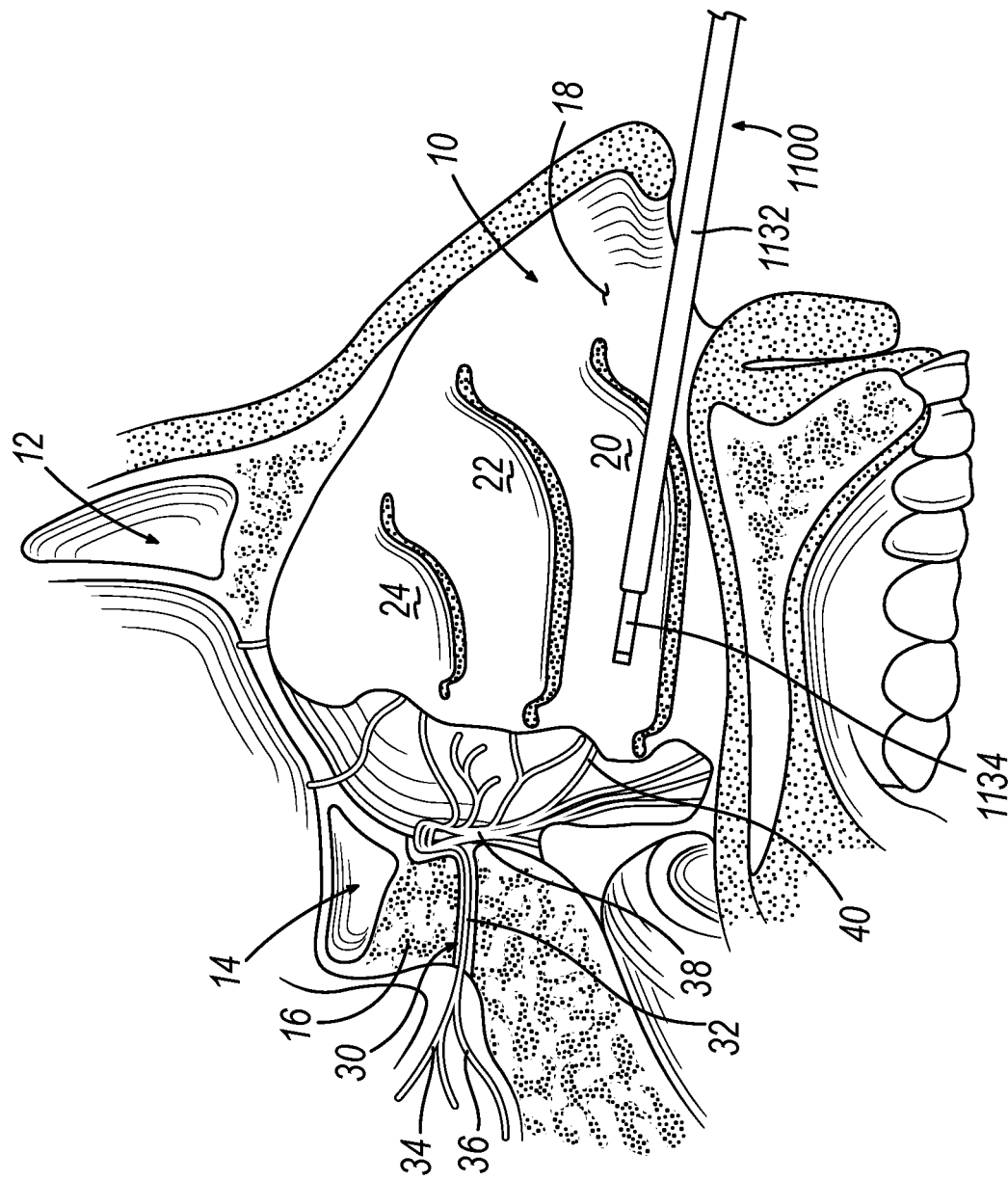
FIG. 38A depicts a left sagittal view of a portion of a patient's head, showing insertion of the distal portion of the instrument of FIG. 21 into the patient's nasal cavity in the region of a posterior nasal nerve, with the loop electrode and pair of needle electrodes in the respective proximal retracted positions relative to the shaft assembly.
Figure 38B:
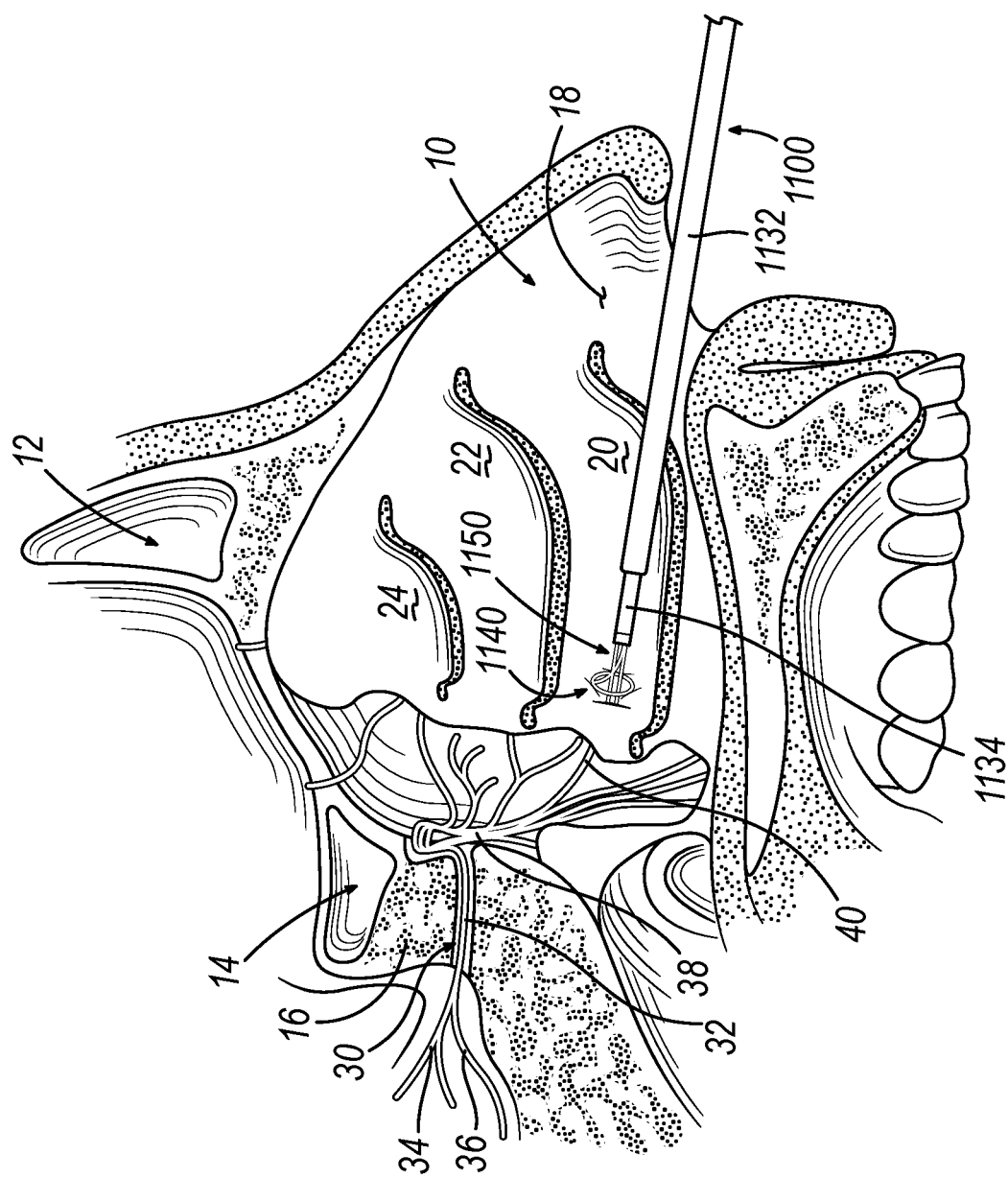
FIG. 38B depicts a left sagittal view of the portion of the patient's head with the distal portion of the instrument of FIG. 21 inserted in the patient's nasal cavity in the region of the posterior nasal nerve, with the loop electrode and pair of needle electrodes in the respective distal extended positions relative to the shaft assembly such that the needle electrodes pierce the nasal wall to deliver RF energy to the posterior nasal nerve past the surface of the nasal wall for providing deep, intra-tissue ablation of the posterior nasal nerve, and such that the loop electrode presses against the surface of the nasal wall adjacent to the entry points of the needle electrodes to deliver RF energy to the posterior nasal nerve from the surface of the nasal wall for providing shallow, surface ablation of the posterior nasal nerve.

As shown in FIG. 38A, the distal end of instrument (1100) is inserted into the nasal cavity (10) and is toward the posterior ends of the inferior and middle turbinates (20, 22), which may be performed under visualization provided by an endoscope (not shown), for example. Upon reaching a target site of the nasal wall (18) in which a target portion of the posterior nasal nerve (40) resides, the operator advances sliders (1120, 1122) distally to thereby extend loop electrode assembly (1140) and needle electrode assembly (1150), as shown in FIG. 38B, to urge arcuate arms (1142, 1144) against the surface of the nasal wall (18) and to insert needle electrodes (1170, 1172) through the surface of the nasal wall (18) between the contact points of the arcuate arms (1142, 1144) and thereby place arcuate arms (1142, 1144) and needle electrodes (1170, 1172) into electrical contact with a target portion of posterior nasal nerve (40). Loop electrode assembly (1140) and needle electrode assembly (1150) are then energized, either individually or together, with bipolar RF energy to thereby ablate the targeted portion of posterior nasal nerve (40) via shallow, deep, and/or volumetric ablation.

XX. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft having a distal end and defining a longitudinal axis; (b) a first electrode assembly at the distal end of the shaft, the first electrode assembly including a first member forming a loop shape, the first member of the first electrode assembly being operable to apply RF energy to tissue; and (c) a second electrode assembly at the distal end of the shaft, the second electrode assembly including a first needle having a sharp tip, the first needle being operable to penetrate tissue, the first needle being further operable to apply RF energy to tissue, the first needle being further configured to protrude distally past the first member of the first electrode assembly or laterally relative to the first member of the first electrode assembly.

Example 2

The apparatus of Example 1, the first member of the first electrode assembly and the first needle being operable to cooperatively apply bipolar RF energy to tissue.

Example 3

The apparatus of any one or more of Examples 1 through 2, the first electrode assembly further comprising a second member forming a loop shape, the second member of the first electrode assembly being operable to apply RF energy to tissue.

Example 4

The apparatus of Example 3, the first and second members of the first electrode assembly being operable to cooperatively apply bipolar RF energy to tissue.

Example 5

The apparatus of any one or more of Examples 1 through 4, the second electrode assembly further comprising a second needle having a sharp tip, the second needle being operable to penetrate tissue, the second needle being further operable to apply RF energy to tissue, the second needle being further configured to protrude distally past the first member of the first electrode assembly or laterally relative to the first member of the first electrode assembly.

Example 6

The apparatus of Example 5, the first and second needles of the second electrode assembly being operable to cooperatively apply bipolar RF energy to tissue.

Example 7

The apparatus of any one or more of Examples 5 through 6, the first needle comprising a straight needle aligned with the longitudinal axis of the shaft, the second needle extending obliquely relative to the longitudinal axis of the shaft.

Example 8

The apparatus of Example 7, the second needle extending on a curve diverging away from the longitudinal axis of the shaft.

Example 9

The apparatus of Example 8, the second needle being resiliently biased to extend along the curve.

Example 10

The apparatus of any one or more of Examples 7 through 9, the second electrode assembly further comprising a plurality of oblique needles extending obliquely relative to the longitudinal axis of the shaft, the plurality of oblique needles being angularly spaced apart from each other about the longitudinal axis of the shaft.

Example 11

The apparatus of Example 10, the shaft defining a distal opening and a plurality of lateral openings, the first needle being configured to pass through the distal opening, the plurality of needles being configured to pass through the lateral openings.

Example 12

The apparatus of any one or more of Examples 1 through 9, the second electrode assembly further comprising a plurality of oblique needles extending obliquely relative to the longitudinal axis of the shaft, the plurality of oblique needles being angularly spaced apart from each other about the longitudinal axis of the shaft, the shaft defining a distal opening, the first needle and the plurality of oblique needles being configured to pass through the distal opening.

Example 13

The apparatus of any one or more of Examples 1 through 12, further comprising a sheath operable to translate relative to the shaft.

Example 14

The apparatus of Example 13, the sheath being operable to selectively cover or uncover at least a portion of the first electrode assembly.

Example 15

The apparatus of any one or more of Examples 11 through 14, the sheath being operable to selectively cover or uncover at least a portion of the second electrode assembly.

Example 16

The apparatus of any one or more of Examples 1 through 15, the first needle being slidably disposed relative to the shaft.

Example 17

The apparatus of Example 16, the first needle being operable to selectively transition between a proximal position and a distal position, the first needle being retracted in the shaft in the proximal position, the first needle being advanced distally relative to the shaft in the distal position.

Example 18

The apparatus of any one or more of Examples 14 through 17, further comprising a handle assembly including a needle actuator, the needle actuator being operable to drive translation of the first needle relative to the shaft.

Example 19

The apparatus of any one or more of Examples 1 through 18, the shaft including a bendable section.

Example 20

The apparatus of Example 19, the bendable section being malleable.

Example 21

The apparatus of Example 19, the bendable section being steerable.

Example 22

The apparatus of Example 21, further comprising a handle assembly, the handle assembly including a steering actuator operable to drive steering of the bendable section of the shaft.

Example 23

The apparatus of any one or more of Examples 1 through 22, the first member of the first electrode assembly being coaxially aligned with the longitudinal axis of the shaft.

Example 24

The apparatus of Example 23, the first member of the first electrode assembly comprising a ring electrode coaxially disposed about the longitudinal axis of the shaft.

Example 25

The apparatus of Example 24, the first electrode assembly further comprising a plurality of ring electrodes coaxially disposed about the longitudinal axis of the shaft.

Example 26

The apparatus of Example 25, the ring electrodes being operable to cooperatively apply bipolar RF energy to tissue.

Example 27

The apparatus of any one or more of Examples 1 through 26, the second electrode assembly further comprising.

Example 28

The apparatus of any one or more of Examples 1 through 27, further comprising a blunt tip electrode at the distal end of the shaft.

Example 29

The apparatus of Example 28, the blunt tip electrode and the first member of the first electrode assembly being operable to cooperatively apply bipolar RF energy to tissue.

Example 30

The apparatus of any one or more of Examples 28 through 29, the blunt tip electrode and the first needle being operable to cooperatively apply bipolar RF energy to tissue.

Example 31

The apparatus of any one or more of Examples 28 through 30, the blunt tip electrode defining an opening, the first needle being configured to pass through the opening of the blunt tip electrode.

Example 32

The apparatus of any one or more of Examples 1 through 31, the shaft terminating in a distal tip, the first member of the first electrode assembly being positioned proximal to the distal tip of the shaft.

Example 33

The apparatus of any one or more of Examples 1 through 31, the shaft terminating in a distal tip, the first member of the first electrode assembly being positioned distal to the distal tip of the shaft.

Example 34

The apparatus of any one or more of Examples 1 through 33, the loop shape extending along a plane, the plane of the loop shape being oriented transversely relative to the longitudinal axis of the shaft.

Example 35

The apparatus of Example 34, the plane of the loop shape being oriented perpendicularly relative to the longitudinal axis of the shaft.

Example 36

The apparatus of any one or more of Examples 1 through 33, the loop shape extending along a plane, the plane of the loop shape being oriented parallel with the longitudinal axis of the shaft.

Example 37

The apparatus of any one or more of Examples 1 through 36, the first member of the first electrode assembly being resiliently biased to form the loop shape.

Example 38

The apparatus of any one or more of Examples 1 through 37, the first member of the first electrode assembly comprising: (i) a first arcuate segment, and (ii) a second arcuate segment, the second arcuate segment being angularly spaced apart from the first arcuate segment.

Example 39

The apparatus of Example 38, the first member of the first electrode assembly further comprising an insulating member angularly interposed between the first and second arcuate segments.

Example 40

The apparatus of any one or more of Examples 38 through 39, the first arcuate segment and the second arcuate segment being operable to cooperatively apply bipolar RF energy to tissue.

Example 41

The apparatus of any one or more of Examples 1 through 40, the loop shape defining a generally circular loop.

Example 42

The apparatus of any one or more of Examples 1 through 40, the loop shape defining a generally rectangular loop.

Example 43

The apparatus of any one or more of Examples 1 through 40, the loop shape defining a generally elliptical loop.

Example 44

The apparatus of any one or more of Examples 1 through 43, the first electrode assembly further comprising a second member forming a loop shape.

Example 45

The apparatus of Example 44, the loop shape of the second member being smaller than the loop shape of the first member.

Example 46

The apparatus of Example 45, the loop shape of the second member being nested within the loop shape of the first member.

Example 47

The apparatus of any one or more of Examples 44 through 46, the first and second members of the first electrode assembly being operable to cooperatively apply bipolar RF energy to tissue.

Example 48

The apparatus of any one or more of Examples 44 through 47, the first needle extending obliquely outwardly relative to the longitudinal axis of the shaft, from within the loop shape of the second member.

Example 49

The apparatus of Example 48, the first needle extending obliquely into a first region positioned laterally relative to the first electrode assembly, a second region being defined on a side of the first electrode assembly opposite to the first region, a portion of the first electrode assembly facing the second region including an electrically insulating material.

Example 50

The apparatus of any one or more of Examples 1 through 49, the loop shape extending along a plane that is parallel with the longitudinal axis of the shaft, the first needle extending obliquely relative to the plane of the loop shape.

Example 51

The apparatus of Example 50, the first needle extending obliquely from within an interior region defined by the loop shape.

Example 52

The apparatus of Example 51, the second electrode assembly further comprising a second needle, the second needle extending obliquely from within an interior region defined by the loop shape.

Example 53

The apparatus of Example 52, the second needle being positioned distally in relation to the first needle.

Example 54

The apparatus of any one or more of Examples 52 through 53, the first and second needles being operable to cooperatively apply bipolar RF energy to tissue.

Example 55

The apparatus of any one or more of Examples 1 through 54, the loop shape of the first member of the first electrode assembly extending along a plane that is oriented transversely relative to the longitudinal axis of the shaft, the first needle passing through the plane.

Example 56

The apparatus of Example 55, the second electrode assembly further comprising a second needle, the second needle passing through the plane.

Example 57

The apparatus of Example 56, the first and second needles being laterally spaced apart from each other.

Example 58

The apparatus of any one or more of Examples 55 through 57, the first and second needles being operable to cooperatively apply bipolar RF energy to tissue.

Example 59

The apparatus of any one or more of Examples 1 through 58, the second electrode assembly further comprising: (i) an electrode shaft coaxially disposed about the first needle, and (ii) a ring electrode positioned on the electrode shaft, the ring electrode being positioned distally relative to the distal end of the shaft.

Example 60

The apparatus of Example 59, the ring electrode being further positioned distally relative to the first electrode assembly.

Example 61

The apparatus of any one or more of Examples 59 through 60, the first needle and the ring electrode being operable to cooperatively apply bipolar RF energy to tissue.

Example 62

The apparatus of any one or more of Examples 1 through 61, the first needle defining a lumen, the first needle being operable to distally dispense fluid via the lumen.

Example 63

The apparatus of any one or more of Examples 1 through 62, further comprising a position sensor, the position sensor being configured to generate signals indicative of a position of one or both of the first or second electrode assemblies in three-dimensional space.

Example 64

The apparatus of any one or more of Examples 1 through 63, the shaft, the first electrode assembly, and the second electrode assembly being configured to fit within a nasal cavity of a patient.

Example 65

An apparatus, comprising: (a) a shaft having a distal end and defining a longitudinal axis; (b) a first ring electrode positioned on the shaft, the first ring electrode being coaxially positioned about the longitudinal axis, the first ring electrode being proximal to the distal end of the shaft; (c) a first needle electrode at the distal end of the shaft, the first needle electrode having a sharp tip, the first needle electrode being operable to penetrate tissue, the first ring electrode and the first needle electrode being operable to cooperatively apply bipolar RF energy to tissue.

Example 66

The apparatus of Example 65, the first needle electrode extending distally along the longitudinal axis.

Example 67

The apparatus of any one or more of Examples 65 through 66, further comprising a second ring electrode, the second ring electrode being coaxially positioned about the longitudinal axis, the second ring electrode being proximal to the distal end of the shaft.

Example 68

The apparatus of Example 67, the first and second ring electrodes being operable to cooperatively apply bipolar RF energy to tissue.

Example 69

The apparatus of any one or more of Examples 65 through 68, the first needle electrode extending obliquely relative to the longitudinal axis.

Example 70

The apparatus of any one or more of Examples 65 through 69, further comprising a second needle electrode, the second needle electrode extending obliquely relative to the longitudinal axis.

Example 71

The apparatus of any one or more of Examples 65 through 70, further comprising a sheath slidably disposed about the shaft.

Example 72

The apparatus of Example 71, the sheath being operable to selectively cover and uncover the first ring electrode.

Example 73

The apparatus of any one or more of Examples 65 through 72, the first needle electrode being slidably disposed relative to the shaft.

Example 74

The apparatus of Example 73, further comprising an actuator operable to drive the first needle electrode to translate relative to the shaft.

Example 75

The apparatus of any one or more of Examples 65 through 72, further comprising a tip electrode located at the distal end of the shaft.

Example 76

The apparatus of Example 75, the first ring electrode and the tip electrode being operable to cooperatively apply bipolar RF energy to tissue.

Example 77

The apparatus of any one or more of Examples 75 through 76, the first needle electrode and the tip electrode being operable to cooperatively apply bipolar RF energy to tissue.

Example 78

An apparatus, comprising: (a) a shaft having a distal end and defining a longitudinal axis, the distal end terminating in a distal tip; (b) a loop electrode assembly at the distal end of the shaft, the loop electrode forming a loop shape extending along a plane that is transversely oriented relative to the longitudinal axis of the shaft, the loop electrode assembly being positioned distally in relation to the distal tip of the shaft; and (c) a first needle electrode at the distal end of the shaft, the first needle electrode having a sharp tip, the first needle electrode being operable to penetrate tissue, the loop electrode assembly and the first needle electrode each being operable to apply RF energy to tissue.

Example 79

The apparatus of Example 78, the loop electrode assembly and the first needle electrode being operable to cooperatively apply bipolar RF energy to tissue.

Example 80

The apparatus of any one or more of Examples 78 through 79, the loop electrode assembly comprising: (i) a first arcuate segment, and (ii) a second arcuate segment, the second arcuate segment being angularly spaced apart from the first arcuate segment.

Example 81

The apparatus of Example 80, the loop electrode assembly further comprising an insulating member angularly interposed between the first and second arcuate segments.

Example 82

The apparatus of any one or more of Examples 80 through 81, the first arcuate segment and the second arcuate segment being operable to cooperatively apply bipolar RF energy to tissue.

Example 83

The apparatus of any one or more of Examples 78 through 82, the loop shape defining a generally circular loop.

Example 84

The apparatus of any one or more of Examples 78 through 83, the first needle electrode being configured to pass through the plane of the loop shape such that the sharp tip is positioned distally in relation to the loop shape.

Example 85

The apparatus of any one or more of Examples 78 through 84, further comprising a plurality of needle electrodes at the distal end of the shaft, the plurality of needle electrodes being operable to cooperatively apply bipolar RF energy to tissue.

Example 86

The apparatus of Example 85, at least some of the needle electrodes of the plurality of needle electrodes being configured to extend obliquely relative to the longitudinal axis of the shaft.

Example 87

The apparatus of any one or more of Examples 78 through 86, further comprising a second needle electrode at the distal end of the shaft, the second needle having a sharp tip, the second needle electrode being operable to penetrate tissue.

Example 88

The apparatus of Example 87, the first and second needle electrodes being operable to cooperatively apply bipolar RF energy to tissue.

Example 89

The apparatus of any one or more of Examples 87 through 88, the first and second needle electrodes being laterally spaced apart from each other.

Example 90

The apparatus of any one or more of Examples 87 through 89, the first and second needle electrodes being parallel with each other.

Example 91

The apparatus of Example 90, the first and second needle electrodes being parallel with the longitudinal axis of the shaft.

Example 92

The apparatus of any one or more of Examples 78 through 91, further comprising: (i) an electrode shaft coaxially disposed about the first needle electrode, and (ii) a ring electrode positioned on the electrode shaft, the ring electrode being positioned distally relative to the distal end of the shaft.

Example 93

The apparatus of Example 92, the ring electrode being further positioned distally relative to the loop electrode assembly.

Example 94

The apparatus of any one or more of Examples 92 through 93, the first needle electrode and the ring electrode being operable to cooperatively apply bipolar RF energy to tissue.

Example 95

An apparatus, comprising: (a) a shaft having a distal end and defining a longitudinal axis, the distal end terminating in a distal tip; (b) a loop electrode assembly at the distal end of the shaft, the loop electrode assembly including a first member forming a first loop shape extending along a plane that is parallel with the longitudinal axis of the shaft, the loop electrode assembly being positioned distally in relation to the distal tip of the shaft; and (c) a first needle electrode at the distal end of the shaft, the first needle having a sharp tip, the first needle being operable to penetrate tissue, the loop electrode assembly and the first needle electrode each being operable to apply RF energy to tissue.

Example 96

The apparatus of Example 95, the loop electrode assembly and the first needle electrode being operable to cooperatively apply bipolar RF energy to tissue.

Example 97

The apparatus of any one or more of Examples 95 through 96, the loop electrode assembly including a second member forming a second loop shape extending along a plane that is parallel with the longitudinal axis of the shaft.

Example 98

The apparatus of Example 97, the second loop shape being nested within the first loop shape.

Example 99

The apparatus of any one or more of Examples 89 through 90, the first member and the second member being operable to cooperatively apply bipolar RF energy to tissue.

Example 100

The apparatus of any one or more of Examples 95 through 96, the first needle electrode extending obliquely relative to the plane associated with the first loop shape.

Example 101

The apparatus of Example 100, the first needle electrode extending obliquely along a curved path.

Example 102

The apparatus of any one or more of Examples 95 through 101, the first loop shape being generally rectangular.

Example 103

The apparatus of any one or more of Examples 95 through 101, the first loop shape being generally elliptical.

Example 104

The apparatus of any one or more of Examples 95 through 103, the first member including a first segment and a second segment, the first and second segments of the first member being operable to cooperatively apply bipolar RF energy to tissue.

Example 105

The apparatus of any one or more of Examples 95 through 103, the first needle electrode being positioned within an interior region defined by the first loop shape.

Example 106

The apparatus of any one or more of Examples 95 through 105, further comprising a second needle electrode, the second needle electrode being positioned within an interior region defined by the first loop shape.

Example 107

The apparatus of Example 106, the second needle electrode being positioned distally in relation to the first needle electrode.

Example 108

The apparatus of any one or more of Examples 106 through 107, the first and second needle electrodes being operable to cooperatively apply bipolar RF energy to tissue.

Example 109

The apparatus of any one or more of Examples 98 through 108, the second needle electrode extending obliquely relative to the plane associated with the first loop shape.

Example 110

The apparatus of any one or more of Examples 95 through 109, the first needle electrode extending obliquely into a first region positioned laterally relative to the loop electrode assembly, a second region being defined on a side of the loop electrode assembly opposite to the first region, a portion of the loop electrode assembly facing the second region including an electrically insulating material.

Example 111

A method, comprising: (a) pressing a loop electrode assembly against tissue within a nasal cavity of a patient; (b) driving a needle electrode through tissue within the nasal cavity of the patient; and (c) applying bipolar RF energy to tissue within the nasal cavity of the patient via the loop electrode assembly and the needle electrode.

Example 112

An apparatus, comprising: (a) a shaft having a distal end and defining a longitudinal axis; (b) a first electrode assembly at the distal end of the shaft, the first electrode assembly including a member operable to apply RF energy to tissue; and (c) a second electrode assembly at the distal end of the shaft, the second electrode assembly including a first needle having a sharp tip, the first needle being operable to penetrate tissue, the first needle being further operable to apply RF energy to tissue, the first needle being selectively longitudinally translatable relative to the shaft between a proximal retracted position and a distal extended position in which the first needle protrudes distally past the member of the first electrode assembly.

Example 113

The apparatus of Example 112, wherein the member of the first electrode assembly and the first needle are operable to cooperatively apply bipolar RF energy to tissue.

Example 114

The apparatus of any one or more of Examples 112 through 113, wherein the member of the first electrode assembly comprises: (i) a first arcuate segment, and (ii) a second arcuate segment, the second arcuate segment being angularly spaced apart from the first arcuate segment.

Example 115

The apparatus of Example 114, wherein the member of the first electrode assembly further comprises an insulating member angularly interposed between the first and second arcuate segments.

Example 116

The apparatus of any one or more of Examples 114 through 115, wherein the first arcuate segment and the second arcuate segment are operable to cooperatively apply bipolar RF energy to tissue.

Example 117

The apparatus of any one or more of Examples 112 through 116, wherein the member of the first electrode assembly includes a blunt tip electrode fixedly secured to the distal end of the shaft.

Example 118

The apparatus of Example 117, wherein the blunt tip electrode forms a ring shape and defines an opening, the first needle being configured to pass through the opening of the blunt tip electrode.

Example 119

The apparatus of Example 118, wherein the ring shape extends along a plane, the plane of the ring shape being oriented transversely relative to the longitudinal axis of the shaft.

Example 120

The apparatus of Example 119, wherein the plane of the ring shape is oriented perpendicularly relative to the longitudinal axis of the shaft.

Example 121

The apparatus of any one or more of Examples 112 through 116, wherein the member of the first electrode assembly is selectively longitudinally translatable relative to the shaft.

Example 122

The apparatus of Example 121, wherein the member of the first electrode assembly forms a loop shape.

Example 123

The apparatus of Example 122, wherein the loop shape extends along a plane, the plane of the loop shape being oriented transversely relative to the longitudinal axis of the shaft.

Example 124

The apparatus of Example 123, wherein the plane of the loop shape is oriented perpendicularly relative to the longitudinal axis of the shaft.

Example 125

The apparatus of any one or more of Examples 122 through 124, wherein the member of the first electrode assembly is resiliently biased to form the loop shape.

Example 126

The apparatus of any one or more of Examples 122 through 125, wherein the loop shape defines a generally circular loop.

Example 127

The apparatus of any one or more of Examples 112 through 126, wherein the second electrode assembly further comprises a second needle having a sharp tip, the second needle being operable to penetrate tissue, the second needle being further operable to apply RF energy to tissue, the second needle being selectively longitudinally translatable relative to the shaft between a proximal retracted position and a distal extended position in which the second needle protrudes distally past the member of the first electrode assembly.

Example 128

The apparatus of Example 127, wherein the first and second needles are laterally spaced apart from each other.

Example 129

The apparatus of Example 128, wherein the second electrode assembly further comprises an insulating member laterally interposed between the first and second needles.

Example 130

The apparatus of any one or more of Examples 127 through 129, wherein the first and second needles of the second electrode assembly are operable to cooperatively apply bipolar RF energy to tissue.

Example 131

The apparatus of any one or more of Examples 112 through 126, wherein the first needle further includes a needle shaft comprising a first insulative segment and a first conductive segment operable to apply RF energy to tissue.

Example 132

The apparatus of Example 131, wherein the needle shaft further comprises a second conductive segment operable to apply RF energy to tissue and axially spaced apart from the first conductive segment, wherein the first insulative segment is axially interposed between the first and second conductive segments.

Example 133

The apparatus of Example 132, wherein the first and second conductive segments of the needle shaft are operable to cooperatively apply bipolar RF energy to tissue.

Example 134

The apparatus of any one or more of Examples 131 through 133, wherein the first conductive segment is configured to protrude distally past the member of the first electrode assembly when the first needle is in the distal extended position.

Example 135

The apparatus of any one or more of Examples 131 through 134, wherein the first conductive segment includes the sharp tip of the first needle.

Example 136

The apparatus of any one or more of Examples 112 through 126, wherein the first needle further includes an insulative needle shaft and at least one conductive ring positioned about the insulative needle shaft.

Example 137

The apparatus of Example 136, wherein the at least one conductive ring includes first and second conductive rings axially spaced apart from each other along the insulative needle shaft.

Example 138

The apparatus of Example 137, wherein the first and second conductive rings of the first needle are operable to cooperatively apply bipolar RF energy to tissue.

Example 139

The apparatus of any one or more of Examples 136 through 138, wherein the at least one conductive ring is configured to protrude distally past the member of the first electrode assembly when the first needle is in the distal extended position.

Example 140

The apparatus of any one or more of Examples 112 through 139, wherein the first needle defines a lumen, the first needle being operable to distally dispense fluid via the lumen.

Example 141

The apparatus of any one or more of Examples 112 through 140, further comprising a position sensor, the position sensor being configured to generate signals indicative of a position of one or both of the first or second electrode assemblies in three-dimensional space.

Example 142

An apparatus, comprising: (a) a shaft having a distal end and defining a longitudinal axis; (b) a first electrode assembly at the distal end of the shaft, the first electrode assembly comprising: (i) a first conductive segment, wherein the first conductive segment is operable to apply RF energy to tissue at a first polarity, and (ii) a second conductive segment angularly spaced apart from the first conductive segment, wherein the second conductive segment is operable to apply RF energy to tissue at a second polarity; and (c) a second electrode assembly at the distal end of the shaft, the second electrode assembly comprising: (i) a first needle having a sharp tip operable to penetrate tissue, (ii) a first conductive portion presented by the first needle, wherein the first conductive portion is operable to apply RF energy to tissue at the second polarity, and (iii) a second conductive portion, wherein the second conductive portion is operable to apply RF energy to tissue at the first polarity, wherein the first conductive segment and the second conductive segment are operable to cooperatively apply bipolar RF energy to tissue, wherein the first conductive portion and the second conductive portion are operable to cooperatively apply bipolar RF energy to tissue, wherein the first conductive segment and the first conductive portion are operable to cooperatively apply bipolar RF energy to tissue, and wherein the second conductive segment and the second conductive portion are operable to cooperatively apply bipolar RF energy to tissue.

Example 143

The apparatus of Example 142, wherein the second conductive portion is presented by the first needle.

Example 144

The apparatus of Example 143, wherein the first needle includes a needle shaft, wherein the first and second conductive portions are each presented by the needle shaft, wherein the needle shaft includes an insulative portion between the first and second conductive portions.

Example 145

The apparatus of Example 143, wherein the first needle includes an insulative needle shaft, wherein the first and second conductive portions include first and second conductive rings, respectively, positioned about the insulative needle shaft.

Example 146

The apparatus of Example 142, further comprising a second needle having a sharp tip operable to penetrate tissue, wherein the second conductive portion is presented by the second needle.

Example 147

The apparatus of any one or more of Examples 142 through 146, wherein the first conductive segment is positioned on a first lateral side relative to the longitudinal axis of the shaft, wherein the second conductive segment is positioned on a second lateral side relative to the longitudinal axis of the shaft.

Example 148

The apparatus of Example 147, wherein the first conductive portion is positioned on the first lateral side relative to the longitudinal axis of the shaft, wherein the second conductive portion is positioned on the second lateral side relative to the longitudinal axis of the shaft.

Example 149

The apparatus of any one or more of Examples 142 through 148, wherein the first needle is selectively longitudinally translatable relative to the shaft between a proximal retracted position and a distal extended position in which the first needle protrudes distally past the first and second conductive segments of the first electrode assembly.

Example 150

The apparatus of any one or more of Examples 142 through 149, wherein the first and second conductive segments of the first electrode assembly are fixedly secured to the distal end of the shaft.

Example 151

The apparatus of any one or more of Examples 142 through 149, wherein the first and second conductive segments of the first electrode assembly are selectively longitudinally translatable relative to the shaft.

Example 152

The apparatus of Example 151, wherein the first electrode assembly forms a loop shape extending along a plane that is transversely oriented relative to the longitudinal axis of the shaft.

Example 153

The apparatus of Example 152, wherein the loop shape defines a generally circular loop.

Example 154

The apparatus of any one or more of Examples 152 through 153, wherein the first electrode assembly is resiliently biased to form the loop shape.

Example 155

The apparatus of any one or more of Examples 142 through 154, wherein the first electrode assembly defines an opening, the first needle being configured to pass through the opening of the first electrode assembly.

Example 156

A method, comprising: (a) pressing an electrode assembly against tissue within a nasal cavity of a patient; (b) driving a needle electrode through tissue within the nasal cavity of the patient; (c) selecting a bipolar RF energy application mode from a plurality of bipolar RF energy application modes, wherein the plurality of bipolar RF energy application modes includes a shallow bipolar RF energy application mode, a deep bipolar RF energy application mode, and a volumetric bipolar RF energy application mode; and (d) applying bipolar RF energy to tissue within the nasal cavity of the patient via at least one of the electrode assembly or the needle electrode in the selected bipolar RF energy application mode.

Example 157

An apparatus, comprising: (a) a shaft assembly having a distal end; and (b) an electrode assembly at the distal end of the shaft assembly, the electrode assembly comprising: (i) a first conductive segment extending along a first angular range at the distal end of the shaft assembly, wherein the first conductive segment is operable to apply RF energy to tissue at a first polarity, and (ii) a second conductive segment angularly spaced apart from the first conductive segment, the second conductive segment extending along a second angular range at the distal end of the shaft assembly, wherein the second conductive segment is operable to apply RF energy to tissue at a second polarity such that the first and second conductive segments are operable to apply bipolar RF energy to tissue.

Example 158

The apparatus of Example 157, further comprising a visualization assembly at the distal end of the shaft, the visualization assembly including a camera.

Example 159

The apparatus of Example 158, the visualization assembly being longitudinally fixed relative to the shaft assembly.

Example 160

The apparatus of Example 158, the visualization assembly and the shaft assembly being configured to enable relative longitudinal translation between the visualization assembly and the shaft assembly.

Example 161

The apparatus of any one or more of Examples 158 through 160, the visualization assembly and the electrode assembly being configured to enable relative longitudinal translation between the visualization assembly and the electrode assembly.

Example 162

The apparatus of any one or more of Examples 158 through 161, further comprising a fluid conduit, the fluid conduit being positioned and configured to expel to one or both of (i) flush debris from the camera, or (ii) promote continuity between the first and second conductive segments and the tissue.

Example 163

The apparatus of Example 162, the visualization assembly further comprising a liquid diverting member positioned and configured to divert liquid expelled via the fluid conduit toward the camera.

Example 164

The apparatus of any one or more of Examples 162 through 163, the fluid conduit being further configured to apply suction at the distal end of the shaft assembly.

Example 165

The apparatus of any one or more of Examples 158 through 164, the visualization assembly further comprising an illuminating element configured to illuminate a field of view of the camera.

Example 166

The apparatus of Example 165, the illuminating element comprising an LED.

Example 167

The apparatus of any one or more of Examples 157 through 166, the shaft assembly including a rigid proximal portion and a flexible distal portion, the flexible distal portion being configured to enable lateral deflection of the distal end away from or toward a longitudinal axis defined by the rigid proximal portion.

Example 168

The apparatus of Example 167, the shaft assembly further comprising a rigid distal portion defining the distal end, the flexible distal portion being longitudinally interposed between the rigid proximal portion and the rigid distal portion.

Example 169

The apparatus of any one or more of Examples 157 through 168, the electrode assembly further comprising a distal tip member secured to the distal end of the shaft assembly, the first and second conductive segments being secured to the distal tip member.

Example 170

The apparatus of Example 169, the distal tip member comprising an electrically non-conductive material.

Example 171

The apparatus of any one or more of Examples 157 through 170, the first conductive segment having an arcuate shape, the second conductive segment having an arcuate shape.

Example 172

The apparatus of Example 171, the first and second conductive segments together defining a generally circular shape.

Example 173

The apparatus of any one or more of Examples 157 through 172, the electrode assembly defining a first angular gap between the first and second conductive segments.

Example 174

The apparatus of Example 173, the electrode assembly further defining a second angular gap between the first and second conductive segments.

Example 175

The apparatus of Example 174, the second angular gap being angularly spaced 180 degrees away from the first angular gap.

Example 176

The apparatus of any one or more of Examples 157 through 175, the distal end of the shaft assembly defining a distally facing circular edge, the first conductive segment extending through the first angular range along the distally facing circular edge, the second conductive segment extending through the second angular range along the distally facing circular edge.

Example 177

The apparatus of any one or more of Examples 157 through 176, the first conductive segment including a first distally facing portion, the second conductive segment including a second distally facing portion.

Example 178

The apparatus of any one or more of Examples 157 through 177, the first conductive segment including a first radially-outwardly facing portion, the second conductive segment including a second radially-outwardly facing portion.

Example 179

The apparatus of any one or more of Examples 157 through 178, the first conductive segment including a first radially-inwardly facing portion, the second conductive segment including a second radially-inwardly facing portion.

Example 180

The apparatus of any one or more of Examples 157 through 179, the shaft assembly defining a working channel.

Example 181

The apparatus of Example 180, the working channel being sized and configured to enable advancement of a working element distally past the distal end of the shaft assembly and distally past the electrode assembly.

XXI. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
   (a) a shaft assembly having a distal end comprising a hollow annular tip portion, the hollow annular tip portion comprising:
      (i) an inner surface,
      (ii) an outer surface, and
      (iii) a distally-facing surface that extends between the inner surface and the outer surface; and

(b) an electrode assembly at the hollow annular tip portion, the electrode assembly comprising:
  (i) a first conductive segment disposed on at least one of the inner surface, the outer surface, or the distally-facing surface, the first conductive segment being operable to apply RF energy to tissue at a first polarity, and
  (ii) a second conductive segment angularly spaced apart from the first conductive segment, the second conductive segment disposed on the inner surface, the outer surface, or the distally-facing surface, the second conductive segment being operable to apply RF energy to tissue at a second polarity such that the first and second conductive segments are operable to apply bipolar RF energy to tissue.

2. The apparatus of claim 1, further comprising a visualization assembly at the distal end of the shaft assembly, the visualization assembly including a camera.

3. The apparatus of claim 2, the visualization assembly and the shaft assembly being configured to enable relative longitudinal translation between the visualization assembly and the shaft assembly.

4. The apparatus of claim 2, the visualization assembly and the electrode assembly being configured to enable relative longitudinal translation between the visualization assembly and the electrode assembly.

5. The apparatus of claim 2, further comprising a fluid conduit, the fluid conduit being positioned and configured to expel liquid to one or both of:
  (i) flush debris from the camera, or
  (ii) promote continuity between the first and second conductive segments and the tissue.

6. The apparatus of claim 5, the visualization assembly further comprising a liquid diverting member positioned and configured to divert liquid expelled via the fluid conduit toward the camera.

7. The apparatus of claim 5, the fluid conduit being further configured to apply suction at the distal end of the shaft assembly.

8. The apparatus of claim 2, the visualization assembly further comprising an illuminating element configured to illuminate a field of view of the camera.

9. The apparatus of claim 1, the shaft assembly including a rigid proximal portion and a flexible distal portion, the flexible distal portion being configured to enable lateral deflection of the distal end away from or toward a longitudinal axis defined by the rigid proximal portion.

10. The apparatus of claim 1, the hollow annular tip portion comprising an electrically non-conductive material.

11. The apparatus of claim 1, the first conductive segment having an arcuate shape, and the second conductive segment having an arcuate shape.

12. The apparatus of claim 1, the electrode assembly defining a first angular gap between the first and second conductive segments.

13. The apparatus of claim 1, the first conductive segment including a first distally facing portion that extends along the distally-facing surface, the second conductive segment including a second distally facing portion that extends along the distally-facing surface.

14. The apparatus of claim 1, the first conductive segment including a first radially-outwardly facing portion that extends along the outer surface, the second conductive segment including a second radially-outwardly facing portion that extends along the outer surface.

15. The apparatus of claim 1, the first conductive segment including a first radially-inwardly facing portion that extends along the inner surface, the second conductive segment including a second radially-inwardly facing portion that extends along the inner surface.

16. The apparatus of claim 1, the shaft assembly defining a working channel, the working channel being sized and configured to enable advancement of a working element distally past the distal end of the shaft assembly and distally past the electrode assembly.

17. An apparatus, comprising:
  (a) a shaft having a distal end and defining a longitudinal axis;
  (b) a first electrode assembly at the distal end of the shaft, the first electrode assembly including a loop member that defines an interior area, the loop member of the first electrode assembly being operable to apply RF energy to tissue; and
  (c) a second electrode assembly at the distal end of the shaft, the second electrode assembly including a needle having a sharp tip, the needle being operable to penetrate tissue, the needle being further operable to apply RF energy to tissue, the needle being further configured to selectively extend though the interior area and distally past the loop member of the first electrode assembly such that the loop member surrounds the needle.

18. The apparatus of claim 17, the loop member being operable to apply RF energy to tissue at a first polarity, and the needle being operable to apply RF energy to tissue at a second polarity such that the loop member and the needle cooperate to apply bipolar RF energy to tissue.

19. An apparatus, comprising:
  (a) a shaft having a distal end and defining a longitudinal axis;
  (b) a first electrode assembly at the distal end of the shaft, the first electrode assembly including a loop member that is configured to selectively slide relative to the shaft between a retracted position and an extended position and is operable to apply RF energy to tissue, the loop member being configured to be substantially coaxial with the shaft when the loop member is in the extended position; and
  (c) a second electrode assembly at the distal end of the shaft, the second electrode assembly including a needle having a sharp tip, the needle being operable to penetrate tissue, the needle being further operable to apply RF energy to tissue, the needle being selectively longitudinally translatable relative to the shaft between a proximal retracted position and a distal extended position, the needle protruding through and distally past the loop member such that the loop member is configured to surround the needle when the loop member is in the extended position and the needle is in the distal extended position.

20. The apparatus of claim 19, the loop member being operable to apply RF energy to tissue at a first polarity, and the needle being operable to apply RF energy to tissue at a second polarity such that the loop member and the needle cooperate to apply bipolar RF energy to tissue.

* * * * *